US008993622B2

(12) United States Patent
Wadell et al.

(10) Patent No.: US 8,993,622 B2
(45) Date of Patent: Mar. 31, 2015

(54) ANTIVIRAL COMPOUNDS

(75) Inventors: Göran Wadell, Umea (SE); Karin Edlund, Umeå (SE); Marten Strand, Umeå (SE); Emma Andersson, Umeå (SE); Christopher Öberg, Umeå (SE); Mikael Elofsson, Umeå (SE); Ya-Fang Mei, Umeå (SE)

(73) Assignee: Eirium AB, Umea (SE)

( * ) Notice: Subject to any disclaimer, the term of this patent is extended or adjusted under 35 U.S.C. 154(b) by 0 days.

(21) Appl. No.: 13/703,481

(22) PCT Filed: Jun. 13, 2011

(86) PCT No.: PCT/SE2011/050724
§ 371 (c)(1),
(2), (4) Date: Apr. 9, 2013

(87) PCT Pub. No.: WO2011/155898
PCT Pub. Date: Dec. 15, 2011

(65) Prior Publication Data

US 2013/0210915 A1 Aug. 15, 2013

(30) Foreign Application Priority Data

Jun. 11, 2010 (SE) ................................ SE1000623-7
Jun. 11, 2010 (SE) ................................ SE1000624-5

(51) Int. Cl.

| | |
|---|---|
| ***A01N 37/12*** | (2006.01) |
| ***A01N 37/44*** | (2006.01) |
| ***A61K 31/24*** | (2006.01) |
| ***A61K 31/195*** | (2006.01) |
| ***C07C 229/00*** | (2006.01) |
| ***C07C 233/81*** | (2006.01) |
| ***A61K 31/167*** | (2006.01) |
| ***A61K 31/18*** | (2006.01) |
| ***A61K 31/196*** | (2006.01) |
| ***A61K 31/245*** | (2006.01) |
| ***C07C 237/40*** | (2006.01) |
| ***C07C 237/42*** | (2006.01) |
| ***C07C 311/08*** | (2006.01) |
| ***C07C 311/21*** | (2006.01) |

(52) U.S. Cl.
CPC ............. *C07C 233/81* (2013.01); *A61K 31/167* (2013.01); *A61K 31/18* (2013.01); *A61K 31/196* (2013.01); *A61K 31/245* (2013.01); *C07C 237/40* (2013.01); *C07C 237/42* (2013.01); *C07C 311/08* (2013.01); *C07C 311/21* (2013.01); *C07C 2101/14* (2013.01)
USPC .............. 514/539; 514/563; 560/48; 562/457

(58) Field of Classification Search
None
See application file for complete search history.

(56) References Cited

U.S. PATENT DOCUMENTS

2006/0035245 A1 2/2006 Ason et al.
2007/0099919 A1 * 5/2007 Rana .......................... 514/237.5

FOREIGN PATENT DOCUMENTS

| | | |
|---|---|---|
| JP | 11-171848 | 6/1999 |
| WO | WO00/40237 | 7/2000 |
| WO | WO2008/079460 | 7/2008 |

OTHER PUBLICATIONS

Dörwald, F. Zaragoza. (Side Reactions in Organic Synthesis: A Guide to Successful Synthesis Design, Weinheim: Wiley-VCH Verlag GmbH & Co. KGaA, 2005, Preface).*

Jordan, V. C. (Nature Reviews: Drug Discovery, 2, 2003, 205-213).*

JP 11171848 STN Registry record for CAS 228580-61-8 issued Jun. 29, 1999.*

Abdel-Monem and Abdel-Hafez, "An efficient, convenient synthesis of novel medium-sized 13H-Dibenzo[d,h][1,3,7]oxadiazecine-8, 14-dione macrolides as anticipated antineoplastic agents," *Biorg. and Med. Chem.,* 2002, 10:2297-2302.

Allard et al, "Rapid typing of human adenoviruses by a general PCR combined with restriction endonuclease analysis.," *Journal Clinical Microbiology,* 2001, 39:498-505.

Andersson et al., "Small-molecule screening using a whole-cell viral replication reporter gene assay identifies1-{[2-(benzoylamino)benzoyl]amino}-benzoic acid as a novel antiadenoviral compound," *Antimicrobial agents and chemother.,* 2010, 54(9):3871-3877.

Baldwin et al., "Outcome and clinical course of 100 patients with adenovirus infection following bone marrow transplantation," *Bone Marrow Transplantation,* 2000, 26:1333-1338.

CA—Abstract SU323402, dated Jun. 22, 1970, Bolotin and Brudz, "Esters of tosylanthranoyllanthranilic acid," copyright 2013, 1 page.

Deng et al., "Dynamic receptor-based pharmacophore model development and its application in designing novel HIV-1 integrase inhibitors," *J. Med. Chem.,* 2005, 48:1496-1505.

Di Grandi et al., "Thiourea inhibitors of herpesviruses. Part 3. Inhibitors of varicella zoster virus," *Bioorgan. And Med. Chem. Letters,* 2004, 14:4157-4160.

Hashimoto, "New methods and reagents in organic synthesis," 14.1 A simple efficeitn preparation of methyl esters with trimethylsilyldiazomethane (TMSCHN2) and its application to gas chromatographic analysis of fatty acids, *Chem. Pharm. Bull.* 1981, 29(5):1475-1478.

Hierholzer, "Adenoviruses in the immunocompromised host," *Clinical Microbiology Reviews,* 1992, 5:262-274.

(Continued)

*Primary Examiner* — James D. Anderson
*Assistant Examiner* — William Lee
(74) *Attorney, Agent, or Firm* — Fish & Richardson P.C.

(57) ABSTRACT

The present invention provides new antiviral compounds and pharmacological compositions comprising these new compounds and their use in the prophylaxis, prevention and treatment of viral infections, particularly adenovirus and herpes virus infections.

13 Claims, 5 Drawing Sheets

(56) References Cited

OTHER PUBLICATIONS

Huth et al., "NMR-driven discovery of benzoylanthranilic acid inhibitors of far upstream element binding protein binding to the human oncogene c-myc promoter," *J. Med. Chem.*, 2004, 47:4851-4857.

Izzedine et al., "Antiviral Drug-Induced Nephrotoxicity," *American Journal of Kidney Diseases*, 2005, 45:804-817.

Janner et al., "Fatal adenovirus infection in a child with acquired immunodeficiency syndrome," *Pediatr. Infect. Dis. J.*, 1990, 9:434-436.

Kojaoghlanian et al., "The impact of adenovirus infection on the immunocompromised host," *Rev Med Virol.*, 2003, 13:155-71.

Kumar and Mukerjee, "Condensation of 2-Methyl-3, 1-benzoxazin-4-one with Schiff Bases: Simultaneous introduction of arylidene and amine Moieties," *Indian J. Chem.*, 1982, 21B:24-26.

Lee and Ahn, "Reactions of amides with potassium permanganate in neutral aqueous solution.," *Journal of Organic Chemistry*, 1989, 54:3744-3747.

Leruez-Ville et al., "Description of an adenovirus A31 outbreak in a paediatric haematology unit," *Bone Marrow Transplant*, 2006, 38:23-28.

Mei et al., "Two Closely Related Adenovirus Genome Types with Kidney or Respiratory Tract Tropism Differ in Their Binding to Epithelial Cells of Various Origins," *Virology*, 1998, 240:254-266.

Morfin et al., "In vitro susceptibility of adenovirus to antiviral drugs is species-dependent," *Antiviral Therapy*, 2005, 10:225-229.

Nair et al., "Reaction of anthranilic acid with mesyl chloride," *Indian Journal of Chemistry*, Section B: Organic Chemistry Including Medicinal Chemistry, 1979, 17B:276-277.

Sandberg et al., "Replication-Competent Ad11p Vector (RCAd11p) Efficiently Transduces and Replicates in Hormone-Refractory Metastatic Prostate Cancer Cells," *Human Gene Therapy*, 2009, 20:361-373.

Segerman et al, "There are two different species B adenovirus receptors: sBAR, common to species B1 and B2 adenoviruses, and sB2AR, exclusively used by species B2 adenoviruses," *Journal of Virology*, 2003, 77:1157-1162.

STN International Registry File, RN:905111-57-1, RN:905111-47-9, copyright 2013, 3 pages.

Wadell et al., "Adenoviruses," p. 970-982 in: Murray et al. (eds.), Manual of Clinical Microbiology, 1999, 7th ed. ASM Press.

Wadell, "Molecular epidemiology of human adenoviruses. *Current topics in microbiology and immunology,*" 1984, 110:16 pages.

International Search Report and Written Opinion in International Application No. PCT/SE2011/050724, report completed Sep. 30, 2011, 5 pages.

International Preliminary Report on Patentability in International Application No. PCT/SE2011/050724, issued Dec. 14, 2012, 9 pages.

Adenoviridae, Wikipedia, the free encyclopedia, posted on or before Feb. 5, 2004, retrieved Jul. 24, 2014, http://en.wikipedia.org/wiki/Adenoviridae, 8 pages.

Amide, Wikipedia, the free encyclopedia, posted on or before Aug. 14, 2001, retrieved Jul. 9, 2014, http://en.wikipedia.org/wiki/Amide, 6 pages.

Coxsackievirus, Wikipedia, the free encyclopedia, posted on or before Aug. 22, 2003, retrieved Jul. 24, 2014, http://en.wikipedia.org/wiki/Coxsackievirus, 4 pages.

DNA Virus, Wikipedia, the free encyclopedia, posted on or before Nov. 5, 2001, retrieved Jul. 24, 2014, http://en.wikipedia.org/wiki/DNA__, 17 pages.

Herpes Simplex Virus, Wikipedia, the free encyclopedia, posted on or before Aug. 3, 2002, retrieved Jul. 24, 2014, http://en.wikipedia.org/wiki/Herpes__simplex__virus, 12 pages.

Reduction of Nitro Compounds, Wikipedia, the free encyclopedia, posted on or before Nov. 24, 2006, retrieved Jul. 9, 2014, http://en.wikipedia.org/wiki/Reduction__of__nitro__compounds, 4 pages.

RNA Virus, Wikipedia, the free encyclopedia, posted on or before , retrieved Jul. 24, 2014, http://en.wikipedia.org/wiki/RNA__virus, 9 pages.

Section 12.4: Esters, UC-Davis CHEMWiki, retrieved on Jul. 10, 2014, http://chemwiki.ucdavis.edu/Organic__Chemistry/Organic__Chemistry__With__a__Biological__Emphasis/ Chapter__12%3A__Acyl__substitution__reactions/Section__12.4%3A__Esters, 6 pages.

Trimethylsilyldiazomethane, Wikipedia the free encyclopedia, posted on or before Nov. 10, 2005, retrieved Jul. 24, 2014, http://en.wikipedia.org/wiki/Trimethylsilyldiazomethane , 3 pages.

* cited by examiner

ANTIVIRAL COMPOUNDS

CROSS-REFERENCE TO RELATED APPLICATIONS

This application is a National Stage application under 35 U.S.C. §371 of International Application No. PCT/SE2011/050724, having an International Filing Date of Jun. 13, 2011, which claims the benefit of Swedish Application Serial No. SE1000623-7, filed Jun. 11, 2010 and Swedish Application Serial No. SE1000624-5, filed Jun. 11, 2010. The disclosure of the prior applications are considered part of (and are incorporated by reference in) the disclosure of this application.

FIELD OF THE INVENTION

The present invention relates to new antiviral compounds and pharmacological compositions and their use in the prophylaxis, prevention and treatment of viral infections, particularly adenovirus and herpes virus infections.

BACKGROUND TO THE INVENTION

Adenovirus infections are widespread in society and are occasionally associated with severe, but rarely with life-threatening, disease in otherwise healthy individuals. In contrast, adenovirus infections present a real threat to immunocompromised individuals and can result in disseminated and fatal disease. The number of patients undergoing immunosuppressive therapy for solid organ or hematopoietic stem cell transplantation is steadily increasing, as is the number of AIDS patients, and this makes the problem of adenovirus infections even more urgent to solve. There is no formally approved treatment of adenovirus infections today, and existing antiviral agents evaluated for their anti-adenoviral effect give inconsistent results.

Human adenoviruses are very common pathogens and comprise at least 51 different serotypes; together, these form six different species, A-F. Adenoviruses (Ads) are associated with a wide variety of clinical symptoms in humans, such as upper respiratory illness, acute respiratory disease, gastroenteritis, hemorrhagic cystitis, and even keratoconjunctivitis (Wadell, G. 1984. *Molecular epidemiology of human adenoviruses. Current topics in microbiology and immunology* 110:191-220. Wadell et al. 1999. Adenoviruses, p. 970-982. In. Murray et al. (eds.), *Manual of Clinical Microbiology,* 7th ed. ASM Press.).

These infections can result in severe disease, although an Ad infection is most commonly self-limited in otherwise healthy individuals. The problem is much more pronounced in immunocompromised individuals. This group is steadily growing as a result of increasing numbers of AIDS patients and patients undergoing immunosuppressive therapy for solid organ or hematopoietic stem cell transplantation, and also because of increased survival times of these patients. Immunocompromised individuals are at high risk of developing disseminated disease and multiple organ failure, and an Ad infection can become a serious life-threatening disease (Janney et al. 1990. *Fatal adenovirus infection in a child with acquired immunodeficiency syndrome. Pediatr. Infect. Dis. J.* 9:434-436). In immunocompromised children, Ads are an important cause of disease and case fatality rates of above 50% have been reported (Hierholzer 1992. *Adenoviruses in the immunocompromised host. Clinical Microbiology Reviews* 5:262-274). In pediatric bone marrow transplant (BMT) recipients the incidence of Ad infection is substantially higher than in adult BMT recipients (Baldwin et al. 2000. *Outcome and clinical course of* 100 *patients with adenovirus infection following bone marrow transplantation. Bone Marrow Transplantation* 26:1333-1338).

A number of different Ads have been isolated from immunocompromised patients, most frequently from species A, B, or C (Kojaoghlanian et al. 2003. *The impact of adenovirus infection on the immunocompromised host. Rev Med Virol* 13:155-71). Species B serotypes are predominantly associated with renal syndromes and species C serotypes are usually associated with hepatitis. In recent years, infections with Ad serotype 31 (species A) have been increasingly reported and they often occur in patients with infections involving multiple Ad serotypes, occasionally with lethal outcome (Leruez-Ville et al. 2006. *Description of an adenovirus A*31 *outbreak in a paediatric haematology unit. Bone Marrow Transplant* 38:23-28.).

There are no approved specific antiviral compounds for treatment of Ad infections available today. Established antiviral drugs including cidofovir, ribavirin, and ganciclovir have been tested for anti-adenoviral activity both in in vitro experiments and in the clinical setting. The clinical efficacy is inconclusive, since varying results have been reported for the drugs. Of the approved drugs, Cidofovir appears to be most effective against Ads (Morfin et al. 2005. *In vitro susceptibility of adenovirus to antiviral drugs is species-dependent. Antiviral Therapy* 10:225-229). However, cidofovir is associated with nephrotoxicity and acute renal failure (Izzedine et al. 2005. *Antiviral Drug-Induced Nephrotoxicity. American Journal of Kidney Diseases* 45:804-817). The need for new anti-adenoviral substances is clearly increasing due to the large number of immuno-compromised patients undergoing transplantations, and also patients suffering from AIDS or with genetic immunodeficiencies.

Herpes viruses are divided into alpha, beta and gamma herpes viruses. All studied herpes viruses enter a latent state after the primary infection. This means that they later in life can be activated and cause morbidity and in immunocompromized persons even mortality. Herpes simplex virus (HSV)1 & 2 and varicellae virus are the members of alpha herpes viruses. The U-L 23 gene of HSV encodes a nucleoside kinase also called thymidine kinase. This gene product is targeted by acyclovir and its derivatives. This is an effective therapeutic drug against HSV 1 & 2 and it has also been used against varicella-zoster (VZ) infections in adults and immunocompromized children and adults. There is however a need for new alternative antiviral drugs that can be used on acyclovir resistant strains and viruses that do not express a thymidine kinase.

Screening of large compound collections with purified protein or whole cell-based assays, i.e. high-throughput screening (HTS), is a common method to identify biologically active compounds. Cell-based approaches are commonly more labor-intensive but have the benefit of a wider screening without the limitation of having a preconceived idea of the mechanism of action. We have developed a unique whole-cell reporter gene assay based on a GFP-expressing replication-competent Ad vector (Sandberg et al. 2009. *Replication-Competent Ad*11*p Vector* (*RCAd*11*p*) *Efficiently Transduces and Replicates in Hormone-Refractory Metastatic Prostate Cancer Cells. Human Gene Therapy* 20:361-373). The assay can identify compounds that directly or indirectly affect adenoviral protein expression. This assay was used to screen approximately 9,800 compounds, resulting in a number of compounds that have an inhibitory effect on Ads without killing the host cells. The inhibitory effect was ascertained at four different stages of the viral replication cycle. Here, we describe the screening method and report on a novel inhibitors of Ad replication that is effective on Ad types representing the six species of human adenoviruses as well as on Herpes simplex virus 1 (HSV-1).

US 2006/0035245 describes a method for identifying anti-HIV agents comprising i) determining the effect of the agent on the activity of Tn5 transponase, and ii) determining if the agent can inhibit HIV integrase. The compound 2-[[2-(Benzoylamino)benzoyl]amino]-benzoic acid (herein referred to as compound A02) was found to inhibit Tn5 transponase, but failed to inhibit HIV integrase.

DESCRIPTION OF THE INVENTION

In one embodiment the present invention provides pharmaceutical compositions comprising a compound of the general formula (I), (II) or (III) and pharmaceutical acceptable salts thereof:

Formula (I)

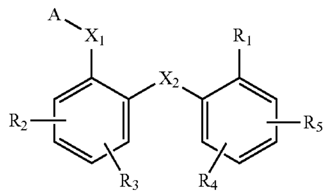

Formula (II)

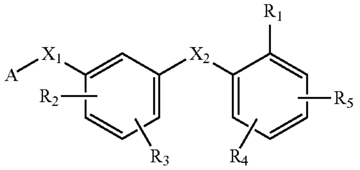

Formula (III)

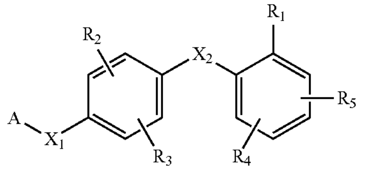

wherein $X_1$ is selected from —CO—NH—, —CO—NH—$CH_2$—, —$SO_2$—NH—, $SO_2$—, —NH—, $X_2$ is selected from —CO—NH—, —$CH_2$—CO—NH, —CO—NH—$CH_2$—, —$SO_2$—NH—, A is selected from the group consisting of, hydrogen, —$C_{1-8}$alkyl, —$C_{2-8}$alkenyl, —$C_{2-8}$alkynyl, —$(CH_2)_n$$C_{3-7}$cycloalkyl, —$(CH_2)_n$$C_{2-9}$heterocycloalkyl, —$(CH_2)_n$phenyl, —$(CH_2)_n$ naphthyl, —$(CH_2)_n$aryl, —$(CH_2)_n$heteroaryl, —$(CH_2)_n$$NR_6R_6$, —$(CH2)_n$$N(R_6)CO_2C_{1-8}$alkyl, —$(CH_2)_n$ $CO_2H$, —$(CH_2)_n$$CO_2C_{1-8}$alkyl, wherein alkyl, alkenyl, alkynyl, cycloalkyl, heterocycloalkyl, aryl, phenyl, naphthyl, heteroaryl, and ($CH_2$) are unsubstituted or substituted with one to three substituents independently selected from halogen, oxo, nitro, hydroxy, —$NR_6R_6$, —CN, —$CF_3$, —$OCF_3$, —$C_{1-6}$alkyl, —$C_{2-6}$ alkenyl, —$C_{2-6}$ alkynyl, —$C_{1-6}$ alkyloxy;

$R_1$ is selected from hydrogen, halogen, nitro, hydroxy, —$CO_2H$, —$CO_2C_{1-4}$alkyl, —$C_{1-6}$alkyl, —$C_{2-6}$ alkenyl, —$C_{2-6}$ alkynyl, —$C_{1-6}$ alkyloxy, —CN, —$CF_3$, —$OCF_3$, tetrazol-5-yl, $CONR_6R_6$;

$R_2$, $R_3$, $R_4$ and $R_5$ are each independently selected from hydrogen, halogen, oxo, nitro, hydroxy, —$NR_6R_6$, —CN, —$CF_3$, —$OCF_3$, —$C_{1-6}$ alkyl, —$C_{2-6}$ alkenyl, —$C_{2-6}$ alkynyl, —$C_{1-6}$ alkyloxy;

each $R_6$ is independently selected from the group consisting of hydrogen, —$C_{1-8}$alkyl, —$C_{2-8}$alkenyl, —$C_{2-8}$alkynyl, —$(CH_2)_n$$CO_2H$; and n is 0, 1, 2, 3, 4, or 5;

for the use in the prophylaxis, prevention and/or treatment of viral diseases.

Preferably one of $X_1$ and $X_2$ is —CO—NH—.

Preferably both $X_1$ and $X_2$ are —CO—NH—.

Preferably A is selected from phenyl, naphthyl, and heteroaryl, unsubstituted or substituted with one to three substituents independently selected from halogen, oxo, nitro, hydroxy, —$NR_6R_6$, —CN, —$CF_3$, —$OCF_3$, —$C_{1-6}$alkyl, —$C_{2-6}$ alkenyl, —$C_{2-6}$ alkynyl, —$C_{1-6}$ alkyloxy;

Preferably $R_1$ is selected from —$CO_2H$, and —$CO_2$ $C_{1-4}$alkyl.

Preferred compounds are

2-[[2-(Benzoylamino)benzoyl]amino]-benzoic acid—Compound A02

2-[[2-(4-Methyl-benzoylamino)benzoyl]amino]-benzoic acid—Compound 12c

2-[[3-(Benzoylamino)benzoyl]amino]-benzamide—Compound 12d

2-[[3-(2-Methyl-benzoylamino)benzoyl]amino]-benzoic acid—Compound 12e

2-[[2-(4-Methoxy-benzoylamino)benzoyl]amino]-benzoic acid—Compound 12f

4-Methyl-N-{2-[(2-methylphenyl)carbamoyl]phenyl}-benzamide—Compound 12g

Ethyl 2-[3-(benzoylamino)benzoylamino]benzoate—Compound 7c

2-[[3-(Benzoylamino)benzoyl]amino]benzoic acid—Compound 8c

Ethyl 2-[4-(benzoylamino)benzoylamino]benzoate—Compound 7d

2-[[4-(Benzoylamino)benzoyl]amino]benzoic acid—Compound 8d

2-Benzoylamino-N-phenyl-benzamide—Compound 11

2-[2-(Acetylamino)benzoylamino]benzoic acid—Compound 17a

2-[2-(Methanesulfonylamino)benzoylamino]benzoic acid—Compound 17b

2-[2-(p-Toluenesulfonylamino)benzoylamino]benzoic acid—Compound 17c

2-[2-(Trimethylacetylamino)benzoylamino]benzoic acid—Compound 17d

2-[[2-(Cyclohexanecarboxylamino)benzoyl]amino]benzoic acid—Compound 17e

2-[2-(4-Carboxybutanoylamido)benzoyl]aminobenzoic acid—Compound 17f

2-[2-(Benzylamino)benzoylamino]benzoic acid—Compound 17g

2-[2-(2-Fluorobenzoylamino)-benzoylamino]benzoic acid—Compound 17h

2-[2-(3-Fluorobenzoylamino)-benzoylamino]benzoic acid—Compound 17i

2-[2-(4-Fluorobenzoylamino)-benzoylamino]benzoic acid—Compound 17j

2-[2-(Phenylacetylamino)benzoylamino]benzoic acid—Compound 17k

Ethyl 2-[2-(benzoylamino)benzoylamino]benzoate—Compound 23a

Ethyl 2-[2-(acetylamino)benzoylamino]benzoate—Compound 22a

Ethyl 2-[2-(trimethylacetylamino)benzoylamino]benzoate—Compound 24a

Ethyl 2-[[2-(cyclohexanecarboxylamino)benzoyl]amino] benzoate—Compound 25a

Ethyl 2-[2-(phenylacetylamino)benzoylamino]benzoate—Compound 26a

Ethyl 2-[2-(4-carboxybutanoylamido)benzoyl]aminobenzoate—Compound 27a

Ethyl 2-[2-(methanesulfonylamino)benzoylamino]benzoate—Compound 29a

Ethyl 2-[2-(p-toluenesulfonylamino)benzoylamino]benzoate—Compound 30a

Ethyl 2-[[2-(benzylamino)benzoyl]amino]benzoate—Compound 40a

2-[[2-(Benzoylamino)benzoyl]amino]benzoic acid—Compound 23b

2-[2-(Acetylamino)benzoylamino]benzoic acid—Compound 22b

2-[2-(Trimethylacetylamino)benzoylamino]benzoic acid—Compound 24b

2-[[2-(Cyclohexanecarboxylamino)benzoyl]amino]benzoic acid—Compound 25b

2-[2-(Phenylacetylamino)benzoylamino]benzoic acid—Compound 26b

2-[2-(4-Carboxybutanoylamido)benzoyl]aminobenzoic acid—Compound 27b

2-[2-(Methanesulfonylamino)benzoylamino]benzoic acid—Compound 29b

2-[2-(p-Toluenesulfonylamino)benzoylamino]benzoic acid—Compound 30b

2-[2-(Benzylamino)benzoylamino]benzoic acid—Compound 40b

2-[2-(benzoylamino)benzoylamino]phenylacetic acid—Compound 23

2-[2-(benzoylamino)phenylacetylamino]benzoic acid—Compound 28

2-[2-(2-fluorobenzoylamino)-benzoylamino]-4-chlorobenzoic acid—Compound 35a

2-[2-(2-fluorobenzoylamino)benzoylamino]-5-chlorobenzoic acid—Compound 35b

2-[2-(2-fluorobenzoylamino)-benzoylamino]-4-methoxybenzoic acid—Compound 35c

2-[2-(2-fluorobenzoylamino)-benzoylamino]-5-methoxybenzoic acid—Compound 35d

2-[2-(2-fluorobenzoylamino)-benzoylamino]-4,5-difluorobenzoic acid—Compound 35e

2-[4-chloro-2-(2-fluorobenzoylamino)-benzoylamino]benzoic acid—Compound 35f

2-[5-chloro-2-(2-fluorobenzoylamino)-benzoylamino]benzoic acid—Compound 35g

2-[4-methoxy-2-(2-fluorobenzoylamino)-benzoylamino]benzoic acid—Compound 35h

2-[5-methoxy-2-(2-fluorobenzoylamino)-benzoylamino]benzoic acid—Compound 35i

2-[4,5-difluoro-2-(2-fluorobenzoylamino)-benzoylamino]benzoic acid—Compound 35j

The viral disease can be selected from infections caused by RNA virus and/or DNA virus. Preferably the viral disease is an infection caused by DNA virus.

The viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections. Togavirus infections including Rubivirus infections. Retrovirus infections including lentivirus infections, such as HIV infections.

Preferably the viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections. Togavirus infections including Rubivirus infections.

More preferably the viral disease is an Adenovirus infection, a Herpes virus infection or a Picornavirus infection. The herpes virus infections can be caused by HSV-1, HSV-2 and/or varicella zoster virus.

Most preferably the viral disease is an infection caused by an Adenovirus.

In another embodiment the present invention provides new compounds of the general formula (I), (II) or (III) and pharmaceutical acceptable salts thereof:

Formula (I)

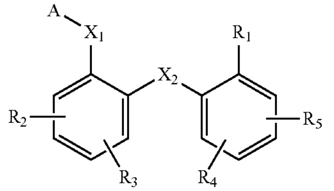

Formula (II)

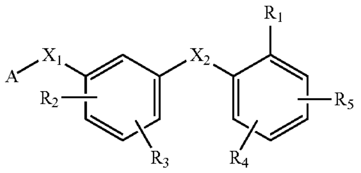

Formula (III)

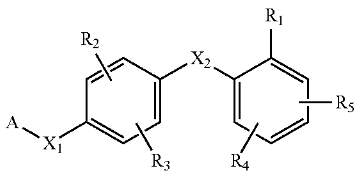

wherein $X_1$ is selected from —CO—NH—, —CO—NH—$CH_2$—, —$SO_2$—NH—, $SO_2$—, —NH—, $X_2$ is selected from —CO—NH—, —$CH_2$—CO—NH, —CO—NH—$CH_2$—, —$SO_2$—NH—, A is selected from the group consisting of, hydrogen, —$C_{1-8}$alkyl, —$C_{2-8}$alkenyl, —$C_{2-8}$alkynyl, —$(CH_2)_n C_{3-7}$cycloalkyl, —$(CH_2)_n C_{2-9}$heterocycloalkyl, —$(CH_2)_n$phenyl, $(CH_2)_n$ naphthyl, —$(CH_2)_n$aryl, —$(CH_2)_n$heteroaryl, —$(CH_2)_n NR_6R_6$, —$(CH_2)_n NR_6R_6CO_2C_{1-8}$alkyl, —$(CH_2)_n$ $CO_2H$, —$(CH_2)_n CO_2C_{1-8}$alkyl, wherein alkyl, alkenyl, alkynyl, cycloalkyl, heterocycloalkyl, aryl, phenyl, naphthyl, heteroaryl, and ($CH_2$) are unsubstituted or substituted with one to three substituents independently selected from halogen, oxo, nitro, hydroxy, —$NR_6R_6$, —CN, —$CF_3$, —$OCF_3$, —$C_{1-6}$alkyl, —$C_{2-6}$ alkenyl, —$C_{2-6}$ alkynyl, —$C_{1-6}$ alkyloxy;

$R_1$ is selected from hydrogen, halogen, nitro, hydroxy, —$CO_2H$, —$CO_2C_{1-4}$alkyl, —$C_{1-6}$alkyl, —$C_{2-6}$ alkenyl, —$C_{2-6}$ alkynyl, —$C_{1-6}$ alkyloxy, —CN, —$CF_3$, —$OCF_3$, tetrazol-5-yl, —$CONR_6R_6$;

$R_2$, $R_3$, $R_4$ and $R_5$ are each independently selected from hydrogen, halogen, oxo, nitro, hydroxy, —$NR_6R_6$, —CN, —$CF_3$, —$OCF_3$, —$C_{1-6}$ alkyl, —$C_{2-6}$ alkenyl, —$C_{2-6}$ alkynyl, —$C_{1-6}$ alkyloxy, each $R_6$ is independently selected from the group consisting of hydrogen, —$C_{1-8}$alkyl, —$C_{2-8}$alkenyl, —$C_{2-8}$alkynyl, —$(CH_2)_nCO_2H$; and n is 0, 1, 2, 3, 4, or 5;

further provided that when $X_1$ and $X_2$ are —CO—NH— and $R_1$ is —COOH then A is not phenyl, 3-methylphenyl-, 4-methylphenyl, or 4-methoxyphenyl-, and when $X_1$ and $X_2$ are —CO—NH— and $R_1$ is methyl then A is not 3-methylphenyl.

Preferably both $X_1$ and $X_2$ are —CO—NH—.

Preferably A is selected from phenyl, naphthyl, and heteroaryl, unsubstituted or substituted with one to three substituents independently selected from halogen, oxo, nitro, hydroxy, —$N(R_6)_2$, —CN, —$CF_3$, —$OCF_3$, —$C_{1-6}$alkyl, —$C_{2-6}$ alkenyl, —$C_{2-6}$ alkynyl, —$C_{1-6}$ alkyloxy;

Preferably $R_1$ is selected from —$CO_2H$, —$CO_2C_{1-4}$alkyl,

Most preferably the compounds are selected from the group consisting of:

Ethyl 2-[3-(benzoylamino)benzoylamino]benzoate—Compound 7c
2-[[3-(Benzoylamino)benzoyl]amino]benzoic acid—Compound 8c
Ethyl 2-[4-(benzoylamino)benzoylamino]benzoate—Compound 7d
2-[[4-(Benzoylamino)benzoyl]amino]benzoic acid—Compound 8d
2-Benzoylamino-N-phenyl-benzamide—Compound 11
2-[2-(Acetylamino)benzoylamino]benzoic acid—Compound 17a
2-[2-(Methanesulfonylamino)benzoylamino]benzoic acid—Compound 17b
2-[2-(p-Toluenesulfonylamino)benzoylamino]benzoic acid—Compound 17c
2-[2-(Trimethylacetylamino)benzoylamino]benzoic acid—Compound 17d
2-[[2-(Cyclohexanecarboxylamino)benzoyl]amino]benzoic acid—Compound 17e
2-[2-(4-Carboxybutanoylamido)benzoyl]aminobenzoic acid—Compound 17f
2-[2-(Benzylamino)benzoylamino]benzoic acid—Compound 17g
2-[2-(2-Fluorobenzoylamino)-benzoylamino]benzoic acid—Compound 17h
2-[2-(3-Fluorobenzoylamino)-benzoylamino]benzoic acid—Compound 17i
2-[2-(4-Fluorobenzoylamino)-benzoylamino]benzoic acid—Compound 17j
2-[2-(Phenylacetylamino)benzoylamino]benzoic acid—Compound 17k
Ethyl 2-[2-(benzoylamino)benzoylamino]benzoate—Compound 23a
Ethyl 2-[2-(acetylamino)benzoylamino]benzoate—Compound 22a
Ethyl 2-[2-(trimethylacetylamino)benzoylamino]benzoate—Compound 24a
Ethyl 2-[[2-(cyclohexanecarboxylamino)benzoyl]amino]benzoate—Compound 25a
Ethyl 2-[2-(phenylacetylamino)benzoylamino]benzoate—Compound 26a
Ethyl 2-[2-(4-carboxybutanoylamido)benzoyl]aminobenzoate—Compound 27a
Ethyl 2-[2-(methanesulfonylamino)benzoylamino]benzoate—Compound 29a
Ethyl 2-[2-(p-toluenesulfonylamino)benzoylamino]benzoate—Compound 30a
Ethyl 2-[[2-(benzylamino)benzoyl]amino]benzoate—Compound 40a
2-[[2-(Benzoylamino)benzoyl]amino]benzoic acid—Compound 23b
2-[2-(Acetylamino)benzoylamino]benzoic acid—Compound 22b
2-[2-(Trimethylacetylamino)benzoylamino]benzoic acid—Compound 24b
2-[[2-(Cyclohexanecarboxylamino)benzoyl]amino]benzoic acid—Compound 25b
2-[2-(Phenylacetylamino)benzoylamino]benzoic acid—Compound 26b
2-[2-(4-Carboxybutanoylamido)benzoyl]aminobenzoic acid—Compound 27b
2-[2-(Methanesulfonylamino)benzoylamino]benzoic acid—Compound 29b
2-[2-(p-Toluenesulfonylamino)benzoylamino]benzoic acid—Compound 30b
2-[2-(Benzylamino)benzoylamino]benzoic acid—Compound 40b
2-[2-(benzoylamino)benzoylamino]phenylacetic acid—Compound 23
2-[2-(benzoylamino)phenylacetylamino]benzoic acid—Compound 28
2-[2-(2-fluorobenzoylamino)-benzoylamino]-4-chlorobenzoic acid—Compound 35a
2-[2-(2-fluorobenzoylamino)benzoylamino]-5-chlorobenzoic acid—Compound 35b
2-[2-(2-fluorobenzoylamino)-benzoylamino]-4-methoxybenzoic acid—Compound 35c
2-[2-(2-fluorobenzoylamino)-benzoylamino]-5-methoxybenzoic acid—Compound 35d
2-[2-(2-fluorobenzoylamino)-benzoylamino]-4,5-difluorobenzoic acid—Compound 35e
2-[4-chloro-2-(2-fluorobenzoylamino)-benzoylamino]benzoic acid—Compound 35f
2-[5-chloro-2-(2-fluorobenzoylamino)-benzoylamino]benzoic acid—Compound 35g
2-[4-methoxy-2-(2-fluorobenzoylamino)-benzoylamino]benzoic acid—Compound 35h
2-[5-methoxy-2-(2-fluorobenzoylamino)-benzoylamino]benzoic acid—Compound 35i
2-[4,5-difluoro-2-(2-fluorobenzoylamino)-benzoylamino]benzoic acid—Compound 35j.

In another embodiment the present invention provides pharmaceutical compositions comprising a compound according to the invention.

In another embodiment the present invention provides pharmaceutical compositions comprising a compound according to the invention for the use in the prophylaxis, prevention and/or treatment of viral diseases.

The viral disease can be selected from infections caused by RNA virus and DNA virus. Preferably the viral disease is an infection caused by DNA virus.

The viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Togavirus infections including Rubivirus infections. Retrovirus infections including lentivirus infections, such as HIV infections, Preferably the viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Togavirus infections including Rubivirus infections.

More preferably the viral disease is an Adenovirus infection, a Herpes virus infection or a Picornavirus infection. The herpes virus infections can be caused by HSV-1, HSV-2 and/or varicella zoster virus.

Most preferably the viral disease is an infection caused by an Adenovirus.

In another embodiment the present invention provides methods for the prophylaxis, prevention and/or treatment of a viral disease, the methods comprising administering a compound according to the invention to a subject in need of such treatment.

The viral disease can be selected from infections caused by RNA virus and DNA virus. Preferably the viral disease is an infection caused by DNA virus.

The viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Togavirus infections including Rubivirus infections. Retrovirus infections including lentivirus infections, such as HIV infections, Preferably the viral disease can be selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Togavirus infections including Rubivirus infections.

More preferably the viral disease is an Adenovirus infection, a Herpes virus infection or a Picornavirus infection. The herpes virus infections can be caused by HSV-1, HSV-2 and/or varicella zoster virus.

Most preferably the viral disease is an infection caused by an Adenovirus.

DEFINITIONS

Figure 1:
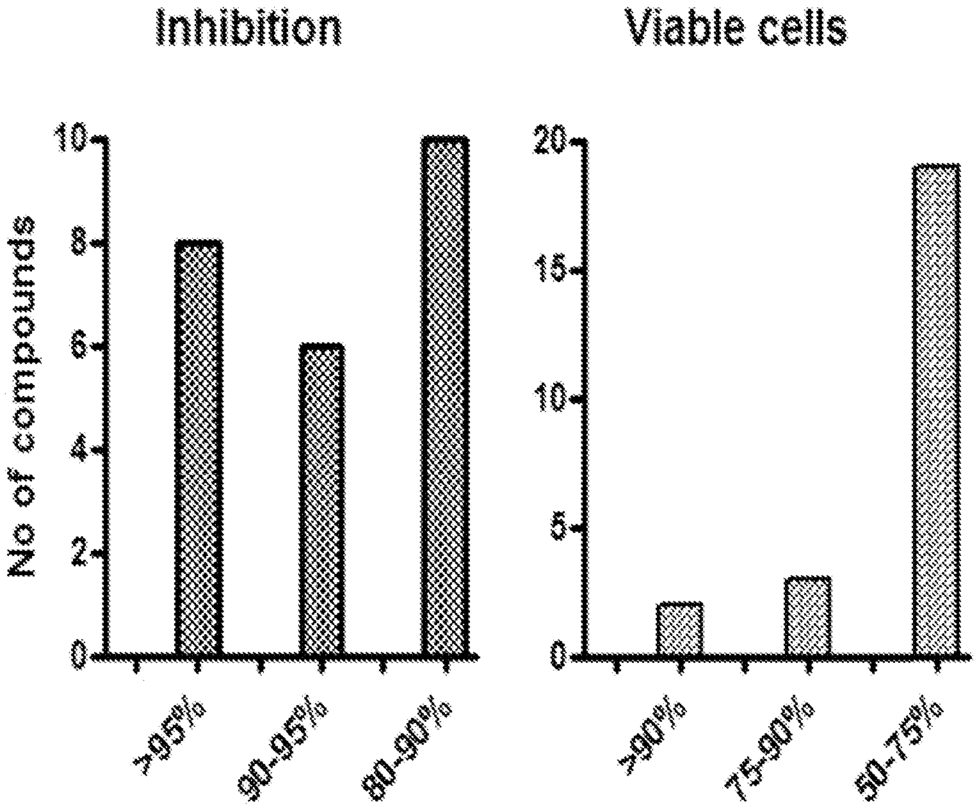
FIG. 1. Distribution of the inhibitory effect and the toxicity of the 24 compounds verified as Ad inhibitors at 25 μM.

As used herein, alkyl means an alkyl group being straight or branched. By —$C_{1-8}$alkyl is meant an alkyl group having from 1 to 8 carbon atoms. Examples include methyl, ethyl, propyl, isopropyl, butyl, hexyl, heptyl, octyl, and the like. The alkyl groups may be unsubstituted or substituted.

As used herein, alkyloxy means an alkyloxy group being straight or branched. By —$C_{1-6}$ alkyloxy is meant an alkyloxy group having from 1 to 6 carbon atoms. Examples include methoxy, ethoxy, propoxy, isopropoxy, butoxy, hexoxy, and the like. The alkoxy groups may be unsubstituted or substituted.

As used herein, alkenyl means an alkenyl group being straight or branched. By —$C_{2-8}$ alkenyl is meant an alkenyl group having from 2 to 8 carbon atoms. Examples include ethenyl, propenyl, isopropenyl, butenyl, hexenyl, heptyl, heptenyl, octenyl, and the like. The alkenyl groups may be unsubstituted or substituted.

As used herein, alkynyl means an alkynyl group being straight or branched. By —$C_{2-8}$ alkynyl is meant an alkynyl group having from 2 to 8 carbon atoms. Examples include ethynyl, propynyl, butynyl, hexynyl, heptynyl, octynyl, and the like. The alkynyl groups may be unsubstituted or substituted.

As used herein, $C_{3-7}$cycloalkyl means a cycloalkyl having from 3 to 7 carbon atoms. Examples include cyclopropyl, cyclobutyl, cyclopentyl, cyclohexyl, cycloheptyl, and the like. The cycloalkyl groups may be unsubstituted or substituted.

The aryl moieties described here, either alone or with various substituents, contain from 6 to 15 carbon atoms and include phenyl, 1-naphthalenyl and 2-naphthalenyl.

The heteroaryl moieties described here, either alone or with various substituents, contain from 3 to 15 carbon atoms and include furans, thiophenes, indoles, furyl, pyridyl, thienyl, tryptophane and the like.

As used herein, the term "halogen" denotes a fluoro, chloro, bromo, or iodo group.

The term tetrazol-5-yl includes 1H-tetrazol-5-yl, 2H-tetrazol-5-yl, and 5H-tetrazol-5-yl.

As used herein, when two or more groups are used in connection with each other, it means that each group is substituted by the immediately preceding group. For instance, trifluoromethylphenyl means a phenyl group substituted by a trifluoromethyl group.

As used herein, the terms prevent or prevention and prophylaxis are given their ordinary meaning and thus means the avoidance or alleviation of the serious consequences of a disease or a side-effect by early detection.

As used herein, the term "mammal" means a human or an animal such as monkeys, primates, dogs, cats, horses, cows, etc.

As used herein, the single enantiomers, racemic mixtures and unequal mixtures of two enantiomers are within the scope of the invention, where such isomers exist. It should be understood that all the diastereomeric forms possible (pure enantiomers, racemic mixtures and unequal mixtures of two or more diastereomers), tautomers, and atropisomers are within the scope of the invention.

As used herein, the term "pharmaceutically acceptable salts" includes acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion using a suitable ion exchange resin.

Suitable acids are non-toxic and include e g, but are not limited to, hydrochloric acid, hydrobromic acid, hydroiodic acid, sulphuric acid, nitric acid, acetic acid, citric acid, ascorbic acid, lactic acid, malic acid, and tartaric acid. Suitable bases are non-toxic and include e g, but are not limited to, sodium hydroxide, potassium hydroxide, lithium hydroxide, ammonia, methylamine, dimethylamine, trimethylamine, and triethylamine.

In the context of the present specification, the term "treatment" also includes "prophylaxis" unless there are specific indications to the contrary. The term "treatment" within the context of the present invention further encompasses to administer an effective amount of a compound of the present invention, to mitigate either a pre-existing disease state, acute or chronic, or a recurring condition. This definition also encompasses prophylactic therapies for prevention of recurring condition and continued therapy for chronic disorders.

The compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the present invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of the present invention, inert, pharmaceutically acceptable carriers can be either solid or liquid. Solid form preparations include powders, tablets, dispersable granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

In powders, the carrier is a finely divided solid, which is in mixture with the finely divided compound of the present invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogenous mixture is then poured into conveniently sized moulds and allowed to cool and solidify.

Suitable carriers are magnesium carbonate, magnesium stearate, talc, lactose, sugar, pectin, dextrin, starch, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

The above-mentioned subject-matter for a pharmaceutical composition comprising a compound according to the present invention is applied analogously for a pharmaceutical composition comprising a combination according to the present invention.

Another object of the present invention is a compound as disclosed above for use in medicine.

Another object of the present invention is a pharmaceutical formulation comprising a compound as disclosed above in admixture with pharmaceutically acceptable adjuvants, diluents and/or carriers.

EXAMPLES

Example 1

Screening for Inhibition of Viral Replication

Viruses and Vector

The RCAd11pGFP vector used in this study is a replication-competent Ad vector (Sandberg et al. 2009. *Replication-Competent Ad*11*p Vector* (*RCAd*11*p*) *Efficiently Transduces and Replicates in Hormone-Refractory Metastatic Prostate Cancer Cells. Human Gene Therapy* 20:361-373). Ads used in this study were Ad5 (strain F2853-5b), Ad11p (p=prototype, strain Slobitski), Ad4 (strain RI-67), Ad31 (strain 1315/63), Ad37 (strain 1477), and Ad41 (strain Tak). The viruses were propagated in A549 cells and purified on a discontinuous CsCl gradient as described previously (Mei et al. 1998. *Two Closely Related Adenovirus Genome Types with Kidney or Respiratory Tract Tropism Differ in Their Binding to Epithelial Cells of Various Origins. Virology* 240:254-266). The virion band was collected and density was measured on a refractometer. Virions were desalted on a NAP-10 column (GE healthcare, Buckinghamshire, UK) and eluted with 1.5 ml 10 mM PBS. Virion concentration was determined by spectrophotometry; 1 OD unit ($OD_{260}$-$OD_{330}$) corresponds to 280 μg virions or $10^{12}$ virus particles/ml. The identity of the adenovirus types was assessed according to their DNA restriction patterns.

Cell Lines

A549 cells (oat cell carcinoma from the human lung; alveolar basal epithelial cells) were grown in Dulbecco's modified Eagle's medium (DMEM) (Sigma-Aldrich, St. Louis, Mo.) containing 0.75 g/l $NaHCO_3$, 20 mM HEPES (EuroClone, Milan, Italy), penicillin G (100 IU/ml) and streptomycin sulfate (100 μg/ml) combined (1×PEST) (Gibco, Carlsbad, Calif.), and 5% fetal bovine serum (FBS) (Gibco) at 37° C. K562 is a non-adherent human erythroleukemia cell line. FSU (Foreskin Umeå) is a diploid fibroblast cell line. K562 and FSU cells were cultured in RPMI 1640 (Sigma-Aldrich) supplemented with 0.75 g/l $NaHCO_3$, 20 mM HEPES (EuroClone), 1×PEST (Gibco) and 5% fetal bovine serum (FBS) (Gibco) at 37° C.

Compounds

The compound collection screened was supplied ChemBridge (San Diego, Calif.) and consisted of 9,800 low molecular weight organic compounds. The compounds were dissolved in DMSO in 5 mM stock solutions and stored in 96-well plates sealed with heat-sealing films at room temperature in the dark in a controlled dry atmosphere. Compounds were analyzed by combined liquid chromatography mass spectrometry (LC-MS) using a Waters HPLC system equipped with an XTerra® MS $C_{18}$ 5 μm 4.6-×50-mm column and an $H_2O$/acetonitrile/formic acid eluent system using UV analysis was carried out at 212 nm and mass spectra were recorded by detecting negative ($ES^-$) molecular ions with an electro-spray Waters Micromass ZG 2000 instrument. The same LC-MS system was also used for purification with a preparative XTerra® Prep MS $C_{18}$ 5 μm 19-×50-mm column and an $H_2O$/acetonitrile eluent system. $^1H$ and $^{13}C$ NMR spectra were recorded in DMSO-$d_6$ (residual DMSO-$d_5$, $\delta_H$=2.50 ppm and DMSO-$d_6$ $\delta_C$=39.51 ppm as internal standards) using a Bruker DRX-400 spectrometer.

Screening.

The screening assay is based on GFP expression from the RCAd11pGFP vector in a K562 cell system. The 9,800 compounds were screened for their ability to inhibit emitted fluorescence and hence expression of the adenoviral genome. To be considered as a potential hit, the compound had to decrease the intensity of fluorescence by more than 80% and kill no more than 50% of the cells. The primary hits of the screening procedure were 408 distinct compounds that showed properties of inhibition of RCAd11pGFP expression in K562 cells, representing a hit rate of around 4%. None of the compounds selected for further study were autofluorescent.

Validation of Hits.

Figure 2:
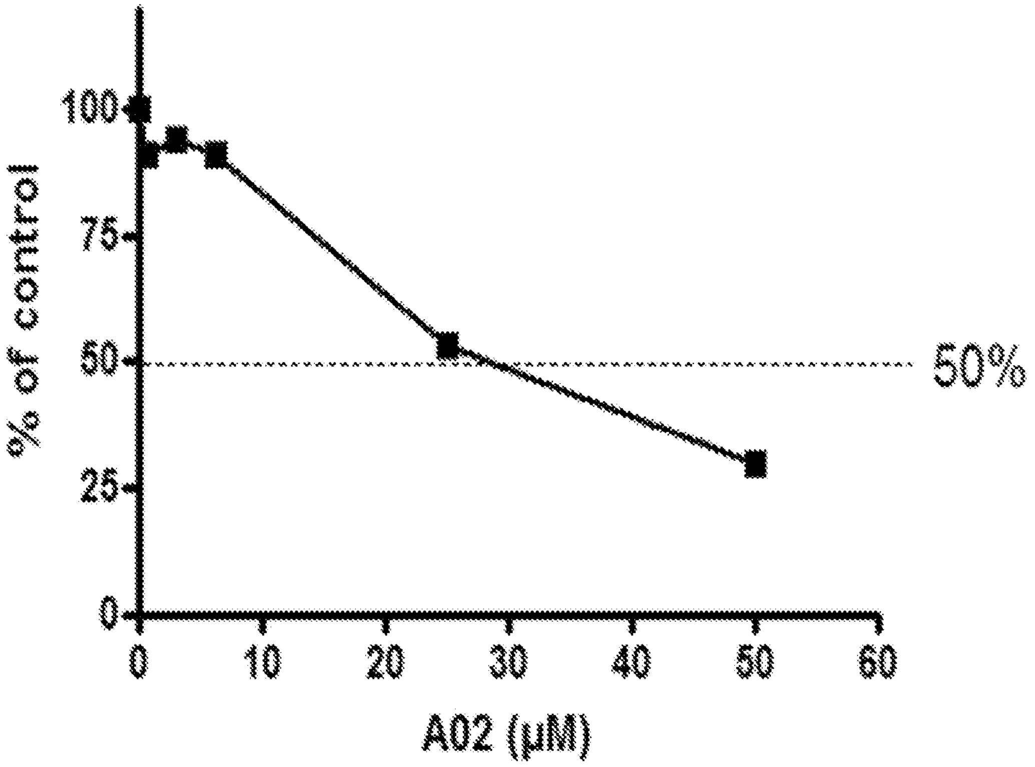
FIG. 2. Dose-response for A02 inhibition of GFP expression from the RCAd11pGFP vector in K562 cells. Fluorescence intensity was measured after 24 h incubation with compound A02 and vector.

To verify the hits and to exclude false positives, the compounds were serially diluted in 7 steps for dose-response analysis using the screening assay. Compounds that exhibited at least 40% inhibition of fluorescence intensity at 25 μM or that had very low toxicity were considered verified hits. Twenty-four compounds met these criteria. The distribution of fluorescence inhibition and cellular toxicity detected in the screening process of these 24 hits is summarized in FIG. 1. One of the most efficient and least toxic compounds was A02, 2-[[2-(benzoylamino)benzoyl]amino]-benzoic acid. This compound was evaluated further as a potential drug candidate. Serial dilution of compound A02 in the screening setup with RCAd11pGFP in K562 cells showed a clear dose response, with a 50% inhibitory concentration ($IC_{50}$) of 28.6 μM (FIG. 2).

In the process of verifying the identity of the inhibitory compounds, combined analysis by liquid chromatography and mass spectrometry of the purchased compounds was performed. It turned out that the A02 solution in fact contained three different molecules. The three components were separated by liquid chromatography and their structures were confirmed by mass spectrometry and NMR spectroscopy.

Compound A01

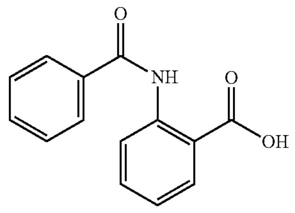 [SMILES: O=C(Nc1ccccc1C(=O)O)c1ccccc1]

For compound A01, the data were in agreement with those published (Lee and Ahn 1989. *Reactions of amides with potassium permanganate in neutral aqueous solution. Journal of Organic Chemistry* 54:3744-3747).

Compound A02

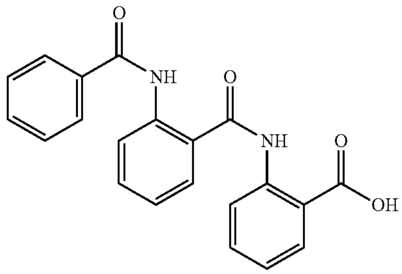 [SMILES: O=C(Nc1ccccc1C(=O)Nc1ccccc1C(=O)O)c1ccccc1]

Analytical data for compound A02. $^1$H NMR (400 MHz, DMSO-$d_6$): δ 7.25 (t, J=7.4 Hz, 1H), 7.37 (t, J=7.4 Hz, 1H), 7.60-7.71 (m, 5H), 7.97-8.01 (m, 3H), 8.07 (dd, J=1.4 Hz, 7.8 Hz, 1H), 8.53 (d, J=8.1 Hz, 1H), 8.60 (d, J=8.3 Hz, 1H), 11.87 (s, 1H), 12.75 (br s, 1H), 13.80 (br s, 1H); $^{13}$C (100 MHz, DMSO-$d_6$): δ 117.8, 120.8, 121.9, 123.0, 123.5, 123.8, 127.1, 127.9, 128.9, 131.2, 132.0, 132.7, 134.1, 134.5, 139.0, 140.3, 164.8, 167.0, 169.8. LCMS (m/z): $[M-H^+]^-$ calcd for $[C_{21}H_{15}N_2O_4]$, 359.10. found, 359.48.

Compound A03

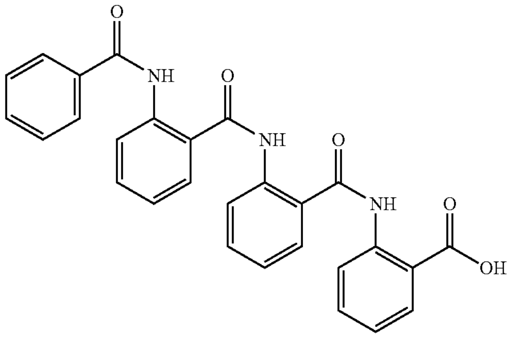 [SMILES: O=C(Nc1ccccc1C(=O)Nc1ccccc1C(=O)Nc1ccccc1C(=O)O)c1ccccc1]

Analytical data for compound A03. $^1$H NMR (400 MHz, DMSO-$d_6$): δ 7.21 (t, J=7.5 Hz, 1H), 7.34-7.43 (m, 2H), 7.50-7.54 (m, 2H), 7.59-7.62 (m, 2H), 7.65-7.71 (m, 2H), 7.91-7.99 (m, 4H), 8.05 (d, J=7.7 Hz, 1H), 8.29 (d, J=8.1 Hz, 1H), 8.49 (d, J=8.2 Hz, 1H), 8.57 (d, J=8.2 Hz, 1H), 11.66 (s, 1H), 11.76 (s, 1H), 12.62 (br s, 1H), 13.80 (br s, 1H). LCMS (m/z): $[M-H^+]^-$ calcd for $[C_{28}H_{20}N_3O_5]$, 478.14. found, 478.45.

Quantitative Real-Time PCR

Approximately $1\times10^5$ A549 cells were seeded in 24-well plates (Nunc) on the day before infection. On the day of infection, the cells in one well were counted to establish the amount of virions to be added. The growth medium was removed and compound and virus were added simultaneously to the cells in 700 μl DMEM with 0.75 g/l $NaHCO_3$, 20 mM HEPES, 1×PEST, and 1% FBS. Compounds were added in concentrations ranging from 0.5 μM to 15 μM. The final concentration of DMSO was less than 1% in all samples. One pg of Ad virions was added per cell. The plate was incubated at 37° C. in 5% $CO_2$ and 24 h after infection the cells were harvested, washed once, and resuspended in PBS. DNA was prepared from the samples using the QIAamp DNA Blood Mini Kit (QIAGEN, Solna, Sweden) according to the manufacturer's instructions. The design of primers and probes for analysis of various Ad types representing different adenovirus species with quantitative PCR has been described previously (Allard et al. 2001. *Rapid typing of human adenoviruses by a general PCR combined with restriction endonuclease analysis. Journal Clinical Microbiology* 39:498-505). Briefly, quantitative real-time PCR was carried out using a degenerate primer pair, Kadgen1 (forward)—Kadgen 2 (reverse) (5'-CWT ACA TGC ACA TCK CSG G-3'—SEQ ID NO:1, and 5'-CRC GGG CRA AYT GCA CCA G-3'—SEQ ID NO:2, respectively); DNA technology A/S, Aarhus, Denmark). This primer pair is specific for the conserved region of the Ad hexon gene and can detect all human Ads. Different FAM-TAMRA probes were used to quantitate Ads from different species: AdB1B2 (5'-6-FAM-AGG ATG CTT CGG AGT ACC TGA GTC CGG-TAMRA-3'—SEQ ID NO:3) for Ad11p (11) and AdC (5'-6-FAM-AGG ACG CCT CGG AGT ACC TGA GCC CCG-TAMRA-3'—SEQ ID NO:4) for Ad 5 (all from Applied Biosystems, Cheshire, UK). For Ads from species A, D, E and F the probe AdDF (5'-6-FAM-CCG GGC TCA GGT ACT CCG AGG CGT CCT-3'—SEQ ID NO:5) was used (Applied Biosystems). Standard curves ranging from 5 to $5\times10^5$ genome copies were generated by serial dilution of known amounts of full-length Ad5 or Ad11 DNA. The Ad5 DNA standard was used for the AdDF probe system. The amplification was performed in a 25-μl reaction mixture containing the following: 10 μl Ad5 standard DNA or Ad11 standard DNA or 10 μl DNA from samples, 2.5 μl 10×Taq buffer, 5 μl 25 mM $MgCl_2$, 2.0 μl 2.5 mM dNTPs, 1.0 μl 25 μM Kadgen1, 1.0 μl 25 μM Kadgen2, 0.29 μl 15 μM probe AdB1B2 or probe AdDF or 1.0 μl 5 μM probe AdC, 0.2 μl Ampli Taq Gold polymerase at 5 U/μl, 0.25 μl AmpErase uracil N-glycosylase (UNG), and 2.76 μl $H_2O$ for Ad11p and 2.05 μl $H_2O$ for Ad5 (Applied Biosystems, Roche Molecular Systems, Branchburg, N.J.). The program for the real-time PCR was: 2 min at 50° C. to activate UNG, followed by amplification and quantitation (10 min at 95° C. and 40 cycles of 15 sec at 95° C., 1 min at 60° C.). The efficiency of the real-time PCR assay was the same for both probe systems used (data not shown). To standardize the number of adenoviral genome copies per cell, real-time PCR analysis was performed on the same samples using the cellular RNase P as a reference gene. The TaqMan® Rnase P Detection Reagents kit (20× mix containing primers and a FAM/TAMRA probe) (Applied Biosystems, Foster City, Calif.) was used for the analysis. The PCR reaction mixture was otherwise the same as with Ad primers and probes. Real-time PCR was performed in an ABI PRISM 7700 Sequence Detector (Applied Biosystems) and analyzed with Sequence Detector v1.7a software.

The effect of the three molecules on the replication of Ad5 in A549 cells was assessed in a QPCR assay. A significant inhibitory effect on Ad5 replication could only be observed for the original compound, A02. Neither the smaller (A01) nor the larger (A03) molecule showed any anti-adenoviral effect.

Binding Experiments

A549 cells were washed twice and detached from the culture flask with 0.05% EDTA in PBS, resuspended in culture medium, and allowed to recover for 1 h at 37° C. The cell suspension was centrifuged at room temperature at 450 g for 5 min and resuspended in PBS containing 1% FBS and 0.01% $NaN_3$ (PBS-FBS-$NaN_3$); 200,000 cells per well were dispensed in a 96-well microtiter plate (Nunc). The plate was placed on ice and the compound was added to final concentrations of 5 μM and 15 μM. The final concentration of DMSO was less than 1% in all samples. Five pg $^{35}$S-labeled Ad5 virions (with labeling done as described previously by Segerman et al. 2003 (*Journal of Virology* 77:1157-1162)) were added per cell and the plate was incubated on ice on a rocking platform for 1 h. Following incubation the cells were washed three times with PBS-FBS-$NaN_3$, pelleted by centrifugation at 800 g for 5 min at 4° C. and resuspended in 100 μl PBS. The suspension was transferred to scintillation tubes containing 2 ml scintillation liquid (Wallac OptiPhase HiSafe 3, PerkinElmer) and cell-associated radioactivity was measured as counts per minute (cpm) using a liquid scintillation counter (Wallac 1409).

Inhibition of Wild-Type Ad5 and Ad11p.

The antiviral potency of compound A02 in the A549 cell system was assessed by measuring the effect on newly synthesized viral genomes of Ad5 and Ad11p by the QPCR assay. Titration resulted in comparable $IC_{50}$ values of 3.7 μM and 2.9 μM for Ad5 and Ad11p, respectively (FIG. 3) Inhibition of wild-type Ad5 and Ad11p is substantially more efficient than inhibition of the viral vector in K562 and A549 (compare FIGS. 1, 2, and 3).

Effect on Binding of Ad5 to A549 Cells

Figure 4:
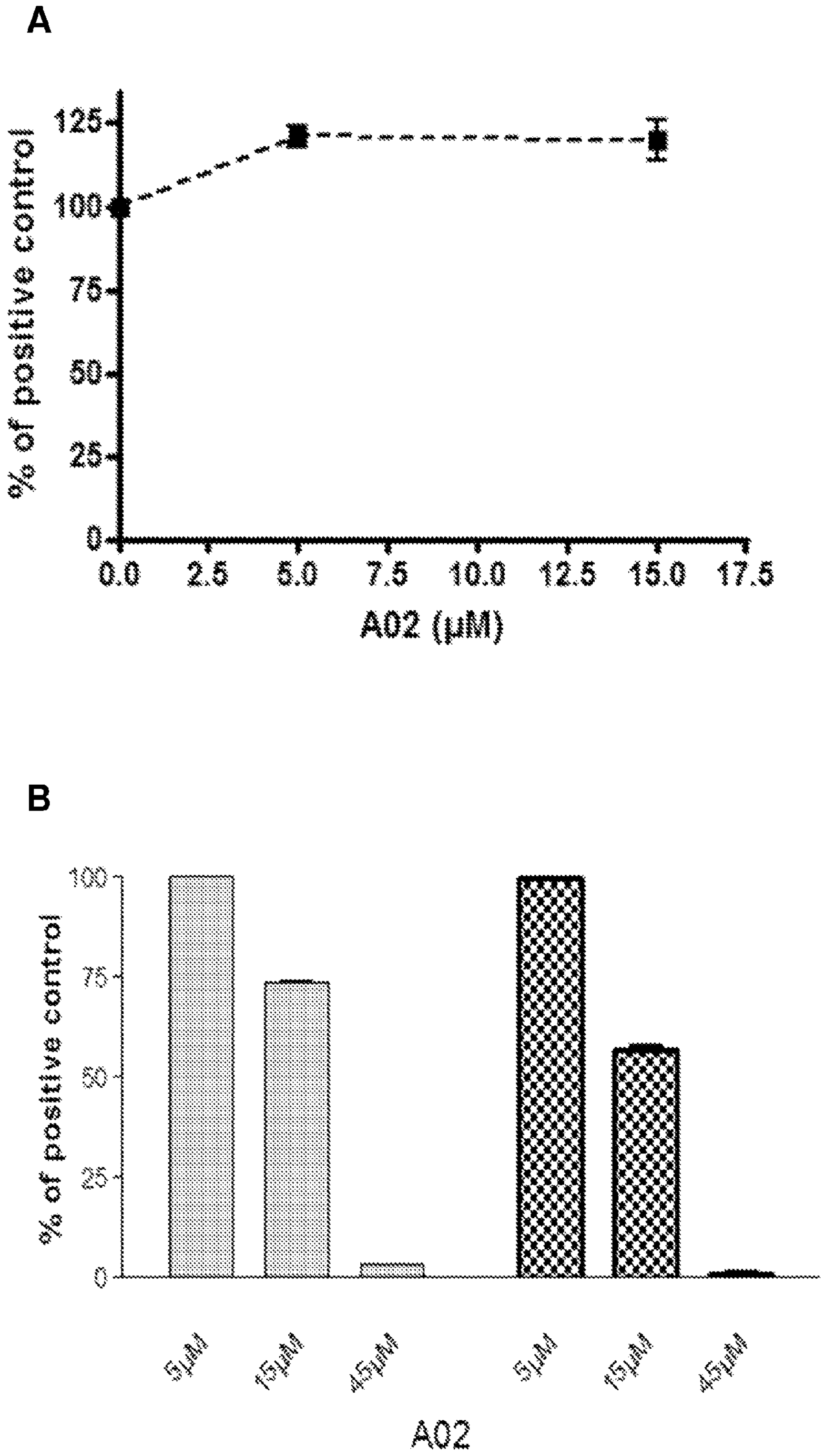
FIG. 4. A. Binding of $^{35}$S-labelled Ad5 to A549 cells in the presence of A02. Error bars represent the standard deviation of the means from three independent duplicate experiments. B. Flowcytometry assay detecting Ad5 (grey bars) and Ad11 (checkered bars) hexon protein following 24 h incubation with virus and compound A02. Error bars represent the standard deviation of the means from two independent duplicate experiments.

A binding assay using isotope-labeled virions was used to address whether the compound would prevent viral adhesion to host cells. At 15 μM, compound A02 has no effect on Ad5 binding to the surface of A549 cells (FIG. 4A). To further verify inhibition of viral replication, the effect on the expression of the most abundant viral structural protein (hexon) in A549 cells was studied by FACS analysis. The results showed that expression of Ad5 and Ad11p hexon protein is inhibited by compound A02 in a dose-dependent manner (FIG. 4B).

Toxicity.

Figure 3:
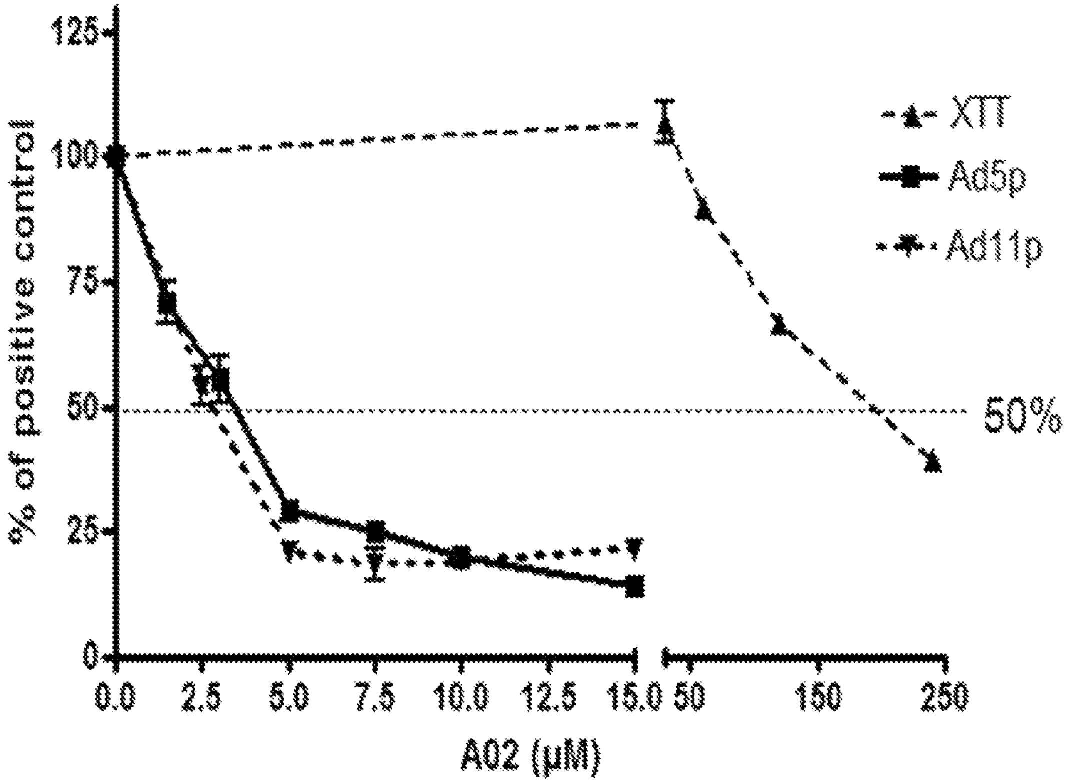
FIG. 3. Titration of the effect of A02 on Ad5, Ad11p and the toxic effect in A549 cells following 24 h incubation with virus and/or compound A02. $IC_{50}$ for Ad5 and Ad11p was 3.7 μM and 2.9 μM, respectively. $CC_{50}$ for compound A02 in A549 cells was 199 μM. $IC_{50}$ is the concentration at which the Ad replication is inhibited by 50% as determined by qPCR and $CC_{50}$ is the concentration at which the cytotoxicity is 50%, i.e. 50% of the cells are viable, as determined by the XTT assay. Error bars represent the standard deviation of the means from three independent duplicate experiments.

Toxicity of A02 in the A549 cell system was also analyzed by titration, giving a 50% cytotoxic concentration ($CC_{50}$) of 199 μM (FIG. 3). This can then be combined to give a selectivity index ($SI=CC_{50}/IC_{50}$) of 54 and 68 for Ad5 and Ad11p, respectively.

Effect on Different Adenovirus Species.

With the clear-cut effect of A02 on both Ad5 (species C) and Ad11p (species B) verified at several levels of the infection cycle, we performed an analysis to ascertain whether A02 could also affect Ads of other species (3). The results are summarized in Table 1. DNA replication of all Ads tested is inhibited by compound A02 in a dose-dependent way. A02 appears to have a general effect on Ads from all species.

TABLE 1

QPCR determination of DNA replication inhibition in A549 cells for representative Ads from all species

| Ad type (species) | % inhibition of DNA replication (SD) A02 5 μM | A02 15 μM |
|---|---|---|
| Ad31 (A) | 86 (11.8) | 98 (0.8) |
| Ad11p (B2) | 79 (4.4) | 79 (3.1) |
| Ad5p (C) | 72 (6.2) | 86 (5.5) |
| Ad37 (D) | 86 (3.3) | 94 (1.8) |
| Ad4 (E) | 85 (4.2) | 96 (1.2) |
| Ad41 (F) | 80 (9.3) | 88 (5.4) |

Discussion

Screening-based strategies are well-suited for identification of compounds with potential anti-adenoviral activity. The presently used assay is based on a replication competent Ad11p vector. The GFP gene is located in the E1 region of the Ad11p genome and detection of fluorescence by GFP expression is directly correlated to Ad11p genome expression. This assay, developed for anti-adenoviral screening, is versatile due to its robustness, its simplicity and the direct measurement of inhibition of Ad genome expression. K562 cells were used in the screening assay, since they are suspension cells that are permissive for Ad11p infection. Any hits found in a screening campaign must, however, be thoroughly verified since screening can be imprecise in many respects. We decided to concentrate the verification on Ad5 inhibition since other potential anti-adenoviral drugs have been evaluated on the basis of their effects on species C adenovirus types. There is no replication-competent Ad5 vector available; thus, Ad5 could not be used for screening. K562 cells are not permissive for Ad5 infection and the cell line of choice for verification was A549.

The discovery of more than one molecule in the most promising hit illustrates the necessity for quality control and thorough validation to verify that hits found in a screening campaign represent homogenous preparations of the correct molecule, with the desired biological activity. In this particular case, the finding provided an opportunity for a preliminary analysis of the structure-activity relationship. The anti-adenoviral effect of A02 only, but not the analogs A01 and A03 has been verified in a number of assays. There appears to be a size restriction for the compound to exert its inhibitory effect. Since neither the smaller analog A01 nor the larger A03 analog has inhibitory effects, it is tempting to speculate that there may be a pocket in the target protein into which A02 fits, where A01 is too small to cover the required site and A03 is too bulky to fit.

Considering the fact that DNA replication of all Ad types tested was inhibited by A02, although not with the same efficiency, inhibition by this compound appears to be general for human Ads (Table 1) Inhibition of Ad31 is especially important, since this is one of the most threatening adenovirus types, which can infect immunocompromised individuals in general and pediatric transplant recipients in particular.

Example 3

Inhibition of Herpes Virus

Quantitative Real-Time PCR for Herpes Simplex Quantification

Same procedure as for qPCR for adenovirus quantification was followed with the exception of a few steps. Namely, $7\times10^4$ green monkey kidney (GMK) cells were seeded in 24-well plate the day before infection. Seventy-five virus particles of HSV-1 (stock 1351-95 P13) were added per cell. After 24 h incubation with the compound A02 at 37° C. in 5% $CO_2$, the cells were harvested and DNA was prepared from 200 μL of the total 500 μL well-volume to include the DNA of possible released HSV-1 particles. The primers used in the qPCR assay were; Rune 1 (sense—position 137680-137697 in HSV-1 genome) (5'-GGC CTG GCT ATC CGG AGA-3'—SEQ ID NO:6) and Rune 2 (antisense—position 137742-137726 in HSV-1 genome) (5'-GCG CAG AGA CAT CGC GA-3'—SEQ ID NO:7), the final concentration in the reaction mixture of the primers were 300 nM. As in the adenovirus quantification a FAM-TAMRA labeled probe was used; Rune 3 (5'-CAG CAC ACG ACT TGG CGT TCT GTG T-3'—SEQ ID NO:8) to a final concentration of 175 nM in the reaction mixture.

Results

Figure 5:
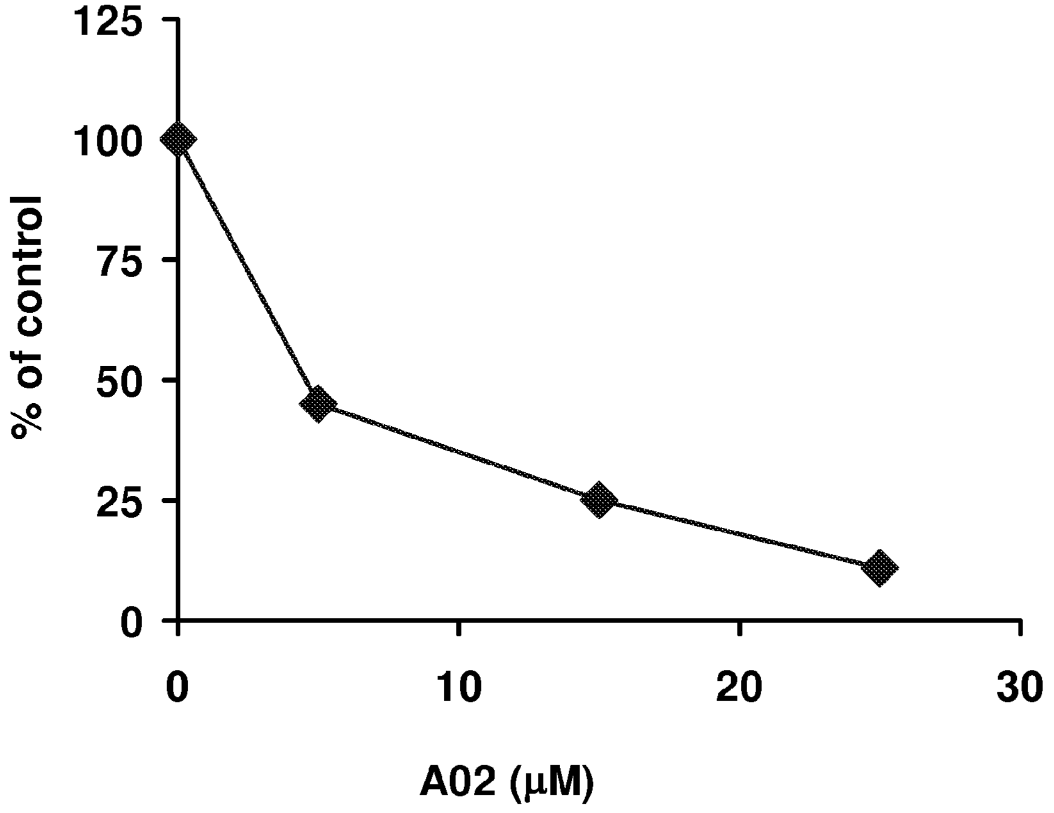
FIG. 5. Dose-response for A02 inhibition of herpes simplex 1 replication in GMK cells as determined by qPCR.

The inhibitory effect of A02 on a herpes simplex 1 replication in GMK cells is shown in FIG. 5. The inhibitory effect of A02 on herpes simplex 1 is about the same as observed with the representatives of all the six human adenovirus species.

Example 4

Synthesis of New Antiviral Compounds

A general synthetic route to compounds 8a-d is presented in Scheme 1. Activation of acids 4a-c with oxalyl chloride and coupling to anilines 5a-c gave amides 6a-d. Subsequent fluoride mediated removal of the 9-fuorenylmethocarbonyl (Fmoc) group followed by benzoylation in a one-pot, two-step procedure afforded esters 7a-d in 9-57% yield from 4a-c after HPLC purification (Table 1). Portions of the ethyl esters 7a-d were saponified and the acids 8a-d were isolated in 81-86% after HPLC purification (Table 2).

Scheme 1. Synthesis of esters 7a-d and acids 8a-d.

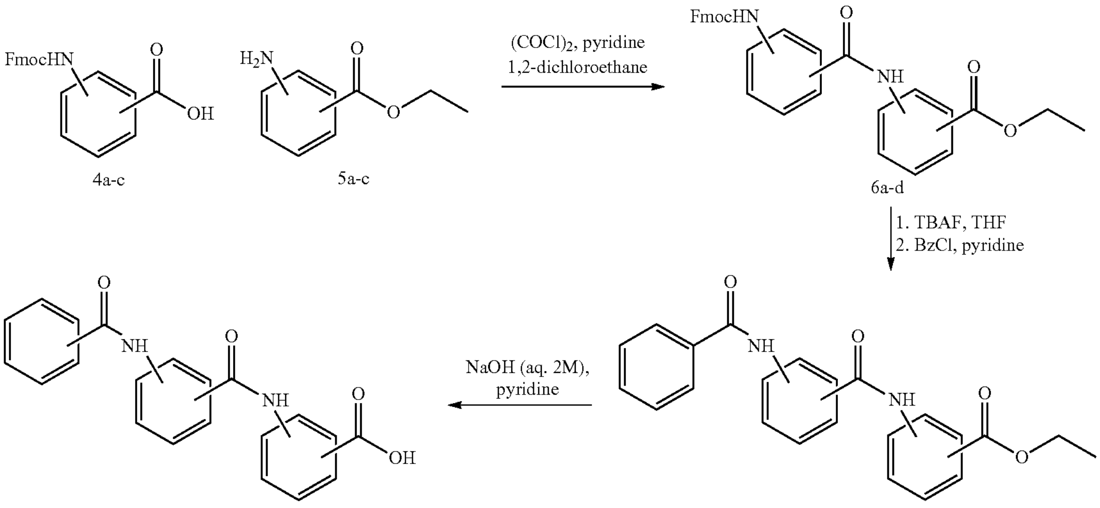

4a-c 5a-c 6a-d 7a-d 8a-d

TABLE 2

| Inhibition of adenovirus replication with synthesized compounds. | | | |
|---|---|---|---|
| Cpd | Structure | R | Inh.* |
| 7a<br>8a | 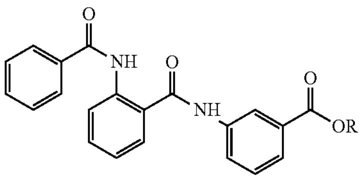 | Ethyl<br>H | 0<br>8 |
| 7b<br>8b | 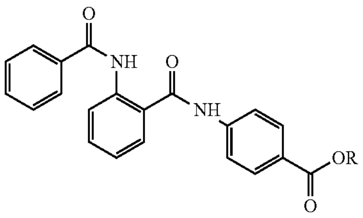 | Ethyl<br>H | 8<br>8 |
| 7c<br>8c | 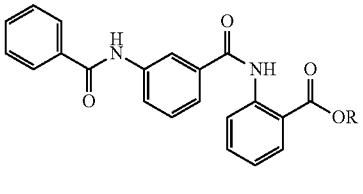 | Ethyl<br>H | 25<br>39 |
| 7d<br>8d | 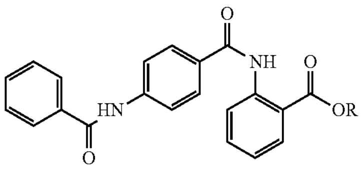 | Ethyl<br>H | 15<br>47 |

TABLE 2-continued

| Inhibition of adenovirus replication with synthesized compounds. | | | |
|---|---|---|---|
| Cpd | Structure | R | Inh.* |
| 11 | 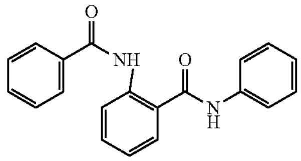 [SMILES: O=C(Nc1ccccc1C(=O)Nc1ccccc1)c1ccccc1] | — | 18 |

*% inhibition of Ad5 at 15 μM.

To validate if the carboxylic acid moiety of the lead compound A01 was critical for biological activity, reference compound 11 without the carboxylic acid was synthesized (Scheme 2). The route was essentially as described in Scheme 1, but we were more successful when using the coupling reagent (benzotriazol-1-yloxy)tris(dimethylamino) phosphonium hexafluorophosphate (BOP) in the first coupling as compared to using oxalyl chloride, and 10 was isolated in 28% yield.

Scheme 2. Synthesis of compound 11.

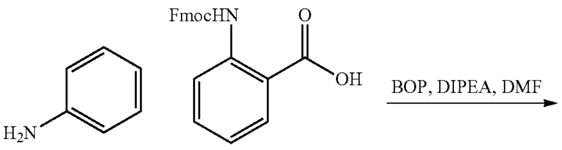

9 4a

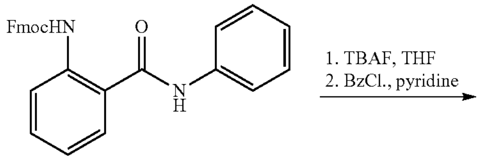

10

-continued

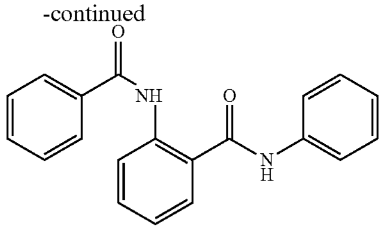

11

Esters 7a-d, acids 8a-d, and 11 were purified by normal-phase column chromatography followed by reversed-phase HPLC to give the compounds in >95% purity according to the HPLC UV trace.

Biology and Structure-Activity Relationships

Based on lead compound A02, compounds 7a-d, 8a-d, and 11 (Scheme 1, Table 2) were designed and synthesized to study the importance of the substituent pattern and if the carboxylic acid is required for activity. In addition a set of commercially available analogs, compounds 12c-g, were acquired and tested (Table 3).

TABLE 3

Inhibition of adenovirus Ad5 replication with commercial compounds.

| Cpd | Structure | % Inh. at 20 μM | % Inh. at 5 μM |
|---|---|---|---|
| 12c | 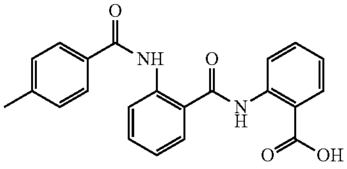 [SMILES: Cc1ccc(C(=O)Nc2ccccc2C(=O)Nc2ccccc2C(=O)O)cc1] | 98.5 | 89.2 |
| 12d | 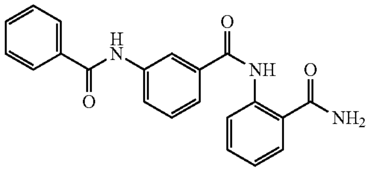 [SMILES: NC(=O)c1ccccc1NC(=O)c1cccc(NC(=O)c2ccccc2)c1] | 44.2 | 51.1 |
| 12e | 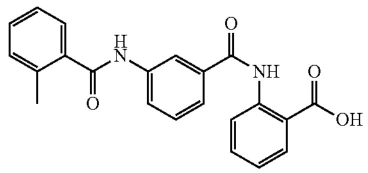 [SMILES: Cc1ccccc1C(=O)Nc1cccc(C(=O)Nc2ccccc2C(=O)O)c1] | 55.8 | 44 |
| 12f | 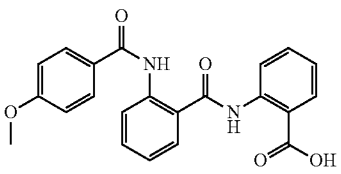 [SMILES: COc1ccc(C(=O)Nc2ccccc2C(=O)Nc2ccccc2C(=O)O)cc1] | 96.5 | 25.2 |
| 12g | 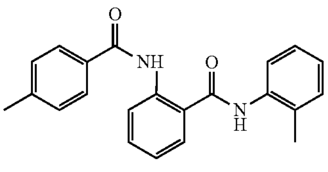 [SMILES: Cc1ccc(C(=O)Nc2ccccc2C(=O)Nc2ccccc2C)cc1] | 22.2 | 24.5 |

All compounds were screened for inhibition of intracellular adenoviral replication essentially as described in Example 1. Compound A02 contains a right hand ring with ortho connected substituents and a central ring with ortho connected substituents as well. Moving to carboxylic acid moiety to meta (8a) and para (8b) position resulted in a sharp decrease in activity. Changing the substitution pattern on the central ring to meta (8c) and para (8d) resulted in reduced activity, although less dramatic as compared to 8a and 8b. This result indicates that there seem to be more room for changes in the left hand part of the molecule. The wiggle room seen in the left hand portion of the molecule is further evident since A02, 12c, and 12f show virtually identical activities, as do 12e and 8c (Table 2 and 3). Thus, a second generation of compounds where the left hand ring is varied has been designed, synthesized and evaluation is underway. The ortho, ortho substituent pattern thus appears favourable for the [(benzoylamino)benzoylamino]-benzoic acid class of inhibitors of adenovirus replication.

The esters 7a-d corresponding to the acids 8a-d were included in the assay as potential prodrugs and/or to probe the importance of the carboxylic acid. A comparison of the ester/acid pairs 7c/8c and 7d/8d showed that the acids were more active than the corresponding esters (Table 1). The ester 7c inhibits replication to some extent but the corresponding amide 12d is less active indicating that the presence of a carboxylic acid in the ortho position is beneficial but not critical (Table 2 and 3). The preference for acid 8c appears not to be a steric effect since 12d and 8c will occupy very similar volumes. This is further evident when comparing A02 with 8a, 8b, 11, and 12g where it even seems worse to have a carboxylate in the meta and para position (8a and 8b) than none at all (11) or a methyl group in the ortho position (12g) (Table 2 and 3).

Typical Procedure for the Synthesis of Compounds 6a-d (Scheme 3).

Ethyl 3-[2-amino-(N-Fmoc)benzoylamino)]-benzoate Compound 6a

Scheme 3

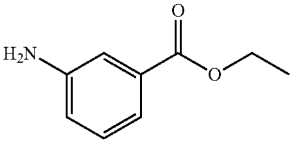

5b

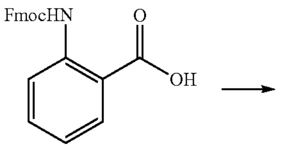

4a

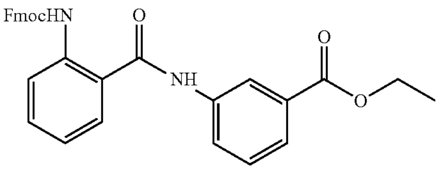

6a

A catalytic amount of DMF was added to a stirred solution of Fmoc-2-aminobenzoic acid 4a (100 mg, 278 μmol) and oxalyl chloride (0.49 mL, 5.57 mmol) in 1,2-dichloroethane (3 mL) at r.t. and under nitrogen atmosphere. After 40 min, the reaction was concentrated, re-dissolved in 1,2-dichloroethane and concentrated again. The crude was immediately dissolved in 1,2-dichloroethane (4 mL) before pyridine (0.22 mL, 2.78 mmol) and ethyl 3-aminobenzoate 5b (184 mg, 1.11 mmol) was added. The reaction was stirred o.n. at r.t. and under nitrogen atmosphere before being diluted with DCM and washed with HCl (aq., 1M), $NaHCO_3$ (aq., sat.) and brine. The organic phase was dried over $MgSO_4$, filtered, and concentrated. The crude 6a was purified by column chromatography ($SiO_2$, toluene:acetone 98:2→95:5) and taken directly to the next reaction.

Ethyl 4-[2-amino-(N-Fmoc)-benzoylamino)]-benzoate—Compound 6b

Ethyl 2-[3-amino-(N-Fmoc)-benzoylamino)]-benzoate—Compound 6c

Ethyl 2-[4-amino-(N-Fmoc)-benzoylamino)]-benzoate—Compound 6d

Typical Procedure for the Synthesis of Compounds 7a-d (Scheme 4).

4-Ethyl 3-[(2-benzoylamino)benzoylamino]-benzoate—Compound 7a

Scheme 4

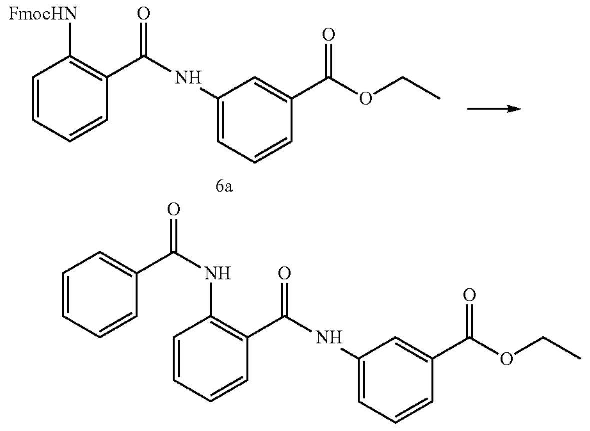

6a

7a

TBAF (1 M. 0.56 mL) was added to a stirred solution of the Fmoc-protected 6a (<278 μmol) in THF (3 mL) at r.t. and under nitrogen atmosphere. After 3 h, BzCl (0.16 mL, 1.39 mmol) and pyridine (0.22 mL, 2.78 mmol) was added and the reaction was stirred o.n. before being diluted with DCM and washed with HCl (aq., 1M), $NaHCO_3$ (aq., sat.) and brine. The organic phase was dried over $MgSO_4$, filtered, and concentrated. The crude was purified by initial column chromatography ($SiO_2$, toluene:acetone 98:2→95:5→90:10) followed by semi-preparative RP-HPLC to give ester 7a in 9% yield over two steps.

1H-NMR (500 MHz; Pyr): δ 12.47 (s, 1H), 11.60 (s, 1H), 9.19 (br d, J=8.4 Hz, 1H), 8.71 (pyr-d5 overlap, 1H), 8.30-8.28 (m, 3H), 8.16 (dd, J=7.9, 1.3 Hz, 1H), 7.99 (dt, J=7.7, 1.1 Hz, 1H), 7.53 (ddd, J=8.5, 7.2, 1.4 Hz, 1H), 7.49 (t, J=7.9 Hz, 1H), 7.44 (tt, J=7.2, 1.2 Hz, 1H), 7.41-7.38 (m, 2H), 7.08 (td, J=7.4, 1.0 Hz, 1H), 4.29 (q, J=7.1 Hz, 2H), 1.20 (t, J=7.1 Hz, 3H).

13C-NMR (126 MHz; Pyr): δ 169.17 (s, 1C), 166.12 (s, 1C), 165.41 (s, 1C), 140.72 (s, 1C), 139.53 (s, 1C), 135.54 (s, 1C), 133.02 (s, 3C), 132.11 (s, 3C), 131.71 (s, 1C), 129.37 (s, 3C), 129.19 (s, 3C), 129.08 (s, 7C), 127.72 (s, 6C), 126.49 (s, 3C), 125.86 (s, 3C), 122.92 (s, 3C), 121.72 (s, 1C), 121.58 (s, 3C), 61.16 (s, 3C), 14.23 (s, 3C).

ESIMS m/z calcd for $[C_{23}H_{19}N_2O_4]^-$, 387.14. found: 387.51.

Ethyl 4-[(2-benzoylamino)benzoylamino]-benzoate—Compound 7b

1H-NMR (400 MHz; Pyr): δ 12.37 (s, 1H), 11.67 (s, 1H), 9.16 (d, J=8.4 Hz, 1H), 8.32-8.29 (m, 2H), 8.22 (d, J=8.5 Hz, 2H), 8.14 (d, J=8.6 Hz, 2H), 8.10 (d, J=7.8 Hz, 1H), 7.54-7.41 (m, 4H), 7.04 (t, J=7.6 Hz, 1H), 4.33 (q, J=7.1 Hz, 2H), 1.25 (t, J=7.1 Hz, 3H).

13C-NMR (100 MHz; Pyr): δ 169.19 (s, 1C), 166.00 (s, 1C), 165.40 (s, 1C), 143.64 (s, 1C), 140.60 (s, 1C), 135.51 (s, 1C), 133.08 (s, 1C), 132.17 (s, 1C), 130.84 (s, 2C), 129.34 (s, 1C), 129.11 (s, 1C), 127.72 (s, 2C), 126.63 (s, 1C), 122.86 (s, 1C), 121.75 (s, 1C), 121.57 (s, 1C), 121.17 (s, 2C), 60.91 (s, 2C), 14.32 (s, 2C).

ESIMS m/z calcd for $[C_{23}H_{19}N_2O_4]^-$, 387.14. found: 387.56.

Ethyl 2-[(3-benzoylamino)benzoylamino]-benzoate—Compound 7c

1H-NMR (500 MHz; Pyr): δ 12.28 (s, 1H), 11.26 (s, 1H), 9.21 (d, J=8.3 Hz, 1H), 9.01 (s, 1H), 8.42 (br d, J=7.4 Hz, 1H), 8.23 (d, J=7.1 Hz, 2H), 8.07 (br d, J=7.7 1H), 8.01 (br d, J=7.2 Hz, 1H) 7.56-7.37 (m, 5H), 7.11 (br t, J=7.3 Hz, 1H), 4.30 (q, J=7.0 Hz, 2H), 1.24 (t, J=7.0 Hz, 3H).

13C-NMR (126 MHz; Pyr): δ 168.57 (s, 1C), 167.09 (s, 1C), 165.44 (s, 1C), 142.20 (s, 2C), 140.99 (s, 1C), 136.32 (s, 2C), 136.06 (s, 2C), 134.71 (s, 2C), 131.75 (s, 2C), 131.32 (s, 3C), 129.61 (s, 2C), 128.64 (s, 4C), 128.27 (s, 3C), 124.57 (s, 3C), 122.87 (s, 2C), 122.42 (s, 2C), 120.75 (s, 2C), 120.64 (s, 2C), 116.07 (s, 2C), 61.79 (s, 4C), 14.08 (s, 3C).

ESIMS m/z calcd for $[C_{23}H_{19}N_2O_4]^-$, 387.14. found: 387.54.

Ethyl 2-[(4-benzoylamino)benzoylamino]-benzoate—Compound 7d

1H-NMR (500 MHz; Pyr): δ 12.29 (s, 1H), 11.32 (s, 1H), 9.28 (d, J=8.4 Hz, 1H), 8.39-8.32 (m, 4H), 8.23-8.20 (m, 2H), 8.10 (dd, J=8.0, 1.4 Hz, 1H), 7.58 (ddd, J=8.6, 7.3, 1.3 Hz, 1H), 7.47-7.42 (m, 1H), 7.39 (t, J=7.4 Hz, 2H), 7.11 (ddd, J=8.1, 7.3, 0.8 Hz, 1H), 4.34 (q, J=7.1 Hz, 2H), 1.26 (t, J=7.1 Hz, 3H).

13C-NMR (126 MHz; Pyr): δ 168.69 (s,), 167.14 (s,), 165.03 (s,), 143.86 (s,), 142.49 (s,), 135.94 (s,), 134.79 (s, 1C), 131.85 (s, 1C), 131.34 (s, 1C), 130.30 (s,), 128.76 (s, 2C), 128.63 (s, 2C), 128.32 (s, 2C), 122.66 (s, 1C), 120.63 (s, 3C), 115.83 (s,), 61.78 (s, 1C), 14.09 (s, 1C).

ESIMS m/z calcd for $[C_{23}H_{19}N_2O_4]^-$, 387.14. found: 387.53.

Typical Procedure for the Synthesis of Compounds 8a-d (Scheme 5).

2-[(4-benzoylamino)benzoylamino]-benzoic acid—Compound 8d

Scheme 5

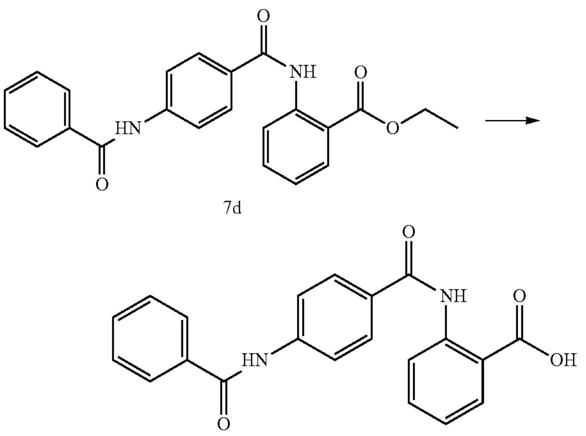

7d

8d

NaOH (aq., 2 M, 0.5 mL) was added to a stirred solution of the ethyl ester 7d (8.5 mg, 21.9 mop in pyridine (2 mL) at r.t. After 2 h, the pyridine was removed under reduced pressure, the residue diluted with EtOAc, and washed with HCl (aq., 1 M). The organic phase was dried over $MgSO_4$, filtered, and concentrated. The crude was purified by semi-preparative RP-HPLC to give the carboxylic acid 8d in 85% yield.

1H-NMR (500 MHz; Pyr): δ 13.33 (s, 1H), 11.22 (s, 1H), 9.36 (d, J=8.4 Hz, 1H), 9.12 (s, 1H), 8.50 (d, J=7.8 Hz, 1H), 8.33 (d, J=8.0 Hz, 1H), 8.22 (d, J=7.7 Hz, 2H), 8.13 (d, J=7.6 Hz, 1H), 7.61-7.55 (pyr-d5 overlap, 1H), 7.48-7.38 (m, 4H), 7.17 (t, J=7.6 Hz, 1H).

13C-NMR (126 MHz; Pyr): δ 173.33 (s, 1C), 168.02 (s, 1C), 166.43 (s, 1C), 143.61 (s, 1C), 141.87 (s, 1C), 137.64 (s, 1C), 137.14 (s, 1C), 134.95 (s, 3C), 133.12 (s, 3C), 132.71 (s, 3C), 130.52 (s, 3C), 129.62 (s, 5C), 129.24 (s, 5C), 125.22 (s, 4C), 123.71 (s, 3C), 123.70 (s, 3C), 121.59 (s, 3C), 121.42 (s, 3C), 119.24 (s, 1C).

ESIMS m/z calcd for $[C_{23}H_{19}N_2O_4]^-$, 359.10. found: 359.55.

3-[(2-benzoylamino)benzoylamino]-benzoic acid—Compound 8a

1H-NMR (400 MHz; Pyr): δ 12.87 (s, 1H), 11.98 (s, 1H), 9.57 (d, J=8.4 Hz, 1H), 9.35 (t, J=1.8 Hz, 1H), 8.68-8.61 (m, 4H), 8.51 (dd, J=7.9, 1.4 Hz, 1H), 7.93-7.86 (m, 2H), 7.82-7.71 (m, 3H), 7.43 (td, J=7.6, 1.0 Hz, 1H).

13C-NMR (100 MHz; Pyr): δ 169.17 (s, 1C), 168.76 (s, 1C), 165.40 (s, 1C), 140.70 (s, 4C), 139.48 (s, 2C), 135.53 (s, 1C), 133.46 (s, 1C), 132.95 (s, 1C), 132.09 (s, 2C), 129.28 (s, 1C), 129.24 (s, 1C), 129.08 (s, 2C), 127.72 (s, 2C), 126.33 (s, 2C), 126.09 (s, 2C), 122.87 (s, 2C), 121.77 (s, 2C), 121.50 (s, 1C).

ESIMS m/z calcd for $[C_{23}H_{19}N_2O_4]^-$, 359.10. found: 359.52.

4-[(2-benzoylamino)benzoylamino]-benzoic acid—Compound 8b

1H-NMR (500 MHz; Pyr): δ 12.41 (s, 1H), 11.65 (s, 1H), 9.18 (d, J=8.5 Hz, 1H), 8.49 (d, J=8.6 Hz, 2H), 8.33-8.30 (m, 2H), 8.18 (d, J=8.6 Hz, 2H), 8.11 (dd, J=7.9, 1.0 Hz, 1H), 7.53-7.42 (m, 4H), 7.04 (td, J=7.5, 1.0 Hz, 1H).

13C-NMR (126 MHz; Pyr): δ 169.17 (s,), 168.59 (s,), 165.41 (s,), 143.23 (s,), 140.65 (s,), 135.55 (s, 1C), 133.04 (s,), 132.15 (s, 1C), 131.20 (s, 1C), 129.34 (s, 1C), 129.13 (s, 1C), 128.41 (s,), 127.74 (s, 1C), 122.84 (s, 1C), 121.80 (s,), 121.55 (s, 1C), 121.25 (s, 1C).

ESIMS m/z calcd for $[C_{23}H_{19}N_2O_4]^-$, 359.10. found: 359.52.

2-[(3-benzoylamino)benzoylamino]-benzoic acid—Compound 8c

1H-NMR (500 MHz; Pyr): δ 13.31 (s, 1H), 11.23 (s, 1H), 9.42 (d, J=8.2 Hz, 1H), 8.53 (d, J=7.4 Hz, 1H), 8.44 (d, J=8.5 Hz, 2H), 8.27 (d, J=8.5 Hz, 2H), 8.18 (d, J=7.1 Hz, 2H), 7.63-7.55 (pyr-d5 overlap, 1H), 7.45-7.36 (m, 3H), 7.20-7.14 (pyr-d5 overlap, 1H).

13C-NMR (126 MHz; Pyr): δ 172.54 (s, 1C), 167.08 (s, 1C), 165.18 (s, 1C), 143.59 (s, 1C), 142.91 (s, 1C), 136.03 (s, 1C), 133.97 (s, 2C), 132.21 (s, 2C), 131.81 (s, 2C), 130.89 (s, 1C), 128.84 (s, 3C), 128.62 (s, 2C), 128.29 (s, 2C), 122.53 (s, 2C), 120.60 (s, 3C), 120.41 (s, 2C), 118.28 (s).

ESIMS m/z calcd for $[C_{23}H_{19}N_2O_4]^-$, 359.10. found: 359.53.

Coupling to Benzamide—Compound 10.

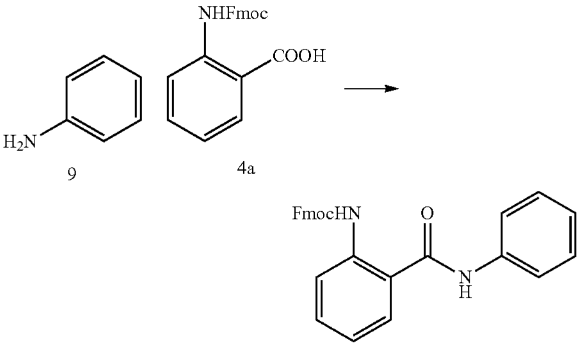

9

4a

10

Aniline 9 (114 µl, 1.25 mmol) was added to Fmoc-2-aminobenzoic acid 4a (300 mg, 835 mop, BOP (652 mg, 1.25 mmol), DIPEA (0.44 mL, 2.50 mmol) in DMF (8 mL) at r.t. After 2 h, more aniline 9 (228 µl, 2.50 mmol) was added and the reaction was stirred o.n. The reaction was diluted with HCl (aq., 1 M, 70 mL) and loaded onto a conditioned C18 SPE-column (10 g). The column was washed with HCl (aq., 1 M, 70 mL) and $H_2O$ (140 mL) before being eluted with MeOH and acetone. The pooled organic fractions were concentrated and purified by column chromatography ($SiO_2$, toluene:acetone 100:0→95:5→90:10) to give benzamide 10 in 28% yield.

1H-NMR (400 MHz; DMSO-d6): δ 10.43 (s, 1H), 10.17 (s, 1H), 7.95-7.90 (m, 1H), 7.90 (d, J=7.5 Hz, 2H), 7.80 (dd, J=7.8, 1.2 Hz, 1H), 7.72 (dd, J=8.5, 1.0 Hz, 2H), 7.67 (br d, J=7.3 Hz, 2H), 7.52 (t, J=7.7 Hz, 1H), 7.41 (br t, J=7.5 Hz, 2H), 7.37 (t, J=8.0 Hz, 2H), 7.31 (td, J=7.5, 1.1 Hz, 2H), 7.21 (td, J=7.6, 1.0 Hz, 1H), 7.13 (tt, J=7.4, 1.1 Hz, 1H), 4.44 (d, J=6.9 Hz, 2H), 4.32 (t, J=6.9 Hz, 1H).

Benzoylation of Benzamide—Compound 11.

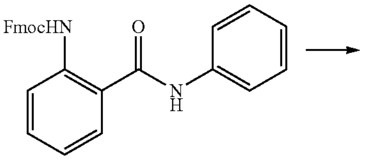

10

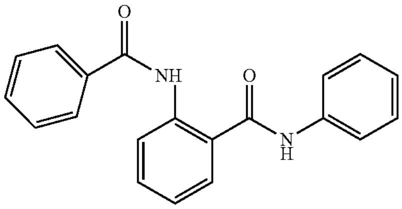

11

TBAF (0.35 mL, 0.345 mmol) was added to a stirred solution of Fmoc-protected 10 (100 mg, 0.23 mmol) in THF (3 mL) at r.t. The reaction was stirred o.n. before a pyridine (70 μL, 0.917 mmol) and BzCl (80 μL, 0.689 mmol) was added. After 3 h, the reaction was concentrated and purified by column chromatography ($SiO_2$, toluene:acetone 100:0→95:5) to give benzoylated 11 in 87% yield. Benzoylated 11 was further purified by RP-HPLC before biological testing.

1H-NMR (400 MHz; Pyr): δ 12.56 (s, 1H), 11.42 (s, 1H), 9.19 (d, J=8.4 Hz, 1H), 8.32-8.27 (m, 2H), 8.10 (dd, J=7.9, 1.3 Hz, 1H), 8.04-7.99 (m, 2H), 7.52-7.37 (m, 7H), 7.22-7.17 (pyr-d5 overlap, 2H), 7.03 (td, J=7.6, 1.1 Hz, 1H).

13C-NMR (100 MHz; Pyr): δ 168.97 (s, 1C), 165.34 (s, 1C), 140.67 (s, 1C), 139.29 (s, 1C), 135.56 (s, 1C), 132.81 (s, 1C), 132.09 (s, 1C), 129.22 (s, 1C), 129.16 (s, 1C), 129.09 (s, 1C), 127.70 (s, 1C), 125.04 (s, 1C), 122.80 (s, 1C), 122.33 (s, 1C), 121.78 (s, 1C), 121.39 (s, 1C).

ESIMS m/z calcd for $[C_{23}H_{19}N_2O_4]^-$, 315.11. found: 315.52.

Ethyl 2-(2-nitrobenzoylamino)-benzoate—Compound 20

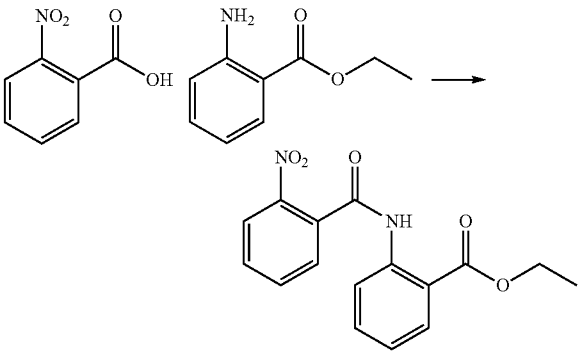

20

A catalytic amount of DMF was added to a stirred solution of 2-nitrobenzoic acid (2.30 g, 13.8 mmol) and oxalyl chloride (6.0 mL, 69 mmol) in 1,2-dichloroethane (70 mL) at r.t. and under nitrogen flow. After 1 h, the reaction was concentrated, re-dissolved in 1,2-dichloroethane and concentrated again. The crude was immediately dissolved in 1,2-dichloroethane (25 mL) before ethyl 2-aminobenzoate (1.00 mL, 6.76 mmol) and pyridine (1.70 mL, 21.0 mmol) was added. The reaction was stirred 45 min at r.t. and under nitrogen atmosphere before being diluted with DCM and washed with HCl (aq., 1M), $NaHCO_3$ (aq., sat., 2×) and brine. The organic phase was dried over $Na_2SO_4$, filtered, and concentrated. The crude was purified by column chromatography ($SiO_2$, toluene:acetone 100:0→98:2) to give compound 20 in quant yield (2.24 g).

1H-NMR (400 MHz; $CDCl_3$): δ 11.60 (s, 1H), 8.82 (d, J=8.4 Hz, 1H), 8.12-8.08 (m, 2H), 7.75-7.71 (m, 2H), 7.66-7.61 (m, 2H), 7.18 (ddd, J=7.9, 7.3, 1.1 Hz, 1H), 4.36 (q, J=7.1 Hz, 2H), 1.40 (t, J=7.1 Hz, 3H).

Ethyl 2-(2-aminobenzoylamino)-benzoate—Compound 21

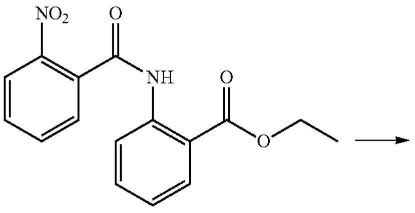

20

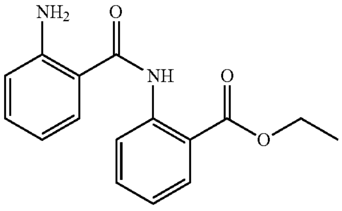

21

Nitro compound 20 (2.24 g, 7.14 mmol) and Pd/C (220 mg) was dissolved in EtOAc (50 mL) and MeOH (20 mL) and stirred vigorously under $H_2$ atmosphere (1 atm). After 5 h, the Pd/C was filtered off over a pad of celite and florisil to leave pure aniline compound 21 in quant. yield (1.98 g) over two steps.

1H-NMR (400 MHz; $CDCl_3$): δ 11.86 (s, 1H), 8.83 (d, J=8.5 Hz, 1H), 8.10 (dd, J=8.0, 1.5 Hz, 1H), 7.74 (dd, J=8.0, 1.4 Hz, 1H), 7.59 (ddd, J=8.5, 7.3, 1.4 Hz, 1H), 7.29-7.25 (m, 1H), 7.14-7.10 (ddd, J=8.3, 7.4, 1.1 Hz, 1H), 6.78 (ddd, J=8.0, 7.2, 1.0 Hz, 1H), 6.72 (dd, J=8.2, 0.8 Hz, 1H), 5.76 (s, 2H), 4.42 (q, J=7.1 Hz, 2H), 1.44 (t, J=7.1 Hz, 3H).

Typical Procedure for the Synthesis of Amides 22a-27a (Scheme 6).

Ethyl 2-[2-(benzoylamino)benzoylamino]benzoate—Compound 23a

Scheme 6

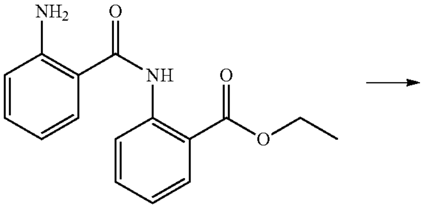

21

-continued

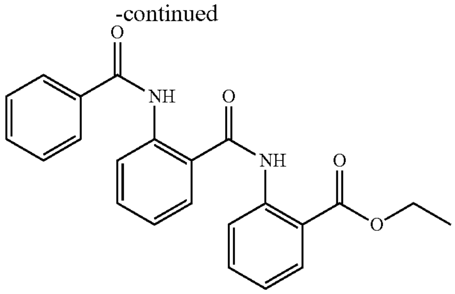

23a

Pyridine (43 μL, 0.54 mmol) was added to a stirred solution of aniline 21 (50 mg, 0.18 mmol) in DCM (0.9 mL) at room temperature under nitrogen atmosphere. After 5 min, benzoylchloride 3 (22.5 μL, 0.198 mmol) was added and the reaction was stirred for 2 h before being diluted with DCM and washed with HCl (3×, aq, 1M), $NaHCO_3$ (aq, sat), and brine. The organic phase was dried over $Na_2SO_4$, concentrated and purified by column chromatography (toluene:acetone 100:0→98:2) to give benzamide 23a in 62% yield (36 mg).

Ethyl 2-[2-(Acetylamino)benzoylamino]benzoate—Compound 22a

Ethyl 2-[2-(Trimethylacetylamino)benzoylamino]benzoate Compound 24a

Ethyl 2-[[2-(Cyclohexanecarboxylamino)benzoyl]amino]benzoate—Compound 25a

Ethyl 2-[2-(Phenylacetylamino)benzoylamino]benzoate—Compound 26a

Ethyl 2-[2-(4-Carboxybutanoylamido)benzoyl]aminobenzoate—Compound 27a

Typical Procedure for the Synthesis of Sulfonamides 29a-30a (Scheme 7).

Ethyl 2-[2-(methanesulfonylamino)benzoylamino]benzoate—Compound 29a

Scheme 7

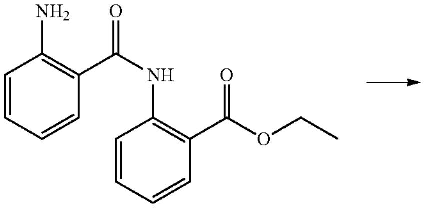

21

-continued

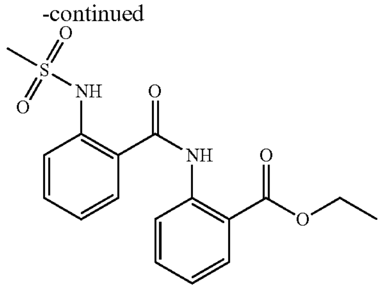

29a

Pyridine (43 μL, 0.54 mmol) was added to a stirred solution of aniline 21 (50 mg, 0.18 mmol) in DCM (0.9 mL) at room temperature under nitrogen atmosphere. After 5 min, methanesulfonyl chloride 9 (29.9 μL, 0.198 mmol) was added and the reaction was stirred overnight before being diluted with DCM and washed with HCl (3×, aq, 1M), $NaHCO_3$ (aq, sat), and brine. The organic phase was dried over $Na_2SO_4$, concentrated and purified by column chromatography (toluene: acetone 100:0→98:2) to give methanesulfonamide 29a in 60% yield (38 mg).

Ethyl 2-[2-(p-Toluenesulfonylamino)benzoylamino]benzoate—Compound 30a

Procedure for the Synthesis of Benzylamide 40a (Scheme 8).

Ethyl 2-[[2-(benzylamino)benzoyl]amino]benzoate—Compound 40a

Scheme 8

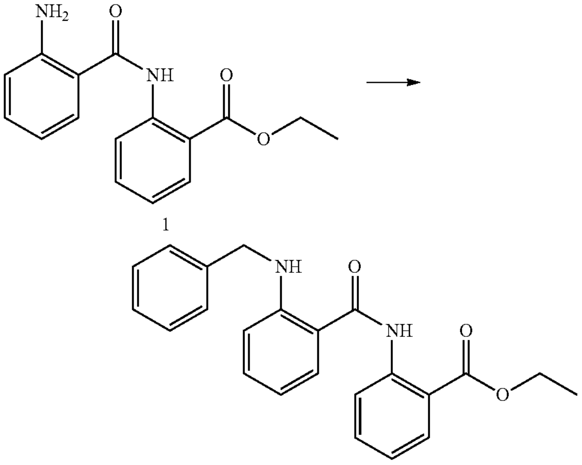

1

40a

DIPEA (61 μL, 0.54 mmol) was added to a stirred solution of aniline 1 (50 mg, 0.18 mmol) in DCM (0.9 mL) at room temperature under nitrogen atmosphere. After 5 min, benzyl bromide 11 (23 μL, 0.198 mmol) was added and the reaction mixture was heated in microwave at 80° C. for 20 min, then 100° C. for 45 min more before being diluted with DCM and washed with HCl (3×, aq, 1M), $NaHCO_3$ (aq, sat), and brine. The organic phase was dried over $Na_2SO_4$, concentrated and purified by column chromatography (toluene: acetone 100: 0→98:2) to give benzylamine 40a in 45% yield (30 mg).

Typical Procedure for Hydrolysis of Esters 22a-30a and 40a for the Synthesis of Benzoic Acids 22b-30b and 40b (Scheme 9).

2-[[2-(Benzoylamino)benzoyl]amino]benzoic acid—Compound 23b

Scheme 9

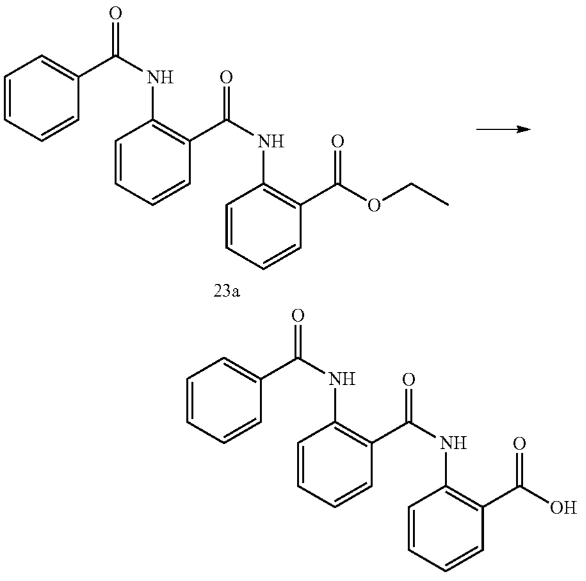

23a

23b

NaOH (aq, 2 M, 0.7 mL) was added to a stirred solution of ester 23a (53.1 mg, 0.14 mmol) in pyridine (0.7 mL) at room temperature. After 3 h, the reaction was diluted with DCM and washed with HCl (3×, 1 M in brine), $NaHCO_3$ (aq, sat), brine and dried over $Na_2SO_4$ before being purified by preparative HPLC to give acid 23b in 70% yield (35 mg).

$^1$H NMR (500 MHz, Pyridine-d5): δ 13.47 (s, 1H), 12.80 (s, 1H), 9.27 (d, J=7.8 Hz, 1H), 9.14 (d, J=8.3 Hz, 1H), 8.53 (dd, J=1.5, 6.4 Hz, 1H), 8.36 (dd, J=2.1, 8.0 Hz, 2H), 8.24 (dd, J=1.2, 7.9 Hz, 2H), 7.44-7.52 (m, 5H), 7.21-7.24 (m, 1H), 7.08-7.12 (m, 1H).

$^{13}$C NMR (500 MHz, Pyridine-d5): δ 172.3, 168.1, 165.3, 141.6, 141.2, 133.7, 133.0, 132.1, 132.0, 128.0, 123.7, 123.6, 121.5, 121.2, 120.6, 118.9

ESIMS m/z calcd for $[C_{21}H_{17}N_2O_4]^+$ 361.11. found 361.20.

2-[2-(Acetylamino)benzoylamino]benzoic acid—Compound 22b $^1$H NMR (500 MHz, Pyridine-d5): δ 13.33 (s, 1H), 11.56 (s, 1H), 9.14 (d, J=8.4 Hz, 1H), 8.96 (d, J=8.3 Hz, 1H), 8.54 (dd, J=1.5, 7.8 Hz, 1H), 8.14 (dd, J=1.1, 8.9 Hz, 1H), 7.61-7.64 (m, J=1H), 7.42-7.45 (m, 1H), 7.24 (t, J=7.9 Hz, 1H), 2.26 (s, 3H).

$^{13}$C NMR (500 MHz, Pyridine-d5): δ 173.5, 169.7, 168.9, 142.9, 141.7, 134.9, 133.7, 133.2, 129.0, 122.8, 121.6, 119.9, 26.0

ESIMS m/z calcd for $[C_{16}H_{15}N_2O_4]^+$ 299.10. found 299.25.

2-[2-(Trimethylacetylamino)benzoylamino]benzoic acid—Compound 24b $^1$H NMR (500 MHz, Pyridine-d5): δ 13.36 (s, 1H), 11.95 (s, 1H), 9.16 (dd, J=1.1, 8.5 Hz, 2H), 8.53 (dd, J=1.6, 7.9 Hz, 1H), 8.18 (dd, J=1.3, 8.0 Hz, 1H), 7.60-7.63 (m, 1H), 7.43-7.47 (m, J=1H), 7.21-7.25 (m, 1H), 7.03-7.07 (m, 1H), 1.45 (s, 9H)

$^{13}$C NMR (500 MHz, Pyridine-d5): δ 177.1, 172.3, 168.1, 141.7, 141.5, 133.8, 132.9, 132.1, 127.8, 122.8, 121.4, 121.1, 120.5, 118.8, 40.2, 27.3

ESIMS m/z calcd for $[C_{19}H_{21}N_2O_4]^+$ 341.14. found 341.24.

2-[[2-(Cyclohexanecarboxylamino)benzoyl]amino] benzoic acid—Compound 25b $^1$H NMR (500 MHz, Pyridine-d5): δ 13.38 (s, 1H), 11.73 (s, 1H), 9.15 (d, J=8.3 Hz, 1H), 9.12 (d, J=8.4 Hz, 1H), 8.53 (d, J=7.3 Hz, 1H), 8.17 (d, J=7.6 Hz, 1H), 7.57-7.60 (m, 1H), 7.43-7.46 (m, 1H), 7.20-7.23 (m, 1H), 7.04-7.07 (m, 1H), 2.09-2.11 (m, 2H), 1.65-1.72 (m, 4H), 1.49-1.51 (m, 1H), 1.09-1.23 (m, 4H).

$^{13}$C NMR (500 MHz, Pyridine-d5): δ 175.7, 173.4, 169.1, 142.8, 142.3, 134.8, 133.9, 133.2, 129.0, 122.7, 122.5, 121.6, 120.0, 48.1, 30.9, 27.0, 26.8

ESIMS m/z calcd for $[C_{21}H_{23}N_2O_4]^+$ 367.16. found 367.24.

2-[2-(Phenylacetylamino)benzoylamino]benzoic acid—Compound 26b $^1$H NMR (500 MHz, Pyridine-d5): δ 13.25 (s, 1H), 11.72 (s, 1H), 9.11 (d, J=7.9 Hz, 1H), 8.95 (d, J=8.1 Hz, 1H), 8.53 (dd, J=1.5, 7.9 Hz, 1H), 8.09 (dd, J=1.2, 7.6 Hz, 1H), 7.63-7.67 (m, 1H), 7.35-7.40 (m, 3H), 7.23-7.29 (m, 3H), 7.01-7.04 (m, 2H), 3.93 (s, 2H).

$^{13}$C NMR (500 MHz, Pyridine-d5): δ 172.2, 169.6, 167.6, 141.7, 140.5, 133.7, 132.6, 132.0, 129.8, 128.9, 127.7, 127.1, 122.0, 121.6, 120.4, 118.7, 45.6

ESIMS m/z calcd for $[C_{22}H_{19}N_2O_4]^+$ 375.13. found 375.18.

2-[2-(4-Carboxybutanoylamido)benzoyl]aminobenzoic acid—Compound 27b $^1$H NMR (500 MHz, Pyridine-d5): δ 13.31 (s, 1H), 11.83 (s, 1H), 9.16 (d, J=8.3 Hz, 1H), 9.01 (d, J=8.4 Hz, 1H), 8.53 (d, J=7.8 Hz, 1H), 8.13 (d, J=7.9 Hz, 1H), 7.61-7.64 (m, 1H), 7.38-7.41 (m, 1H), 7.21-7.24 (m, 1H), 7.00-7.03 (m, 1H), 3.04-3.07 (m, 4H).

$^{13}$C NMR (500 MHz, Pyridine-d5): δ 176.0, 173.4, 171.9, 168.9, 142.9, 141.9, 136.7, 136.5, 136.3, 134.9, 133.8, 133.2, 128.9, 122.8, 121.6, 119.9, 34.3, 30.9

ESIMS m/z calcd for $[C_{18}H_{17}N_2O_6]^+$ 357.10. found 357.23.

2-[2-(Methanesulfonylamino)benzoylamino]benzoic acid—Compound 29b $^1$H NMR (360 MHz, Pyridine-d5): δ 13.40 (s, 1H), 9.01 (d, J=8.4 Hz, 1H), 8.51 (dd, J=1.4, 7.8 Hz, 1H), 8.15 (d, J=7.9 Hz, 1H), 8.03 (d, J=8.3 Hz, 1H), 7.58-7.63 (m, 1H), 7.41-7.46 (m, 1H), 7.22-7.25 (m, 1H), 7.06-7.10 (m, 1H), 3.31 (s, 3H).

$^{13}$C NMR (360 MHz, Pyridine-d5): δ 174.3, 169.3, 143.4, 142.1, 135.7, 135.1, 133.9, 130.3, 124.9, 124.2, 122.4, 120.7, 41.7.

ESIMS m/z calcd for $[C_{15}H_{15}N_2O_5S]^+$ 335.35. found 335.26.

2-[2-(p-Toluenesulfonylamino)benzoylamino]benzoic acid—Compound 30b $^1$H NMR (500 MHz, Pyridine-d5): δ 13.15 (s, 1H), 11.33 (s, 1H), 9.02 (d, J=8.5 Hz, 1H), 8.50 (dd, J=1.4, 8.0 Hz, 1H), 8.04 (d, J=8.2 Hz, 1H), 7.98 (dd, J=0.9, 7.8 Hz, 1H), 7.93 (d, J=8.2 Hz, 2H), 7.62-7.65 (m, 1H), 7.40-7.43 (m, 1H), 7.22-7.26 (m, 1H), 7.04 (t, J=7.0 Hz, 1H), 7.00 (d, J=8.1 Hz, 2H), 1.95 (s, 3H).

$^{13}$C NMR (500 MHz, Pyridine-d5): δ 172.2, 167.2, 143.9, 141.4, 139.4, 136.8, 135.6, 133.8, 132.8, 132.0, 129.8, 127.9, 127.5, 124.5, 124.0, 122.6, 120.4, 118.6, 20.8.

ESIMS m/z calcd for $[C_{21}H_{19}N_2O_5S]^+$ 411.09. found 411.14.

2-[2-(Benzylamino)benzoylamino]benzoic acid—Compound 40b $^1$H NMR (360 MHz, Pyridine-d5): δ 13.13 (s, 1H), 9.21 (d, J=8.4 Hz, 1H), 8.50 (dd, J=1.4, 7.9 Hz, 1H), 8.15 (d, J=7.9 Hz, 1H), 7.56-7.60 (m, 1H), 7.48 (d, J=7.4 Hz, 2H), 7.15-7.34 (m, 5H), 6.80 (d, J=8.4 Hz, 1H), 6.64-6.66 (m, 1H), 4.46 (s, 2H).

$^{13}$C NMR (360 MHz, Pyridine-d5): δ 172.7, 169.2, 151.1, 143.0, 140.1, 135.1, 134.2, 133.8, 132.4, 129.2, 128.8, 127.8, 127.6, 122.7, 120.7, 118.3, 116.3, 115.9, 113.0, 47.4

ESIMS m/z calcd for $[C_{21}H_{19}N_2O_3]^+$ 347.13. found 347.22.

Example 5

Synthesis of Second Generation of Antiviral Compounds

Based on the first generation inhibitors we concluded that the ortho, ortho substituent pattern was optimal, that the free acid was beneficial and that it seemed to be room for variation in the N-terminal. Consequently, compounds 17a-k (Table 4) with variation in the N-terminal were designed and synthesized (Scheme 10). A more efficient and high-yielding route than the previous (Scheme 1) was envisioned using the nitro group of 13 as protected aniline. Gratifyingly, coupling of 13 with 5a followed by hydrogenation gave 15 quantitatively. Compound 15 was subsequently reacted with a few select activated acids, sulfonyl chlorides, succinic anhydride, and benzyl bromide to give 16a-k. Hydrolysis concluded the route to give 17a-k (Scheme 10, Table 4).

Scheme 10. Synthesis of acids 17a-k.

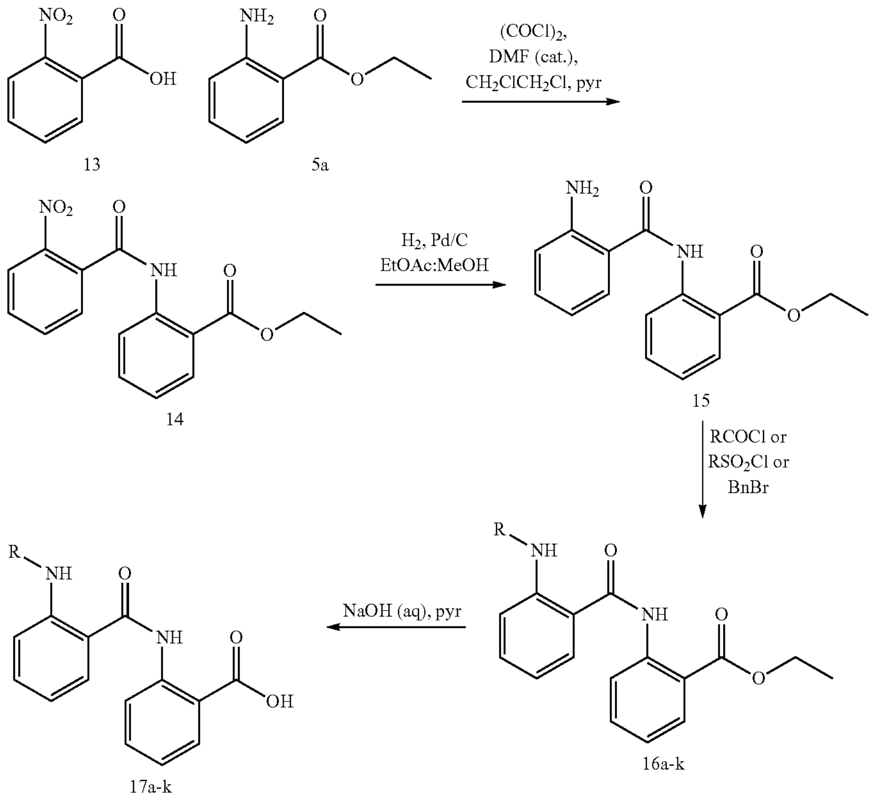

13 5a 14 15 16a-k 17a-k

Compounds 23 and 28 were synthesized to probe the (assumed) binding pocket further (Scheme 11 and 12). 23 and 28 each contains an additional methylene group compared to the parent 1. The added methylene group gives an overall slightly longer inhibitor and separates the amide-carboxylic acid in 23 and amide-amide in 28, groups that are commonly participating in directed hydrogen bonding to receptors. Apart from using phenylacetate building blocks 18 and 24 respectively, the route to 23 and 28 follows suite with the one presented in Scheme 6.

Scheme 11. Synthesis of acid 23.
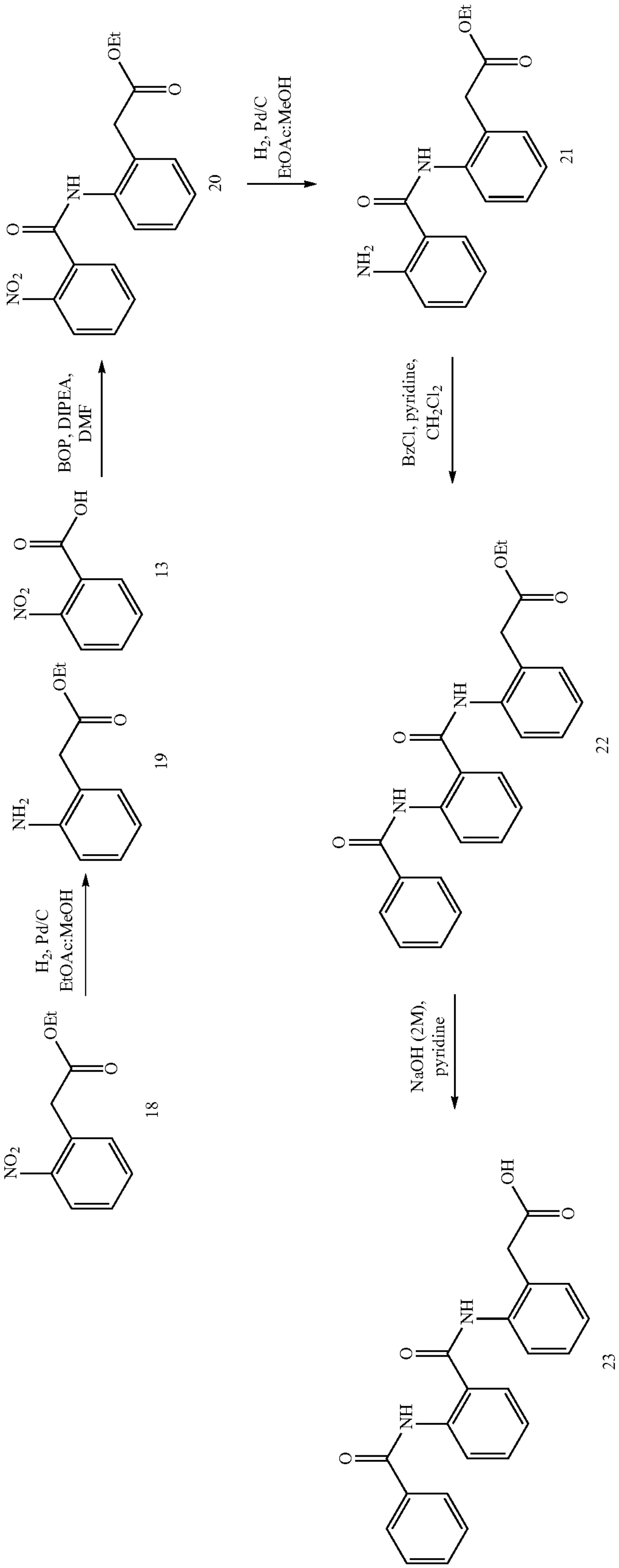
18 19 13 20 21 22 23

Scheme 12. Synthesis of acid 28.

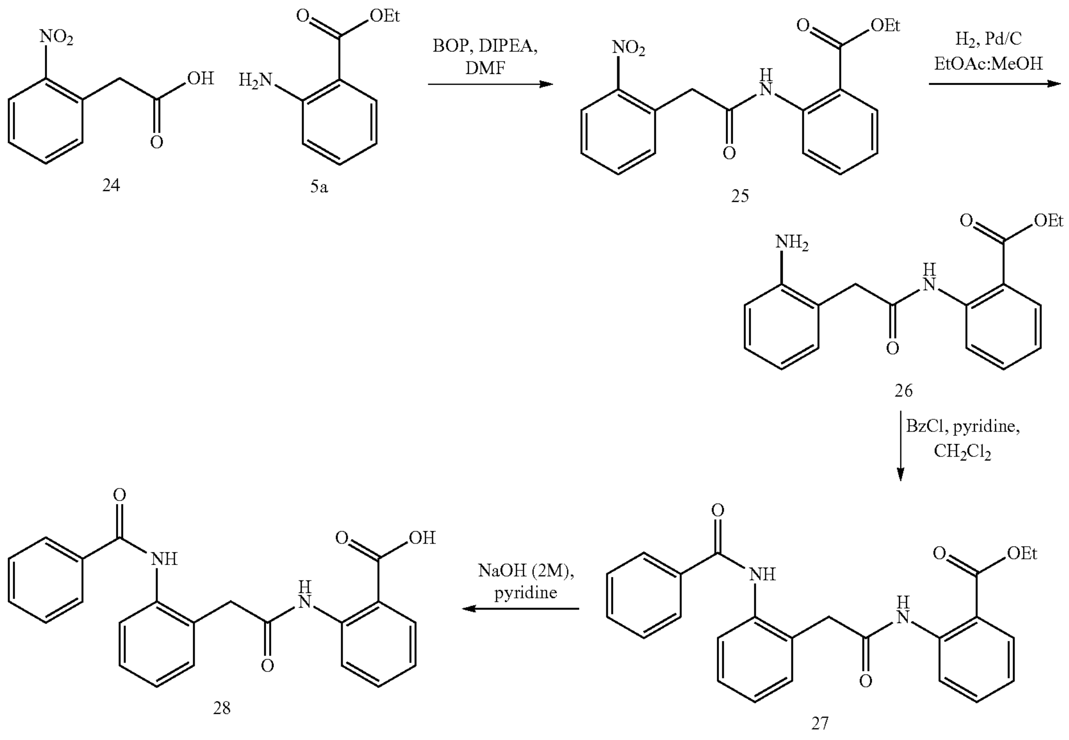

24 5a 25 26 27 28

Biology—Second Generation Inhibitors

Most of the second generation inhibitors displayed lower activity than A02 (Table 4). However, compound 17h showed statistically significantly higher activity than A02, and compound 17j was of similar potency. Noteworthy is that compounds 17e and 17g that exhibit similarities with A02 show diminished but not abolished activity while the other tested compounds showed much lower activities.

TABLE 4

Inhibition of adenovirus replication with synthesized compounds.

| Cpd | Structure | % Inh. at 15 μM | % Inh. at 5 μM |
|---|---|---|---|
| A02 | 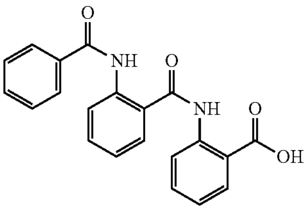 [SMILES: O=C(Nc1ccccc1C(=O)Nc1ccccc1C(=O)O)c1ccccc1] | 96 ± 1 | 89 ± 5 |
| 17a | 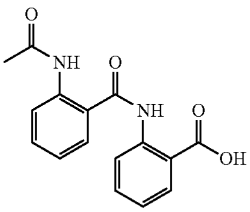 [SMILES: CC(=O)Nc1ccccc1C(=O)Nc1ccccc1C(=O)O] | 24 ± 14 | 4 ± 11 |

TABLE 4-continued

Inhibition of adenovirus replication with synthesized compounds.

| Cpd | Structure | % Inh. at 15 μM | % Inh. at 5 μM |
|---|---|---|---|
| 17b | 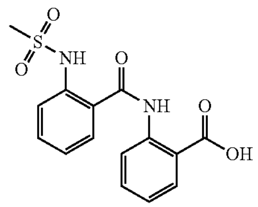 [SMILES: CS(=O)(=O)Nc1ccccc1C(=O)Nc1ccccc1C(=O)O] | 23 ± 12 | 0 |
| 17c | 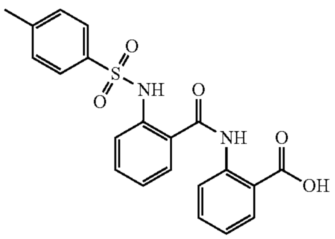 [SMILES: Cc1ccc(S(=O)(=O)Nc2ccccc2C(=O)Nc2ccccc2C(=O)O)cc1] | 8 ± 35 | 2 ± 24 |
| 17d | 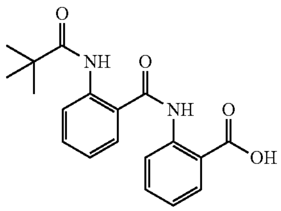 [SMILES: CC(C)(C)C(=O)Nc1ccccc1C(=O)Nc1ccccc1C(=O)O] | 52 ± 18 | 45 ± 7 |

TABLE 4-continued

| Inhibition of adenovirus replication with synthesized compounds. | | | |
|---|---|---|---|
| Cpd | Structure | % Inh. at 15 μM | % Inh. at 5 μM |
| 17e | 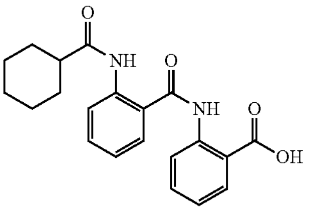 [SMILES: O=C(O)c1ccccc1NC(=O)c1ccccc1NC(=O)C1CCCCC1] | 55 ± 11 | 20 ± 1 |
| 17f | 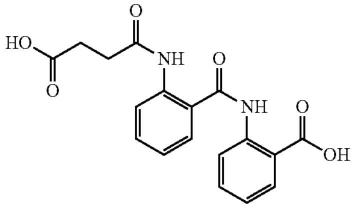 [SMILES: O=C(O)CCC(=O)Nc1ccccc1C(=O)Nc1ccccc1C(=O)O] | 0 | 0 |
| 17g | 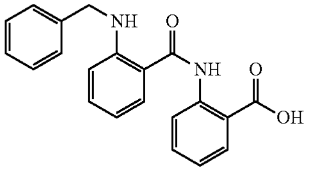 [SMILES: O=C(O)c1ccccc1NC(=O)c1ccccc1NCc1ccccc1] | 79 ± 5 | 44 ± 17 |
| 17h | 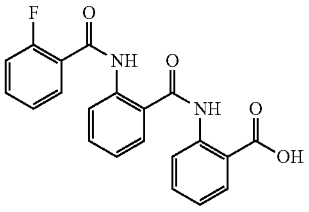 [SMILES: O=C(Nc1ccccc1C(=O)Nc1ccccc1C(=O)O)c1ccccc1F] | 96 ± 1 | 96 ± 1 |
| 17i | 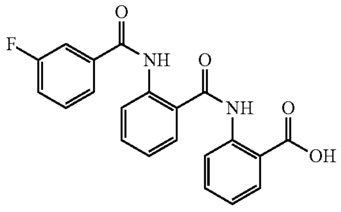 [SMILES: O=C(Nc1ccccc1C(=O)Nc1ccccc1C(=O)O)c1cccc(F)c1] | 0 | 41 ± 32 |
| 17j | 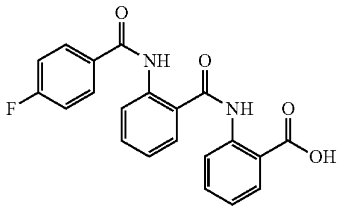 [SMILES: O=C(Nc1ccccc1C(=O)Nc1ccccc1C(=O)O)c1ccc(F)cc1] | 95 ± 1 | 76 ± 10 |

TABLE 4-continued

| Inhibition of adenovirus replication with synthesized compounds. | | | |
|---|---|---|---|
| Cpd | Structure | % Inh. at 15 μM | % Inh. at 5 μM |
| 17k | 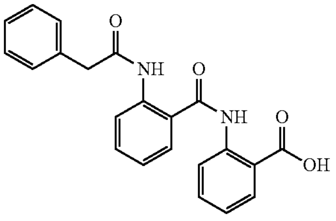 [SMILES: O=C(Cc1ccccc1)Nc1ccccc1C(=O)Nc1ccccc1C(=O)O] | 21 ± 12 | 32 ± 19 |
| 23 | 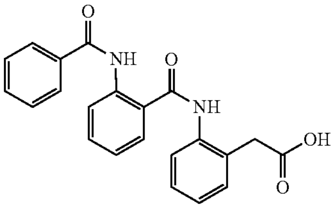 [SMILES: O=C(O)Cc1ccccc1NC(=O)c1ccccc1NC(=O)c1ccccc1] | 0 | 0 |
| 28 | 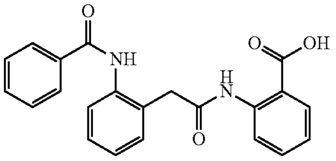 [SMILES: O=C(Cc1ccccc1NC(=O)c1ccccc1)Nc1ccccc1C(=O)O] | 0 | 0 |

Example 6

Synthesis of Third Generation of Antiviral Compounds

A further round of optimization (third generation inhibitors) was performed around 17h, the previous best compound from the second generation. Here, the central and C-terminal rings were decorated with electron donating (OMe), intermediate (Cl), and electron withdrawing (F) substituents. The synthetic route (Scheme 15) followed the one outlined previously in Scheme 3. Where amino benzoate esters were not commercially available, a methyl esterification of the corresponding commercial amino benzoic acid was conveniently carried out using trimethylsilyldiazomethane (Hashimoto, Chem. Pharm. Bull. 1981, 29(5), 1475-1478). Substantial amounts of bi-products were seen after the hydrogenolysis of the 4,5-difluoro-2-nitrobenzamide, nucleophilic aromatic substitution products may be a likely cause. In all, compounds 35a-j were synthesized (Table 5).

Scheme 15. Synthesis of acids 35a-j.

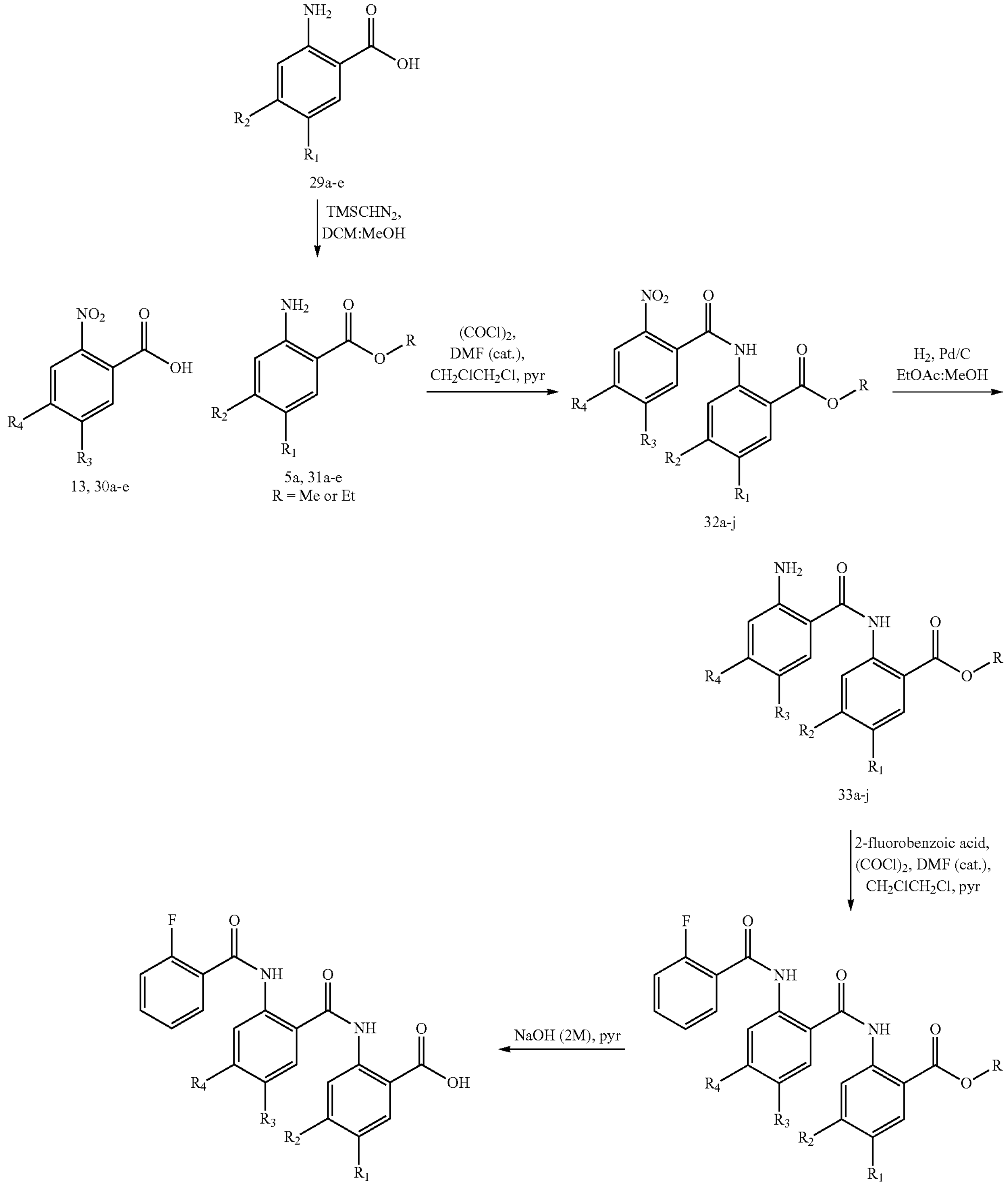

29a-e 13, 30a-e 5a, 31a-e
R = Me or Et 32a-j 33a-j 34a-j 35a-j

R$_1$ - R$_4$ = H, F, Cl, OMe

For the four chlorinated compounds 32a, 32b, 32f, and 32g, reduction with hydrogen gas over palladium on charcoal resulted in the corresponding undesired des-chloro compound. A small screen to find conditions that avoided reducing the chloro substituent was carried out: NaBH4/Pd/C; SnCl2-2H2O, and FeCl3/C/hydrazine. FeCl3/C/hydrazine conditions (see example in Scheme 5) gave enough desired product to move forward, although the method is less than ideal. For nitro compounds 32a and 32b with a methyl ester rather than an ethyl ester, no desired compound could be isolated. Rather a product where the methyl ester was cleaved was isolated as the major product, presumably due to the hydrazine. Starting with the corresponding ethyl ester instead did give enough desired product to obtain 35a and 35b, although in poor yields.

Scheme 10. Example of nitro reduction of chloro-substituted compounds 32a, 32b, 32f, and 32g.

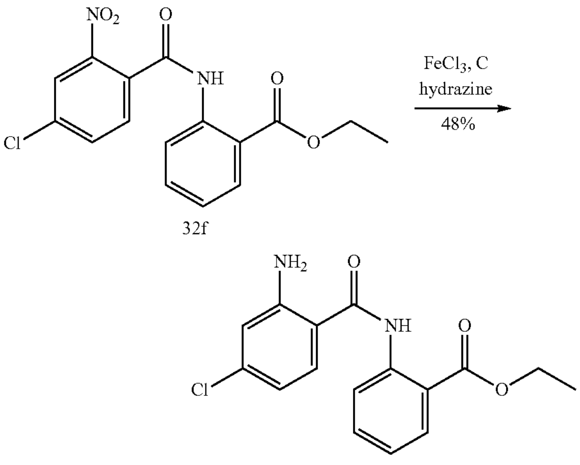

32f

33f

Biology—Third Generation Inhibitors

TABLE 5

Inhibition of adenovirus replication with synthesized compounds.

| Cpd | Structure | % Inh. at 15 μM | % Inh. at 5 μM |
|---|---|---|---|
| 35a | 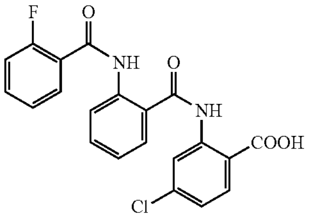 [SMILES: O=C(Nc1ccccc1C(=O)Nc1cc(Cl)ccc1C(=O)O)c1ccccc1F] | 61 ± 0 | 0 |
| 35b | 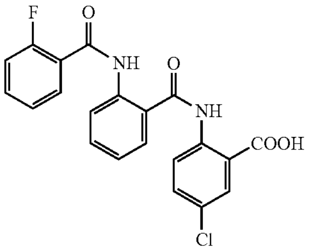 [SMILES: O=C(Nc1ccccc1C(=O)Nc1ccc(Cl)cc1C(=O)O)c1ccccc1F] | 0 | 0 |
| 35c | 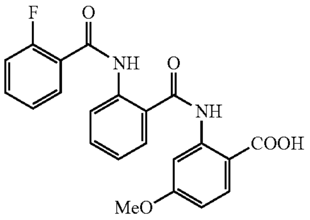 [SMILES: COc1ccc(C(=O)O)c(NC(=O)c2ccccc2NC(=O)c2ccccc2F)c1] | 95 ± 22 | 79 ± 21 |

TABLE 5-continued

Inhibition of adenovirus replication with synthesized compounds.

| Cpd | Structure | % Inh. at 15 μM | % Inh. at 5 μM |
|---|---|---|---|
| 35d | 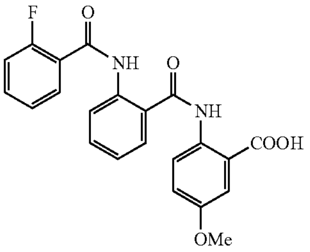 [SMILES: COc1ccc(NC(=O)c2ccccc2NC(=O)c2ccccc2F)c(C(=O)O)c1] | 78 ± 3 | 28 ± 20 |
| 35e | 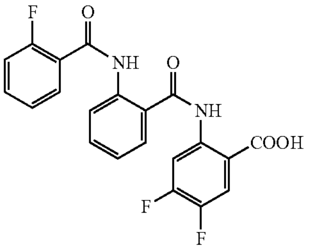 [SMILES: O=C(Nc1ccccc1C(=O)Nc1cc(F)c(F)cc1C(=O)O)c1ccccc1F] | 0 | 0 |
| 35f | 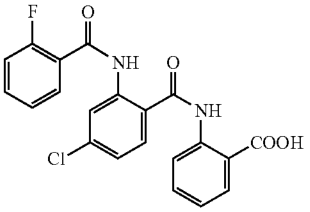 | 78 ± 2 | 57 ± 5 |
| 35g | 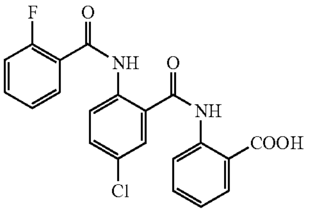 | 91 ± 2 | 89 ± 2 |
| 35h | 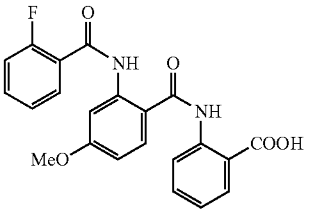 [SMILES: COc1ccc(C(=O)Nc2ccccc2C(=O)O)c(NC(=O)c2ccccc2F)c1] | 89 ± 6 | 92 ± 3 |
| 35i | 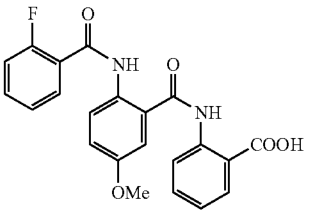 [SMILES: COc1ccc(NC(=O)c2ccccc2F)c(C(=O)Nc2ccccc2C(=O)O)c1] | 97 ± 1 | 91 ± 6 |

TABLE 5-continued

| Inhibition of adenovirus replication with synthesized compounds. | | | |
|---|---|---|---|
| Cpd | Structure | % Inh. at 15 μM | % Inh. at 5 μM |
| 35j | 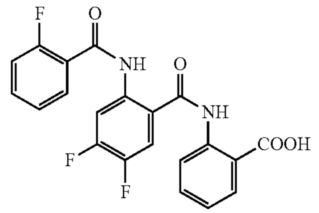 [SMILES: O=C(Nc1cc(F)c(F)cc1C(=O)Nc1ccccc1C(=O)O)c1ccccc1F] | 93 ± 2 | 94 ± 3 |

Inhibition of the RNA-Virus, Coxsackievirus Fluorescent Focus Assay

Approximately $2\times10^5$ human corneal epithelial (HCE) cells were plated in 24-well plates the day prior infection. On the day of infection the media was removed and was replaced with media containing 70 virus particles of CVA24v per cell and serial dilutions of compound 35j, ranging from 50- to 6.25 μM. After 18 h of incubation at 37° C. in 5% $CO_2$, the cells were fixed using ice-cold 100% methanol for 5 min. Thereafter, the cells were incubated with a monoclonal mouse anti-VP1 structural protein antibody (clone 5-D8/1, DakoCytomation) diluted 1:200 in PBS, for 1 h in RT. The cells were then washed with PBS and incubated with FITC labeled anti-mouse secondary antibody (DakoCytomation), diluted 1:100 for 1 h, RT, in the dark. Further, unbound antibody was washed away in PBS and the cells were examined in fluorescent microscope.

Results

Inhibition of the RNA-virus, coxsackievirus A24 variant (CVA24v), part of the picornaviridae family, by compound 35j is summarized in Table 6. The inhibition is relative to the fluorescence of CVA24v infected cells alone. No visible fluorescence was observed at 50 and 25 μM (+++), however at 12.5 and 6.25 μM some infected cells were detected (++), indicating a dose-dependent inhibition of CVA24v replication by compound 35j.

TABLE 6

| Inhibition of the RNA-virus, coxsackievirus A24 variant | |
|---|---|
| Compound 35j conc. | Relative inhibition of CVA24v |
| 50 μM | +++ |
| 25 μM | +++ |
| 12.5 μM | ++ |
| 6.25 μM | ++ |

EC50 and Toxicity of Select Compounds

Cellular toxicity is an important factor in the development of an antiviral agent and something that we have considered in the evaluation of compounds with anti-adenoviral effect. Compound A02 was selected partly based on the low cellular toxicity. The more efficient 17h is also slightly more toxic than A02 (Table 7).

TABLE 7

| Effective concentration and toxicity of selected compounds with inhibitory effect. | | | | |
|---|---|---|---|---|
| Cpd | Structure | EC50 | Toxicity at 30 μM* | Toxicity at 60 μM* |
| A02 | 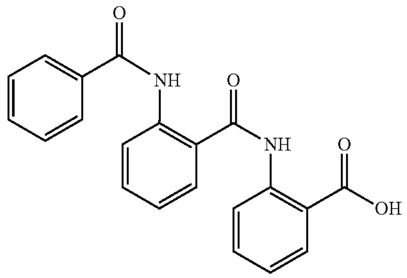 [SMILES: O=C(Nc1ccccc1C(=O)Nc1ccccc1C(=O)O)c1ccccc1] | 3.7 | 20 ± 7 | 29 ± 3 |
| 17g | 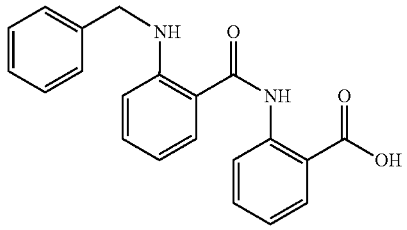 [SMILES: O=C(O)c1ccccc1NC(=O)c1ccccc1NCc1ccccc1] | 11.4 | 6 ± 10 | 11 ± 13 |

TABLE 7-continued
Effective concentration and toxicity of selected compounds with inhibitory effect.
| Cpd | Structure | EC50 | Toxicity at 30 μM* | Toxicity at 60 μM* |
|---|---|---|---|---|
| 17h | 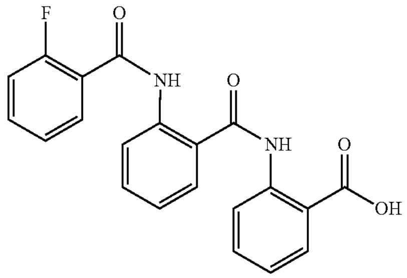 [SMILES: O=C(Nc1ccccc1C(=O)Nc1ccccc1C(=O)O)c1ccccc1F] | 2.3 | 17 ± 9 | 29 ± 12 |
| 17j | 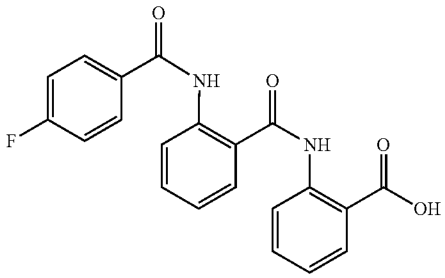 [SMILES: O=C(Nc1ccccc1C(=O)Nc1ccccc1C(=O)O)c1ccc(F)cc1] | 3.5 | 14 ± 10 | 10 ± 10 |
| 35f | 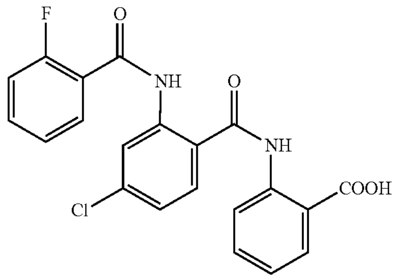 [SMILES: O=C(Nc1cc(Cl)ccc1C(=O)Nc1ccccc1C(=O)O)c1ccccc1F] | 4.14 | 14 ± 5 | 25 ± 8 |
| 35g | 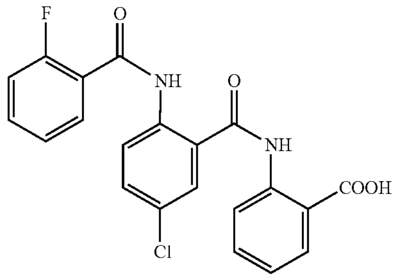 [SMILES: O=C(Nc1ccc(Cl)cc1C(=O)Nc1ccccc1C(=O)O)c1ccccc1F] | 0.68 | 11 ± 7 | 24 ± 9 |
| 35h | 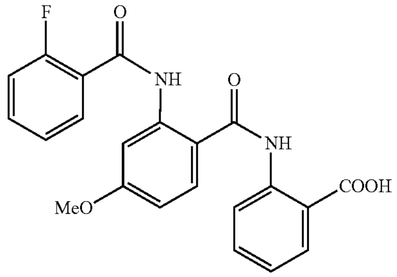 | 1.5 | 10 ± 15 | 18 ± 15 |

TABLE 7-continued

Effective concentration and toxicity of selected compounds with inhibitory effect.

| Cpd | Structure | EC50 | Toxicity at 30 μM* | Toxicity at 60 μM* |
|---|---|---|---|---|
| 35 | 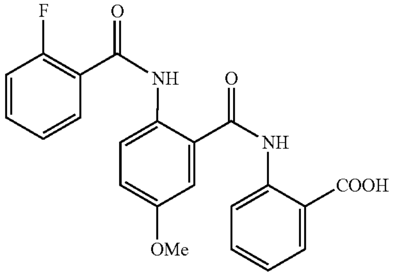 [SMILES: COc1ccc(NC(=O)c2ccccc2F)c(C(=O)Nc2ccccc2C(=O)O)c1] | 1.4 | 18 ± 12 | 28 ± 12 |
| 35j | 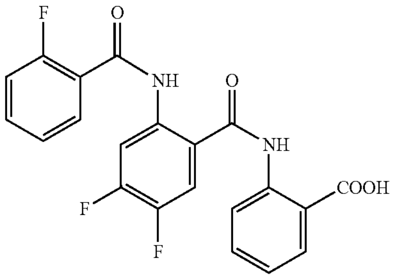 [SMILES: O=C(Nc1cc(F)c(F)cc1C(=O)Nc1ccccc1C(=O)O)c1ccccc1F] | 0.27 | 6 ± 4 | 16 ± 9 |
| DMSO | | | 2 ± 1 | 12 ± 2 |

*% dead cells after 24 h at 30 and 60 μM.

Conclusions

2-[2-Benzoylamino)benzoylamino]-benzoic acid (1) was identified as a potent adenoviral compound in a previous screening campaign. Here, initial attempts at optimizing 1 is effected by screening three generations of designed and synthesized compounds as well as seven commercial, structurally similar compounds. In the first generation, we conclude that the ortho, ortho substituent pattern and the presence of a carboxylic acid in 1 is favourable for this class of compounds and that the direction of the amide bonds as in 1 is obligate. Although there seem to be room for some variability in the N-terminal moiety of the compound class, a second set of designed compounds showed that the variability appears limited to substituted benzamides. One such benzamide (17h) shows improved activity over 1. In a third generation, the substituents on the middle and C-terminal rings were varied resulting in further potent inhibitors with very low cell toxicity. Compound 35j displayed an excellent EC50-value of 0.3 μM in this whole-cell assay along with a CC50 of 240 μM giving a toxicity/activity selectivity index of 890.

Synthetic Procedures

Procedure A: Synthesis of an Acid Chloride and Coupling to an Aniline (Exemplified by 6a)

A catalytic amount of DMF was added to a stirred solution of Fmoc-aminobenzoic acid (100 mg, 278 μmol) and oxalyl chloride (0.49 mL, 5.57 mmol) in 1,2-dichloroethane (3 mL) at r.t. and under nitrogen atmosphere. After 40 min, the reaction was concentrated, re-dissolved in 1,2-dichloroethane and concentrated again. The crude was immediately dissolved in 1,2-dichloroethane (4 mL) before pyridine (0.22 mL, 2.78 mmol) and ethyl aminobenzoate (184 mg, 1.11 mmol) was added. The reaction was stirred o.n. at r.t. and under nitrogen atmosphere before being diluted with DCM and washed with HCl (aq., 1M), $NaHCO_3$ (aq., sat.) and brine. The organic phase was dried over $MgSO_4$, filtered, and concentrated. The crude amide was purified by short-pass column chromatography ($SiO_2$, toluene:acetone 98:2→95:5) and taken directly to the next reaction.

Procedure B: Fmoc Deprotection and In Situ Coupling to an Acid Chloride (Exemplified by 11)

TBAF (1 M, 0.35 mL, 0.345 mmol) was added to a stirred solution of Fmoc-protected aniline (100 mg, 0.23 mmol) in THF (3 mL) at r.t. The reaction was stirred o.n. before pyridine (70 μL, 0.917 mmol) and BzCl (80 μL, 0.689 mmol) was added. After 3 h, the reaction was concentrated and purified by column chromatography ($SiO_2$, toluene:acetone 100:0→95:5) to give benzoylated product in 87% yield. The benzoylated product was further purified by RP-HPLC.

Procedure C: Saponification (Exemplified by 8d)

NaOH (aq., 2 M, 0.5 mL) was added to a stirred solution of the ethyl ester (8.5 mg, 21.9 mmol) in pyridine (2 mL) at r.t. After 2 h, the pyridine was removed under reduced pressure, the residue diluted with EtOAc, and washed with HCl (aq., 1 M). The organic phase was dried over $MgSO_4$, filtered, and concentrated. The crude was purified by semi-preparative RP-HPLC to give the carboxylic acid product in 85% yield.

Procedure D: BOP-Activation of a Carboxylic Acid and Coupling to an Aniline (Exemplified by 10)

Aniline (114 μl, 1.25 mmol) was added to Fmoc-aminobenzoic acid (300 mg, 835 μmol), BOP (652 mg, 1.25 mmol), and DIPEA (0.44 mL, 2.50 mmol) in DMF (8 mL) at r.t. After 2 h, more aniline (228 μl, 2.50 mmol) was added and the reaction was stirred o.n. The reaction was diluted with HCl (aq., 1 M, 70 mL) and loaded onto a conditioned C18 SPE-column (10 g). The column was washed with HCl (aq., 1 M, 70 mL) and $H_2O$ (140 mL) before being eluted with MeOH and acetone. The pooled organic fractions were concentrated and purified by column chromatography ($SiO_2$, toluene:acetone 100:0→95:5→90:10) to give the benzamide in 28% yield.

Procedure E: Hydrogenation (Exemplified by 15)

The nitro compound (2.24 g, 7.14 mmol) and Pd/C (220 mg) was dissolved in EtOAc (50 mL) and MeOH (20 mL) and stirred vigorously under $H_2$ atmosphere (1 atm). After 5 h, the Pd/C was filtered off over a pad of celite and florisil to leave pure aniline product in quant. yield (1.98 g) over two steps.

Procedure F: Coupling of an Acid Chloride or Sulfonyl Chloride with an Aniline (Exemplified by 16d)

Pyridine (43 μL, 0.54 mmol) was added to a stirred solution of the aniline (50 mg, 0.18 mmol) in DCM (0.9 mL) at room temperature under nitrogen atmosphere. After 5 min, methanesulfonyl chloride (29.9 μL, 0.198 mmol) was added and the reaction was stirred over night before being diluted with DCM and washed with HCl (3×, aq, 1M), $NaHCO_3$ (aq, sat), and brine. The organic phase was dried over $Na_2SO_4$, concentrated and purified by column chromatography (toluene: acetone 100:0→98:2) to give the derivatized aniline in 60% yield (38 mg).

Procedure G: Benzylation of an Aniline (Exemplified by 16i)

DIPEA (61 μL, 0.54 mmol) was added to a stirred solution of the aniline (50 mg, 0.18 mmol) in DCM (0.9 mL) at room temperature under nitrogen atmosphere. After 5 min, benzyl bromide 11 (23 μL, 0.198 mmol) was added and the reaction mixture was heated in microwave at 80° C. for 20 min, then 100° C. for 45 min more before being diluted with DCM and washed with HCl (3×, aq, 1M), $NaHCO_3$ (aq, sat), and brine. The organic phase was dried over $Na_2SO_4$, concentrated and purified by column chromatography (toluene: acetone 100:0→98:2) to give the benzylated aniline in 45% yield (30 mg).

Procedure H: $TMSCH_2N_2$-Mediated Esterification (Exemplified by 31e)

$TMSCH_2N_2$ (1.9 mL, 3.82 mmol, 2.0 M in hexanes) was added to a stirred solution of the aminobenzoic acid (600 mg, 3.47 mmol) in 20 mL of DCM:MeOH (9:1) under nitrogen atmosphere at room temperature. After 30 min, the reaction mixture was quenched by glacial HOAc before being diluted with DCM and washed with $NaHCO_3$ (aq., sat.). The organic phase was dried over $Na_2SO_4$, filtered, and concentrated to give the methyl aminobenzoate in 99% yield (644 mg).

Procedure I: Acid-Catalyzed Esterification (Exemplified by 31a)

1-amino-4-chloro-benzoic acid (500 mg, 2.9 mmol) and $H_2SO_4$ (conc, 0.5 mL) in EtOH (30 mL) was refluxed for 3 days before being concentrated to half-volume and diluted with NaHCO3 (aq, sat) and extracted with DCM (3×) (even though the reaction had not yet finished). The pooled DCM fractions was washed with brine, dried over $MgSO_4$, concentrated and purified by column chromatography (toluene:acetone 100:0→98:2) to give the ethyl ester in 64% yield (370 mg).

Procedure J: Nitro-Reduction Using FeCl3/C/Hydrazine (Exemplified by 33f)

Hydrazine (0.80 mL, 16.5 mmol) added to a stirred solution of nitro compound 32f (275 mg, 0.789 mmol), charcoal (50 mg, 4.16 mmol), and FeCl3 (38 mg, 0.23 mmol) in MeOH (10 mL) at 65° C. under nitrogen atmosphere. The temperature was raised to reflux and kept there for 3 h before all solids were filtered off over celite. The crude material was purified by column chromatography (toluene:acetone 100:0→98:2) to give the aniline 33f in 46% yield (115 mg).

2-[2-(Acetylamino)benzoylamino]benzoic acid—Compound 17a 17a was synthesized by procedures A, E, F, and C.

1H-NMR (500 MHz; Pyr): δ 13.33 (s, 1H), 11.56 (s, 1H), 9.15 (d, J=8.3 Hz, 1H), 8.96 (d, J=8.3 Hz, 1H), 8.54 (dd, J=7.8, 1.4 Hz, 1H), 8.14 (dd, J=7.9, 1.1 Hz, 1H), 7.64-7.61 (ddd, J=7.0, 1.5 Hz, 1H), 7.45-7.42 (ddd, J=1.2 Hz, 1H), 7.23 (t, J=7.6 Hz, 1H), 7.05 (t, J=7.2 Hz, 1H), 2.20 (s, 3H).

13C-NMR (126 MHz; Pyr): δ 172.47, 168.69, 167.89, 141.92, 140.74, 133.87, 132.75, 132.23, 128.01, 123.29, 122.10, 121.85, 120.59, 118.94, 25.05.

ESIMS m/z calcd for $[C_{16}H_{15}N_2O_4]^+$ 299.10. found 299.25.

2-[2-(Methanesulfonylamino)benzoylamino]benzoic acid—Compound 17b 17b was synthesized by procedures A, E, F, and C.

1H-NMR (360 MHz; Pyr): δ 13.40 (s, 1H), 9.01 (d, J=8.4 Hz, 1H), 8.50 (dd, J=7.9, 1.4 Hz, 1H), 8.15 (d, J=7.9 Hz, 1H), 8.03 (d, J=8.3 Hz, 1H), 7.60 (td, J=7.9, 1.3 Hz, 1H), 7.44 (t, J=7.8 Hz, 1H), 7.23 (t, J=7.7 Hz, 1H), 7.08 (t, J=7.6 Hz, 1H), 3.31 (s, 3H).

13C-NMR (91 MHz; Pyr): δ 174.29, 169.26, 143.36, 142.11, 135.70, 135.07, 133.93, 130.29, 125.65, 124.17, 122.43, 120.68, 41.70.

ESIMS m/z calcd for $[C_{15}H_{15}N_2O_5S]^+$ 335.35. found 335.26.

2-[2-(p-Toluenesulfonylamino)benzoylamino]benzoic acid—Compound 17c 17c was synthesized by procedures A, E, F, and C.

1H-NMR (500 MHz; Pyr): δ 13.13 (s, 1H), 9.01 (d, J=8.4 Hz, 1H), 8.48 (dd, J=7.9, 1.4 Hz, 1H), 8.02 (d, J=8.2 Hz, 1H), 7.96 (dd, J=7.8, 0.9 Hz, 1H), 7.92 (d, J=8.2 Hz, 2H), 7.64-7.60 (ddd, J=8.6, 7.1, 1.5 Hz, 1H), 7.41-7.38 (ddd, J=8.3, 7.2, 1.1 Hz, 1H), 7.24-7.21 (ddd, J=7.9, 7.1, 0.8 Hz, 1H), 7.03-6.97 (m, 3H), 1.95 (s, 3H).

13C-NMR (126 MHz; Pyr): δ 172.16, 167.23, 143.91, 141.39, 139.40, 136.83, 133.79, 132.78, 131.97 129.75, 127.90, 127.45, 124.52, 124.04, 123.32, 122.57, 120.39, 118.61, 20.83.

ESIMS m/z calcd for $[C_{21}H_{19}N_2O_5S]^+$ 411.09. found 411.14.

2-[2-(Trimethylacetylamino)benzoylamino]benzoic acid—Compound 17d 17d was synthesized by procedures A, E, F, and C.

1H-NMR (500 MHz; Pyr): δ 13.34 (s, 1H), 11.94 (s, 1H), 9.14 (dd, J=8.5, 1.1 Hz, 2H), 8.51 (dd, J=7.9, 1.6 Hz, 1H), 8.16 (dd, J=7.9, 1.3 Hz, 1H), 7.62-7.58 (ddd, J=8.7, 7.1, 1.6 Hz, 1H), 7.45-7.42 (ddd, J=8.5, 7.2, 1.3 Hz, 1H), 7.23-7.20 (ddd, J=8.3, 7.3, 1.0 Hz, 1H), 7.05-7.02 (ddd, J=8.3, 7.3, 1.1 Hz, 1H), 1.39 (s, 9H).

13-C NMR (126 MHz; Pyr): δ 177.1, 172.3, 168.1, 141.7, 141.5, 133.8, 132.9, 132.1, 127.8, 123.2, 122.8, 121.4, 121.1, 120.5, 118.8, 27.5.

ESIMS m/z calcd for $[C_{19}H_{21}N_2O_4]^+$ 341.14. found 341.24.

2-[[2-(Cyclohexanecarboxylamino)benzoyl]amino]benzoic acid—Compound 17e 17e was synthesized by procedures A, E, F, and C.

1H-NMR (400 MHz; Pyr): δ 13.28 (s, 1H), 11.71 (s, 1H), 9.15 (d, J=8.3 Hz, 1H), 9.12 (dd, J=8.5, 1.0 Hz, 1H), 8.52 (dd, J=7.9, 1.6 Hz, 1H), 8.17 (dd, J=7.9, 1.3 Hz, 1H), 7.60 (ddd, J=8.5, 7.2, 1.3 Hz, 1H), 7.45 (ddd, J=8.5, 7.2, 1.3 Hz, 1H), 7.23 (ddd, J=8.0, 7.0, 1.0 Hz, 1H), 7.06 (ddd, J=8.1, 7.0, 1.1 Hz, 1H), 2.45 (tt, J=11.4, 3.6 Hz, 1H), 2.13-2.06 (m, 2H), 1.74-1.61 (m, 4H), 1.53-1.46 (m, 1H), 1.27-1.06 (m, 3H).

13-C NMR (126 MHz; Pyr): δ 175.7, 173.4, 169.1, 142.8, 142.3, 134.8, 133.9, 133.2, 129.0, 124.3, 124.0, 122.71, 122.52, 121.6, 120.0, 48.1, 30.9, 26.96, 26.80.

ESIMS m/z calcd for $[C_{21}H_{23}N_2O_4]^+$ 367.16. found 367.24.

2-[2-(4-Carboxybutanoylamido)benzoyl]aminobenzoic acid—Compound 17f 17f was synthesized by procedures A, E, F, and C.

1H-NMR (500 MHz; Pyr): δ 13.31 (s, 1H), 11.83 (s, 1H), 9.16 (d, J=8.3 Hz, 1H), 9.01 (d, J=8.4 Hz, 1H), 8.53 (d, J=7.8 Hz, 1H), 8.13 (d, J=7.9 Hz, 1H), 7.62 (t, J=7.5 Hz, 1H), 7.40 (t, J=7.8 Hz, 1H), 7.23 (t, J=7.8 Hz, 1H), 7.02 (t, J=7.5 Hz, 1H), 3.05 (m, 4H).

13-C NMR (126 MHz; Pyr): δ 175.1, 172.4, 171.0, 167.9, 141.9, 140.9, 133.9, 132.8, 132.2, 128.0, 123.1, 121.8, 120.6, 118.9, 33.3, 30.0.

ESIMS m/z calcd for $[C_{18}H_{17}N_2O_6]^+$ 357.10. found 357.23.

2-[2-(Benzylamino)benzoylamino]benzoic acid—Compound 17g 17g was synthesized by procedures A, E, G, and C.

1H-NMR (360 MHz; Pyr): δ 13.13 (s, 1H), 9.21 (d, J=8.4 Hz, 1H), 8.51 (dd, J=7.9, 1.4 Hz, 1H), 8.16 (d, J=7.9 Hz, 1H), 7.61-7.58 (m, 1H), 7.49 (d, J=7.4 Hz, 2H), 7.32 (t, J=7.5 Hz, 2H), 7.25 (app. q., J=7.4 Hz, 2H), 7.16 (t, J=7.4 Hz, 1H), 6.81 (d, J=8.4 Hz, 1H), 6.65 (t, J=7.5 Hz, 1H), 4.46 (s, 2H).

13-C NMR (91 MHz; Pyr): δ 172.4, 168.9, 150.9, 142.7, 139.8, 133.9, 133.5, 132.1, 128.9, 128.4, 127.55, 127.36, 122.5, 120.4, 118.1, 116.0, 115.6, 112.7, 47.1.

ESIMS m/z calcd for $[C_{21}H_{19}N_2O_3]^+$ 347.13. found 347.22.

2-[2-(2-Fluorobenzoylamino)-benzoylamino]benzoic acid—Compound 17h 17h was synthesized by procedures A, E, F, and C.

1H-NMR (360 MHz; Pyr): δ 13.43 (s, 1H), 12.47 (d, J=6.1 Hz, 1H), 9.16 (d, J=8.4 Hz, 2H), 8.52 (d, J=7.8 Hz, 1H), 8.52 (d, J=7.8 Hz, 1H), 8.25 (td, J=7.7, 1.5 Hz, 1H), 8.19 (d, J=7.9 Hz, 1H), 7.53 (d, J=7.5 Hz, 1H), 7.49 (d, J=7.6 Hz, 1H), 7.44-7.38 (m, 1H), 7.23-7.17 (m,), 7.11 (t, J=7.6 Hz, 1H).

13C-NMR (91 MHz; Pyr): δ 173.90, 169.15, 163.70, 162.01 (d, J=251.0 Hz), 143.25, 141.75, 137.24, 136.97, 135.22, 135.16, 134.20, 133.60, 133.15, 129.43, 126.4 (d, J=2.7 Hz), 125.34, 125.00, 124.72, 123.99, 122.02, 120.45, 118.1 (d, J=24 Hz).

ESIMS m/z calcd for $[C_{21}H_{14}FN_2O_4]^-$, 377.09. found: 377.20.

2-[2-(3-Fluorobenzoylamino)-benzoylamino]benzoic acid—17i 17i was synthesized by procedures A, E, F, and C.

1H-NMR (500 MHz; Pyr): δ 13.90 (s, 1H), 12.82 (s, 1H), 9.10-9.07 (m, 2H), 8.56-8.52 (m, J=1.0 Hz, 1H), 8.27 (d, J=7.5 Hz, 1H), 8.05 (d, J=7.8 Hz, 1H), 8.02 (dt, J=9.6, 2.1 Hz, 1H), 7.51 (app dt, J=11.0, 7.9 Hz, 2H), 7.44 (app td, J=7.9, 5.8 Hz, 1H), 7.27 (td, J=8.4, 2.4 Hz, 1H), 7.20-7.15 (m, 2H).

13C-NMR (126 MHz; Pyr): δ 168.04, 164.04, 164.02, 163.01 (d, J=246.4 Hz), 140.66, 137.86, 137.81, 135.73, 135.54, 133.26, 132.97, 132.20, 131.03, 130.97, 128.17, 123.77, 123.36, 123.14, 123.12, 121.59, 120.50, 118.91 (d, J=21.3 Hz, 3C), 114.81 (d, J=23.0 Hz).

ESIMS m/z calcd for $[C_{21}H_{16}FN_2O_4]$+, 379.35. found: 379.37.

2-[2-(4-Fluorobenzoylamino)-benzoylamino]benzoic acid—17j 17j was synthesized by procedures A, E, F, and C.

1H-NMR (360 MHz; Pyr): δ 13.61 (s, 1H), 12.78 (s, 1H), 9.23 (d, J=8.3 Hz, 1H), 9.15 (d, J=8.3 Hz, 1H), 8.56 (d, J=7.7 Hz, 1H), 8.32 (dd, J=8.0, 5.7 Hz, 2H), 8.25 (d, J=7.8 Hz, 1H), 7.62-7.56 (m, 1H), 7.51 (t, J=7.9 Hz, 1H), 7.27-7.20 (m, J=7.5 Hz, 3H), 7.10 (t, J=7.7 Hz, 1H).

13C-NMR (91 MHz; Pyr): δ 168.55, 165.35 (d, J=251.0 Hz), 164.56, 141.96, 141.54, 134.03, 133.41, 132.54, 132.25, 130.65, 130.55, 128.42, 121.91, 121.66, 121.03, 116.40, 116.16.

ESIMS m/z calcd for $[C_{21}H_{16}FN_2O_4]$+, 379.35. found: 379.43.

2-[2-(Phenylacetylamino)benzoylamino]benzoic acid—Compound 17k 17k was synthesized by procedures A, E, F, and C.

1H-NMR (500 MHz; Pyr): δ 13.25 (s, 1H), 11.72 (s, 1H), 9.11 (dd, J=8.4, 0.5 Hz, 1H), 8.95 (d, J=8.1 Hz, 1H), 8.53 (dd, J=7.9, 1.5 Hz, 1H), 8.09 (dd, J=7.9, 1.2 Hz, 1H), 7.67-7.64 (ddd, J=7.0, 1.6 Hz, 1H), 7.40-7.35 (m, 3H), 7.29-7.23 (m, 3H), 7.04-7.01 (ddd, J=7.0, 1.0 Hz, 2H), 3.93 (s, 2H).

13C-NMR (126 MHz; Pyr): δ 172.36, 169.81, 167.73, 141.87, 140.66, 133.88, 132.72, 132.20, 129.98, 129.02, 127.85, 127.31, 123.34, 123.30, 122.18, 121.78, 120.60, 118.88, 45.73.

ESIMS m/z calcd for $[C_{22}H_{19}N_2O_4]^+$ 375.13. found 375.18.

2-[2-(benzoylamino)benzoylamino]phenylacetic acid—Compound 23

23 was synthesized by procedures E, D, E, F, and C.

1H-NMR (400 MHz, Pyr): δ 12.94 (s, 1H), 11.59 (s, 1H), 9.29 (d, J=8.5 Hz, 1H), 8.36 (d, J=7.8 Hz, 1H), 8.29 (d, J=7.4 Hz, 2H), 7.99 (d, J=7.8 Hz, 1H), 7.56-7.49 (m, 2H), 7.44-7.40 (m, 1H), 7.37-7.33 (m, 3H), 7.24 (t, J=7.6 Hz, 1H), 7.08 (t, J=7.6 Hz, 1H), 4.10 (s, 2H).

$^{13}C$ NMR (400 MHz, Pyridine-d5): δ 176.4, 169.4, 166, 142, 137.8, 133.6, 132.6, 132.2, 131.7, 129.7, 129.3, 128.6, 128.3, 127.4, 127.2, 122.0, 121.4, 40.5

13-C NMR (100 MHz, Pyr): δ 175.5, 168.8, 165.3, 141.5, 137.4, 135.6, 133.1, 132.0, 131.7, 131.4, 129.1, 128.8, 128.1, 127.8, 126.82, 126.65, 123.0, 121.4, 120.8, 40.1.

ESIMS m/z calcd for $[C_{22}H_{17}N_2O_4]^+$, 373.13. found: 373.20.

2-[2-(benzoylamino)phenylacetylamino]benzoic acid—Compound 28

28 was synthesized by procedures D, E, F, and C.

1H-NMR (400 MHz, Pyr): δ 12.72 (s, 1H), 11.30 (s, 1H), 8.95 (d, J=8.4 Hz, 1H), 8.48-8.45 (m, 2H), 8.41 (dd, J=7.7, 1.5 Hz, 1H), 8.37 (d, J=8.0 Hz, 1H), 7.51-7.44 (m, 5H), 7.37-7.33 (m, 1H), 7.13 (t, J=7.5 Hz, 2H), 4.03 (s, 2H).

13-C NMR (100 MHz, Pyr): δ 172.1, 171.3, 165.9, 141.7, 138.5, 135.6, 135.3, 133.8, 132.03, 131.90, 131.3, 128.97, 128.83, 128.28, 128.17, 125.54, 125.43, 120.5, 43.6.

ESIMS m/z calcd for $[C_{22}H_{19}N_2O_4]^+$, 375.13. found: 375.22.

2-[2-(2-fluorobenzoylamino)-benzoylamino]-4-chlorobenzoic acid—Compound 35a 35b was synthesized by procedures I, A, J, A, and C.

1H-NMR (500 MHz; Pyr): δ 14.04 (s, 1H), 12.39 (d, J=6.1 Hz, 1H), 9.25 (d, J=1.7 Hz, 1H), 9.14 (d, J=8.3 Hz, 1H), 8.49 (d, J=8.4 Hz, 1H), 8.24-8.21 (m, 2H), 7.50 (t, J=7.8 Hz, 1H), 7.40-7.36 (m, 1H), 7.23-7.09 (m, 4H).

13C-NMR (126 MHz; Pyr): δ 171.89, 167.76, 162.24 (d, J=2.5 Hz), 160.27 (d, J=250.9 Hz), 142.56, 140.24, 138.43, 133.59 (d, J=8.8 Hz), 133.38, 132.73, 131.49 (d, J=1.6 Hz), 128.07, 124.83 (d, J=3.4 Hz), 123.73, 122.95, 122.57, 122.47, 122.40, 119.87, 118.91, 116.58 (d, J=23.1 Hz).

ESIMS m/z calcd for $[C_{21}H_{13}ClFN_2O_4]^-$, 411.06. found: 411.16.

2-[2-(2-fluorobenzoylamino)benzoylamino]-5-chlorobenzoic acid—Compound 35b 35c was synthesized by procedures I, A, J, A, and C.

Compound 35b was only available in very small quantities. Consequently, some signals are lost in the noise or obscured by solvent signals.

1H-NMR (500 MHz; Pyr): δ 12.69 (s, 1H), 9.19 (d, J=8.5 Hz, 1H), 9.12 (d, J=8.8 Hz, 1H), 8.79 (s, 2H), 8.28 (d, J=7.7 Hz, 1H), 8.23 (t, J=7.1 Hz, 1H), 7.51-7.46 (m, 2H), 7.42-7.37 (m, 1H), 7.04-7.01 (m, 1H).

13C-NMR (126 MHz; Pyr): δ 168.65, 141.60, 141.33, 134.65 (d, J=8.5 Hz), 133.43, 132.96, 132.61, 132.11, 129.38, 125.96 (d, J=3.4 Hz), 123.28, 122.58, 117.73 (d, J=22.9 Hz).

ESIMS m/z calcd for $[C_{21}H_{13}ClFN_2O_4]^-$, 411.06. found: 411.18.

2-[2-(2-fluorobenzoylamino)-benzoylamino]-4-methoxybenzoic acid—Compound 35c 35d was synthesized by procedures H, A, E, A, and C.

$^1$H NMR (400 MHz, Pyridine-d5): δ 13.39 (s, 1H, CONH), 12.35 (s, 1H, CONH), 9.13 (d, J=8.3 Hz, 1H), 8.85 (d, J=2.5 Hz, 1H), 8.48 (d, J=8.9 Hz, 1H), 8.23 (t, J=8.0 Hz, 1H), 8.18 (d, J=7.5 Hz, 1H), 7.50 (t, J=8.1 Hz, 1H), 7.36-7.42 (q, (d, J=7.6, 15.0 Hz, 1H), 7.16-7.20 (under pyridine-$d_5$, 2H), 7.11-7.14 (m, 1H), 6.83-6.86 (dd, J=3.4, 8.7 Hz, 1H), 3.75 (s, 3H, —$ArOCH_3$).

$^{13}$C NMR (400 MHz, Pyridine-d5): δ 172.1, 167.9, 164.1, 162.2, 160.4 (d, J=249.9 Hz), 143.6, 140.2, 133.8, 133.7 (d, J=8.3 Hz), 132.7, 131.6, 127.9, 124.9, 124.8, 123.9, 122.9, 122.6, 116.6 (d, J=24.2 Hz), 110.9, 109.0, 105.8, 55.3.

ESIMS m/z calcd for $[C_{22}H_{18}FN_2O_5]^+$, 409.38. found: 409.39.

2-[2-(2-fluorobenzoylamino)-benzoylamino]-5-methoxybenzoic acid—Compound 35d 35e was synthesized by procedures H, A, E, A, and C.

1H-NMR (400 MHz, Pyr): δ 13.62 (s, 1H), 12.62 (d, J=5.9 Hz, 1H), 9.17 (d, J=8.4 Hz, 1H), 9.13 (d, J=9.2 Hz, 1H), 8.26-8.20 (m, 2H), 8.18 (d, J=3.0 Hz, 1H), 7.48 (t, J=7.7 Hz, 1H), 7.43-7.37 (m, 1H), 7.22-7.16 (m, under Pyr, 3H), 7.09 (t, J=7.6 Hz, 1H), 3.70 (s, 3H).

13C-NMR (100 MHz, Pyr): δ 172.38, 167.05, 162.19 (d, J=2.7 Hz), 160.34 (d, J=250.9 Hz), 155.25, 140.21, 135.42, 133.62, 133.53, 132.34, 131.55, 131.52, 127.85, 124.85 (d, J=3.4 Hz), 123.74, 123.68, 122.89, 122.30, 121.93, 119.20, 116.58 (d, J=23.2 Hz), 116.17, 55.19.

ESIMS m/z calcd for $[C_{22}H_{18}FN_2O_5]^+$, 409.38. found: 409.45.

2-[2-(2-fluorobenzoylamino)-benzoylamino]-4,5-difluorobenzoic acid—Compound 35e 35a was synthesized by procedures H, A, E, A, and C.

1H-NMR (400 MHz, Pyr): δ 13.73 (s, 1H), 12.37 (d, J=5.4 Hz, 1H), 9.14 (d, J=8.4 Hz, 1H), 9.05 (app q, J=7.3 Hz, 1H), 8.33 (t, J=9.9 Hz, 1H), 8.25 (t, J=7.2 Hz, 1H), 8.19 (d, J=7.4 Hz, 1H), 7.51 (t, J=7.3 Hz, 1H), 7.42 (q, J=5.8 Hz, 1H), 7.25-7.23 (m, 2H), 7.14 (t, J=7.5 Hz, 1H).

13C-NMR (100 MHz, Pyr): δ 171.01, 167.67, 162.36, 160.44 (d, J=250.7 Hz, 14C), 152.44 (dd, J=250.0, 13.0 Hz, 15C), 145.39 (dd, J=245.0, 13.0 Hz, 15C), 140.32, 138.92, 138.82, 133.88, 133.80, 132.97, 131.70, 128.09, 125.03 (d, J=3.0 Hz), 123.96, 122.66, 122.49, 120.41 (d, J=19.1 Hz), 116.75 (d, J=23.4 Hz), 109.32 (d, J=24.0 Hz).

ESIMS m/z calcd for $[C_{21}H_{14}F_3N_2O_4]^+$, 415.33. found: 415.37.

2-[4-chloro-2-(2-fluorobenzoylamino)-benzoylamino]benzoic acid—Compound 35f 35f was synthesized by procedures A, J, A, and C.

1H-NMR (500 MHz; Pyr): δ 13.42 (s, 1H), 12.51 (d, J=6.4 Hz, 1H), 9.26 (d, J=2.1 Hz, 1H), 9.09 (d, J=8.3 Hz, 1H), 8.51 (dd, J=7.8, 1.5 Hz, 1H), 8.22 (td, J=7.7, 1.7 Hz, 1H), 8.07 (d, J=8.5 Hz, 1H), 7.55-7.52 (m, 1H, under pyr), 7.44-7-39 (m, 1H), 7.22-7.17 (m, 3H), 7.09 (dd, J=8.5, 2.1 Hz, 1H).

13C-NMR (126 MHz; Pyr): δ 172.42, 166.73, 162.34 (d, J=2.2 Hz), 160.36 (d, J=251.0 Hz), 141.52, 141.32, 138.22, 133.95, 133.88, 133.68, 132.04, 131.63 (d, J=1.6 Hz), 129.22, 124.93 (d, J=3.4 Hz), 123.59, 123.12, 121.90, 120.80, 120.47, 118.96, 116.62 (d, J=23.4 Hz).

ESIMS m/z calcd for $[C_{21}H_{13}ClFN_2O_4]^-$, 411.06. found: 411.15.

2-[5-chloro-2-(2-fluorobenzoylamino)-benzoylamino]benzoic acid—Compound 35g 35g was synthesized by procedures A, J, A, and C.

1H-NMR (500 MHz; Pyr): δ 13.39 (s, 1H), 12.28 (d, J=6.2 Hz, 1H), 9.07 (t, J=8.7 Hz, 2H), 8.51 (d, J=7.8 Hz, 1H), 8.22 (td, J=7.6, 1.5 Hz, 1H), 8.19 (d, J=2.3 Hz, 1H), 7.53 (m, 2H), 7.43-7.39 (m, 1H), 7.22-7.16 (m, 4H).

13C-NMR (126 MHz; Pyr): δ 172.21, 166.12, 162.13 (d, J=2.2 Hz), 160.35 (d, J=250.7 Hz), 141.32, 138.73, 133.82, 133.75, 133.58, 132.26, 132.03, 131.63 (d, J=2.0 Hz), 128.41, 127.88, 124.88 (d, J=3.2 Hz), 124.49, 123.99, 120.52, 119.35, 116.57 (d, J=23.1 Hz).

ESIMS m/z calcd for $[C_{21}H_{13}ClFN_2O_4]^-$, 411.06. found: 411.15.

2-[4-methoxy-2-(2-fluorobenzoylamino)-benzoylamino]benzoic acid—Compound 35h 35h was synthesized by procedures A, E, A, and C.

1H-NMR (400 MHz, Pyr): δ 13.25 (s, 1H), 12.82 (d, J=4.6 Hz, 1H), 9.07 (d, J=8.3 Hz, 1H), 8.87 (br s, 1H), 8.47 (d, J=7.8 Hz, 1H), 8.20-8.15 (m, 2H), 7.51 (t, J=7.8 Hz, 1H), 7.47-7.40 (m, 1H), 7.25-7.15 (m, under Pyr, 3H), 6.73 (dd, J=8.8, 2.5 Hz, 1H), 3.72 (s, 3H).

13C-NMR (100 MHz, Pyr): δ 172.38, 167.60, 163.14, 162.59 (d, J=2.0 Hz), 160.27 (d, J=250.8 Hz), 142.49, 141.86, 133.80, 133.71, 132.06, 131.39 (d, J=1.5 Hz), 129.59, 124.97 (d, J=3.3 Hz), 122.96, 120.44, 118.64, 116.66 (d, J=23.1 Hz), 114.32, 109.68, 107.16, 55.32.

ESIMS m/z calcd for $[C_{22}H_{18}FN_2O_5]^+$, 409.38. found: 409.45.

2-[5-methoxy-2-(2-fluorobenzoylamino)-benzoylamino]benzoic acid—Compound 35i 35i was synthesized by procedures A, E, A, and C.

1H-NMR (360 MHz, Pyr): δ 13.35 (s, 1H), 12.21 (d, J=6.6 Hz, 1H), 9.15 (d, J=8.3 Hz, 1H), 9.08 (d, J=9.1 Hz, 1H), 8.49 (d, J=7.7 Hz, 1H), 8.27 (t, J=7.5 Hz, 1H), 7.78 (d, J=2.3 Hz, 1H), 7.54 (t, J=8.0 Hz, 1H), 7.44-7.38 (m, 1H), 7.23-7.17 (m, under Pyr, 4H), 3.77 (s, 3H).

13C-NMR (91 MHz, Pyr): δ 172.41, 167.30, 161.94, 160.76 (d, J=250.0 Hz), 155.82, 141.79, 133.87, 133.61 (d, J=8.7 Hz), 133.45, 132.16, 131.76, 124.98 (d, J=3.1 Hz), 124.43, 124.33, 123.61, 123.30, 120.47, 118.87, 118.67, 116.66 (d, J=24.1 Hz), 112.61, 55.40.

ESIMS m/z calcd for $[C_{22}H_{18}FN_2O_5]^+$, 409.11. found: 409.39.

2-[4,5-difluoro-2-(2-fluorobenzoylamino)-benzoylamino]benzoic acid—Compound 35j 35j was synthesized by procedures A, E, A, and C.

1H-NMR (360 MHz; Pyr): δ 14.10 (s, 1H), 12.58 (d, J=6.3 Hz, 1H), 9.13-9.03 (m, 2H), 8.58 (d, J=7.7 Hz, 1H), 8.23 (td, J=7.8, 1.3 Hz, 1H), 8.01 (t, J=9.7 Hz, 1H), 7.49 (t, J=8.1 Hz, 1H), 7.43 (q, J=6.7 Hz, 1H), 7.25-7.13 (m, 3H).

13C-NMR (91 MHz; Pyr): δ 174.51, 165.64, 162.38, 160.39 (d, J=251.0 Hz), 145.5 (dd, J=246.0, 13.8 Hz), 141.35, 137.97, 137.86, 134.14, 134.05, 132.64, 132.34, 131.79, 125.08 (d, J=2.7 Hz, 1C), 123.30, 122.41, 120.23, 119.21, 116.93 (d, J=19.0 Hz), 116.78 (d, J=24.0 Hz), 111.30 (d, J=23.6 Hz).

ESIMS m/z calcd for $[C_{21}H_{12}F_3N_2O_4]^-$, 413.08. found: 413.19.

The invention claimed is:

1. A compound selected from:

Ethyl 2-[3-(benzoylamino)benzoylamino]benzoate
2-[[3-(Benzoylamino)benzoyl]amino]benzoic acid
Ethyl 2-[4-(benzoylamino)benzoylamino]benzoate
2-[2-(Acetylamino)benzoylamino]benzoic acid
2-[2-(Trimethylacetylamino)benzoylamino]benzoic acid
2-[[2-(Cyclohexanecarboxylamino)benzoyl]amino]benzoic acid
2-[2-(4-Carboxybutanoylamido)benzoyl]aminobenzoic acid
2-[2-(2-Fluorobenzoylamino)-benzoylamino]benzoic acid
2-[2-(3-Fluorobenzoylamino)-benzoylamino]benzoic acid
2-[2-(4-Fluorobenzoylamino)-benzoylamino]benzoic acid
Ethyl 2-[2-(benzoylamino)benzoylamino]benzoate
Ethyl 2-[2-(acetylamino)benzoylamino]benzoate
Ethyl 2-[2-(trimethylacetylamino)benzoylamino]benzoate
Ethyl 2-[[2-(cyclohexanecarboxylamino)benzoyl]amino]benzoate
Ethyl 2-[2-(phenylacetylamino)benzoylamino]benzoate
Ethyl 2-[2-(4-carboxybutanoylamido)benzoyl]aminobenzoate
2-[[2-(Benzoylamino)benzoyl]amino]benzoic acid
2-[2-(Acetylamino)benzoylamino]benzoic acid
2-[2-(Trimethylacetylamino)benzoylamino]benzoic acid
2-[[2-(Cyclohexanecarboxylamino)benzoyl]amino]benzoic acid
2-[2-(Phenylacetylamino)benzoylamino]benzoic acid
2-[2-(4-Carboxybutanoylamido)benzoyl]aminobenzoic acid
2-[2-(benzoylamino)benzoylamino]phenylacetic acid
2-[2-(benzoylamino)phenylacetylamino]benzoic acid
2-[2-(2-fluorobenzoylamino)-benzoylamino]-4-chlorobenzoic acid
2-[2-(2-fluorobenzoylamino)benzoylamino]-5-chlorobenzoic acid
2-[2-(2-fluorobenzoylamino)-benzoylamino]-4-methoxybenzoic acid
2-[2-(2-fluorobenzoylamino)-benzoylamino]-5-methoxybenzoic acid
2-[2-(2-fluorobenzoylamino)-benzoylamino]-4,5-difluorobenzoic acid
2-[4-chloro-2-(2-fluorobenzoylamino)-benzoylamino]benzoic acid
2-[5-chloro-2-(2-fluorobenzoylamino)-benzoylamino]benzoic acid
2-[4-methoxy-2-(2-fluorobenzoylamino)-benzoylamino]benzoic acid
2-[5-methoxy-2-(2-fluorobenzoylamino)-benzoylamino]benzoic acid, and
2-[4,5-difluoro-2-(2-fluorobenzoylamino)-benzoylamino]benzoic acid or a pharmaceutically acceptable salt thereof.

2. A pharmaceutical composition comprising a compound according to claim 1, and a pharmaceutically acceptable adjuvant, diluent or carrier.

3. A method for the prophylaxis or treatment of a viral disease, the method comprising administering a therapeutically effective amount of a compound of the general formula (I), (II) or (III) or a pharmaceutically acceptable salt thereof to a subject in need of such treatment:

Formula (I)

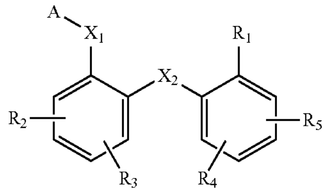

-continued

Formula (II)

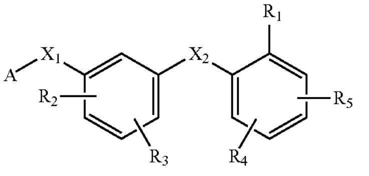

Formula (III)

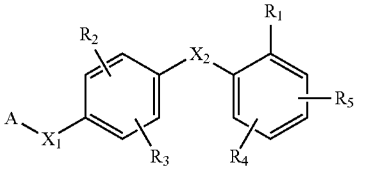

wherein $X_1$ is —CO—NH—, $X_2$ is —CO—NH—,

A is selected from the group consisting of hydrogen, —$C_{1-8}$alkyl, —$(CH_2)_n C_{3-7}$cycloalkyl, —$(CH_2)_n$phenyl, —$(CH_2)_n$naphthyl, —$(CH_2)_n$heteroaryl, —$(CH_2)_n CO_2H$, and —$(CH_2)_n CO_2C_{1-8}$alkyl, wherein alkyl, cycloalkyl, phenyl, naphthyl, and heteroaryl are unsubstituted or substituted with one to three substituents independently selected from halogen, —$C_{1-6}$ alkyl, and —$C_{1-6}$ alkyloxy;

$R_1$ is selected from hydrogen, —$CO_2H$, —$CO_2C_{1-4}$alkyl, —$C_{1-6}$alkyl, tetrazol-5-yl, and —$CONR_6R_6$;

$R_2$, $R_3$, $R_4$ and $R_5$ are each independently selected from hydrogen, halogen, and —$C_{1-6}$ alkyloxy;

each $R_6$ is independently selected from the group consisting of hydrogen and —$C_{1-8}$alkyl; and n is 0, 1, 2, 3, 4, or 5.

4. The method according to claim 3 wherein A is selected from phenyl, naphthyl, and heteroaryl, unsubstituted or substituted with one to three substituents independently selected from halogen, —$C_{1-6}$alkyl, and —$C_{1-6}$ alkyloxy.

5. The method according to claim 3 wherein $R_1$ is selected from —$CO_2H$, and —$CO_2C_{1-4}$alkyl.

6. The method according to claim 3 wherein the viral disease is selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Retrovirus infections including lentivirus infections, such as HIV infections, Togavirus infections including Rubivirus infections.

7. The method according to claim 6 wherein the viral disease is an Adenovirus infection.

8. The method according to claim 6 wherein the viral disease is selected from a Herpes virus infection and a Picorna virus infection.

9. The method according to claim 8 wherein the herpes virus infection is caused by HSV-1, HSV-2 and/or varicella zoster virus.

10. The method according to claim 3 wherein the compound is selected from 2-[[2-(Benzoylamino)benzoyl]amino]-benzoic acid
2-[[2-(4-Methyl-benzoylamino)benzoyl]amino]-benzoic acid
2-[[3-(Benzoylamino)benzoyl]amino]-benzamide
2-[[3-(2-Methyl-benzoylamino)benzoyl]amino]-benzoic acid
2-[[2-(4-Methoxy-benzoylamino)benzoyl]amino]-benzoic acid
4-Methyl-N-{2-[(2-methylphenyl)carbamoyl]phenyl}-benzamide
Ethyl 2-[3-(benzoylamino)benzoylamino]benzoate
2-[[3-(Benzoylamino)benzoyl]amino]benzoic acid
Ethyl 2-[4-(benzoylamino)benzoylamino]benzoate
2-[[4-(Benzoylamino)benzoyl]amino]benzoic acid
2-Benzoylamino-N-phenyl-benzamide
2-[2-(Acetylamino)benzoylamino]benzoic acid
2-[2-(Trimethylacetylamino)benzoylamino]benzoic acid
2-[[2-(Cyclohexanecarboxylamino)benzoyl]amino]benzoic acid
2-[2-(4-Carboxybutanoylamido)benzoyl]aminobenzoic acid
2-[2-(2-Fluorobenzoylamino)-benzoylamino]benzoic acid
2-[2-(3-Fluorobenzoylamino)-benzoylamino]benzoic acid
2-[2-(4-Fluorobenzoylamino)-benzoylamino]benzoic acid
2-[2-(Phenylacetylamino)benzoylamino]benzoic acid
Ethyl 2-[2-(benzoylamino)benzoylamino]benzoate
Ethyl 2-[2-(acetylamino)benzoylamino]benzoate
Ethyl 2-[2-(trimethylacetylamino)benzoylamino]benzoate
Ethyl 2-[[2-(cyclohexanecarboxylamino)benzoyl]amino]benzoate
Ethyl 2-[2-(phenylacetylamino)benzoylamino]benzoate
Ethyl 2-[2-(4-carboxybutanoylamido)benzoyl]aminobenzoate
2-[[2-(Benzoylamino)benzoyl]amino]benzoic acid
2-[2-(Acetylamino)benzoylamino]benzoic acid
2-[2-(Trimethylacetylamino)benzoylamino]benzoic acid
2-[[2-(Cyclohexanecarboxylamino)benzoyl]amino]benzoic acid
2-[2-(Phenylacetylamino)benzoylamino]benzoic acid
2-[2-(4-Carboxybutanoylamido)benzoyl]aminobenzoic acid
2-[2-(benzoylamino)benzoylamino]phenylacetic acid
2-[2-(benzoylamino)phenylacetylamino]benzoic acid
2-[2-(2-fluorobenzoylamino)-benzoylamino]-4-chlorobenzoic acid
2-[2-(2-fluorobenzoylamino)benzoylamino]-5-chlorobenzoic acid
2-[2-(2-fluorobenzoylamino)-benzoylamino]-4-methoxybenzoic acid
2-[2-(2-fluorobenzoylamino)-benzoylamino]-5-methoxybenzoic acid
2-[2-(2-fluorobenzoylamino)-benzoylamino]-4,5-difluorobenzoic acid
2-[4-chloro-2-(2-fluorobenzoylamino)-benzoylamino]benzoic acid
2-[5-chloro-2-(2-fluorobenzoylamino)-benzoylamino]benzoic acid
2-[4-methoxy-2-(2-fluorobenzoylamino)-benzoylamino]benzoic acid
2-[5-methoxy-2-(2-fluorobenzoylamino)-benzoylamino]benzoic acid and 2-[4,5-difluoro-2-(2-fluorobenzoylamino)-benzoylamino]benzoic acid or a pharmaceutically acceptable salt thereof.

11. The method according to claim 3, wherein A is selected from the group consisting of: hydrogen, —$C_{1-8}$alkyl, —$(CH_2)_n$$C_{3-7}$cycloalkyl, —$(CH_2)_n$phenyl, —$(CH_2)_nCO_2H$, and —$(CH_2)_nCO_2C_{1-8}$alkyl, wherein alkyl, cycloalkyl, and phenyl are unsubstituted or substituted with one to three substituents independently selected from halogen, —$C_{1-6}$alkyl, and —$C_{1-6}$ alkyloxy.

12. The method according to claim 3, wherein A is phenyl, unsubstituted or substituted with one to three substituents independently selected from halogen, —$C_{1-6}$alkyl, and —$C_{1-6}$ alkyloxy.

13. The method according to claim 3 wherein n is 0 or 1.

* * * * *

UNITED STATES PATENT AND TRADEMARK OFFICE

CERTIFICATE OF CORRECTION

PATENT NO. : 8,993,622 B2
APPLICATION NO. : 13/703481
DATED : March 31, 2015
INVENTOR(S) : Göran Wadell et al.

It is certified that error appears in the above-identified patent and that said Letters Patent is hereby corrected as shown below:

Claims

Column 59, Line 31, In Claim 3, before "and" insert -- -$C_{1-6}$ alkyl --.

Signed and Sealed this
Thirteenth Day of October, 2015

Michelle K. Lee
*Director of the United States Patent and Trademark Office*